(12) United States Patent
Yao et al.

(10) Patent No.: US 10,611,736 B2
(45) Date of Patent: Apr. 7, 2020

(54) 2,4,6-TRISUBSTITUTED S-TRIAZINE COMPOUND, PREPARATION METHOD THEREFOR, AND USE THEREOF

(71) Applicants: Nanjing Shiqi Pharmaceutical Co. Ltd., Nanjing, Jiangsu (CN); LUODA BIOSCIENCES, INC., Chuzhou, Anhui (CN)

(72) Inventors: Qizheng Yao, Jiangsu (CN); Jianping Wu, Anhui (CN); Ruihuan Chen, Union City, CA (US); Lei Zhang, Jiangsu (CN); Shining Yao, Jiangsu (CN); Lian Mo, Union City, CA (US); Qingqing Zhang, Jiangsu (CN)

(73) Assignee: Aluda Pharmaceuticals, Inc., Menlo Park, CA (US)

( * ) Notice: Subject to any disclaimer, the term of this patent is extended or adjusted under 35 U.S.C. 154(b) by 0 days.

(21) Appl. No.: 16/300,162

(22) PCT Filed: May 11, 2017

(86) PCT No.: PCT/CN2017/083914
§ 371 (c)(1),
(2) Date: Nov. 9, 2018

(87) PCT Pub. No.: WO2017/193954
PCT Pub. Date: Nov. 16, 2017

(65) Prior Publication Data
US 2019/0144399 A1 May 16, 2019

(30) Foreign Application Priority Data

May 12, 2016 (CN) .......................... 2016 1 0325809

(51) Int. Cl.
| | | |
|---|---|---|
| *C07D 251/16* | (2006.01) | |
| *C07D 251/18* | (2006.01) | |
| *C07D 403/04* | (2006.01) | |
| *C07D 413/04* | (2006.01) | |
| *C07D 251/48* | (2006.01) | |
| *A61K 31/53* | (2006.01) | |
| *A61K 31/5377* | (2006.01) | |
| *A61P 35/00* | (2006.01) | |

(52) U.S. Cl.
CPC ............ *C07D 251/48* (2013.01); *A61K 31/53* (2013.01); *A61K 31/5377* (2013.01); *A61P 35/00* (2018.01); *C07D 251/16* (2013.01); *C07D 251/18* (2013.01); *C07D 403/04* (2013.01)

(58) Field of Classification Search
CPC .. C07D 251/16; C07D 251/18; C07D 403/04; C07D 413/04
See application file for complete search history.

(56) References Cited

U.S. PATENT DOCUMENTS

2012/0178758 A1* 7/2012 Tao et al. ............ C07D 251/28
514/245

FOREIGN PATENT DOCUMENTS

| CN | 1578663 A | 2/2005 |
|---|---|---|
| CN | 102573482 A | 7/2012 |
| EP | 1882475 A1 | 1/2008 |
| WO | 2009138758 A3 | 11/2009 |

OTHER PUBLICATIONS

Banker et al. "Modern Pharmaceutics", 3rd Ed. p. 596 (1996). (Year: 1996).*
Burger's Medicinal Chemistry,, edited by Manfred E.Wolf, 5th Ed. Part 1, pp. 975-977 (1995). (Year: 1995).*
International Search Report for corresponding PCT Application No. PCT/CN2017/083914, dated Aug. 18, 2017.
Saczewski, et al., "Synthesis, structure and anticancer activity of novel 2, 4-diamino-1,3,5-triazine derivatives," European Journal of Medicinal Chemistry, vol. 41, pp. 219-225, (2006).
Dos Santos, et al., "Vimentin regulates activation of the NLRP3 inflammasome", Nat Commun., vol. 6, Sep. 12, 2015; doi:10.1038/ncomms7574.
Surolia, et al., "Vimentin intermediate filament assembly regulates fibroblast invasion in fibrogenic lung injury", JCI Insight. Apr. 4, 2019; vol. 4, No. 7, e123253. https://doi.org/10.1172/jci.insight.123253.
Troeger, et al., "Deactivation of Hepatic Stellate Cells During Liver Fibrosis Resolution in Mice", Gastroenterology 2012;143:1073-1083.
Vassiliadis, et al., "Circulating levels of citrullinated and MMP-degraded vimentin (VICM) in liver fibrosis related pathology", Am J Transl Res. 2012;4(4):403-14.
Wang, et al., "Vimentin expression is required for the development of EMT-related renal fibrosis following unilateral ureteral obstruction in mice", Am J Physiol Renal Physiol 315: F769—F780, 2018.
Wang, et al., "Characterization of the Roles of Vimentin in Regulating the Proliferation and Migration of HSCs during Hepatic Fibrogenesis", Cells 2019, 8, 1184; doi:10.3390/cells8101184.

(Continued)

*Primary Examiner* — Emily A Bernhardt
(74) *Attorney, Agent, or Firm* — Greenberg Traurig, LLP; Fang Xie

(57) ABSTRACT

The present invention provides a 2,4,6-trisubstituted s-triazine compound represented by general formula (I) or pharmaceutically acceptable salts, prodrugs or solvates thereof, a preparation method therefor, and use of these compounds in preparing drugs for preventing or treating diseases associated with protein kinase and vimentin dysregulation, and cell vacuolization, and in particular, drugs for treating or preventing cancer growth and metastasis, tissue fibrosis and atherosclerosis.

(I)

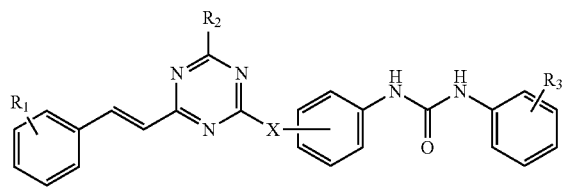

16 Claims, 6 Drawing Sheets
Specification includes a Sequence Listing.

(56) References Cited

OTHER PUBLICATIONS

Davis, et al., "Targeting EMT in cancer: opportunities for pharmacological intervention", Trends in Pharmacological Sciences, 2014, 35(9), pp. 479-488.
Gonzalez, et al., "Signaling mechanisms of the epithelial-mesenchymal transition", Sci Signal. 2014; 7 (344): re8.
Ivaska, et al., "Novel functions of vimentin in cell adhesion, migration, and signaling", Exp Cell Res. 2007; 313 (10):2050-62.
Kitambi, et al., "Vulnerability of glioblastoma cells to catastrophic vacuolization and death induced by a small molecule", Cell. 2014; 157(2):313-28.
Maltese, et al., "Methuosis: nonapoptotic cell death associated with vacuolization of macropinosome and endosome compartments", Am J Pathol. 2014; 184 (6):1630-42.
Robinson, et al., "Synthesis and evaluation of indole-based chalcones as inducers of methuosis, a novel type of nonapoptotic cell death", J Med Chem. 2012; 55 (5):1940-56.
Sarria, et al., "A functional role for vimentin intermediate filaments in the metabolism of lipoprotein-derived cholesterol in human SW-13 cells", J Biol Chem. Sep. 25, 1992; 267 (27):19455-63.
Trabbic, et al., "Synthesis and biological evaluation of indolyl-pyridinyl-propenones having either methuosis or microtubule disruption activity", J Med Chem. 2015; 58 (5):2489-512.

\* cited by examiner

A

Vimentin (3KLT)

B

50 (L1)

C

| | Index | Name | LibDockScore |
|---|---|---|---|
| 1 | 1 | 3KLT | |
| 2 | 2 | 50 | 165.195 |
| 3 | 3 | 50 | 164.725 |
| 4 | 4 | 50 | 164.469 |
| 5 | 5 | 50 | 162.489 |
| 6 | 6 | 50 | 161.565 |
| 7 | 7 | 50 | 160.764 |
| 8 | 8 | 50 | 160.617 |
| 9 | 9 | 50 | 159.422 |
| 10 | 10 | 50 | 157.376 |
| 11 | 11 | 50 | 157.159 |

D

E

2,4,6-TRISUBSTITUTED S-TRIAZINE COMPOUND, PREPARATION METHOD THEREFOR, AND USE THEREOF

CROSS REFERENCE TO RELATED APPLICATIONS

This application is a U.S. National Phase application under 35 U.S.C. 371 of International Application No. PCT/CN2017/083914, filed May 11, 2017, which claims priority to and the benefit of Chinese Application No. 201610325809.0 filed May 12, 2016, the disclosure of each of which is incorporated herein by reference.

TECHNICAL FIELD

The present disclosure relates to a genus of 2,4,6-trisubstituted-1,3,5-triazine (also named symmetric triazine or sym-triazine, s-triazine) compounds or pharmaceutically acceptable salts, prodrugs or solvates thereof, preparation methods therefor, and uses thereof.

BACKGROUND ART

In addition to well-known forms of cell death, such as apoptosis, necrosis, autophagy and the like, a new form of cell death, methuosis, has been revealed in recent years. The hallmark of this form of death is a displacement of normal cytoplasm by large fluid-filled vacuoles generated by macropinocytotic vesicles or macropinosomes inside the cell. Consequently, the cell loses its metabolic capacity and its membrane integrity without cell shrinkage and nuclear fragmentation associated with apoptosis, also significantly different from necrosis and autophagy (Maltese et al. Methuosis: nonapoptotic cell death associated with vacuolization of macropinosome and endosome compartments. Am J Pathol. 2014; 184 (6): 1630-42). Owing to the different mechanism of methuosis from that of cell apoptosis, a drug causing cell death by methuosis could overcome the resistance of tumor cells to antiapoptotic drugs or drugs acting through other mechanisms, and therefore open a new venue for the development of therapies against cancer (Robinson et al. Synthesis and evaluation of indole-based chalcones as inducers of methuosis, a novel type of nonapoptotic cell death. J Med Chem. 2012; 55 (5):1940-56; Kitambi et al. Vulnerability of glioblastoma cells to catastrophic vacuolization and death induced by a small molecule. Cell. 2014; 157(2):313-28; Trabbic et al. Synthesis and biological evaluation of indolyl-pyridinyl-propenones having either methuosis or microtubule disruption activity. J Med Chem. 2015; 58 (5):2489-512).

Vimentin is a major intermediate filament protein expressed in mesenchymal cells, including the cells of connective tissue, muscle, vascular endothelium and blood. Highly conservative evolution and dynamic expression during different developmental stages suggest that vimentin is physiologically important. Together with microtubules and actin microfilaments, intermediate filaments form a cytoskeleton. In addition to the function of improving mechanical strength of cells so as to sustain cellular shape, cytoskeleton integrity and orderly spatial distribution of subcellular structure, vimentin can also regulate the function of integrin, so as to affect cellular adhesion and migration; collaborate with dynein such as microtubules, microfilaments and the like to affect membrane transport of vesicles; and act as a scaffold for receptor and protein kinase so as to affect signal transduction, etc (Ivaska et al. Novel functions of vimentin in cell adhesion, migration, and signaling. Exp Cell Res. 2007; 313 (10):2050-62).

Vimentin is closely related with lipid metabolism, having control over transport of low density lipoprotein (LDL)-derived cholesterol from lysosome to locations for esterification thereof (Sarria et al. A functional role for vimentin intermediate filaments in the metabolism of lipoprotein-derived cholesterol in human SW-13 cells. J Biol Chem. 1992 Sep. 25; 267 (27): 19455-63). In view of the high expression of vimentin in the cells of vascular endothelium and smooth muscle, targeting vimentin could be a strategy that is worth trying for the development of new drugs for treating or preventing cardiovascular diseases such as atherosclerosis. Vimentin expression is a marker of epithelial-mesenchymal transition (EMT). EMT is not only an essential mechanism in normal physiological processes such as embryonic development and tissue repair, but also an indispensable route in pathological processes such as organ fibrosis, and tumor formation and progression (Gonzalez et al. Signaling mechanisms of the epithelial-mesenchymal transition. Sci Signal. 2014; 7 (344): re8). Therefore, by using vimentin as a target to intervene in the EMT process, it's possible to develop a new drug for promoting tissue regeneration, inhibiting organ degeneration, treating tissue fibrosis, preventing tumor metastasis, etc (Davis et al. Targeting EMT in cancer: opportunities for pharmacological intervention. Trends Pharmacol Sci. 2014; 35(9): 479-88).

SUMMARY

As a result of a study on a structure-activity relationship, the present disclosure provides a specific type of compounds that are highly effective in causing cell death through methuosis. On such a basis, a reliable, effective method for fishing a target protein with a probe is used to separate and identify the target protein of the compound that causes cell death by methuosis, wherein the target protein is verified to be vimentin.

Therefore, the present disclosure provides a genus of 2,4,6-trisubstituted s-triazine compounds, a method for preparing the same, and use of these compounds for regulation of protein kinase and vimentin, and induction of cell methuosis.

According to the present disclosure, the 2,4,6-trisubstituted s-triazine compound is represented by Formula (I):

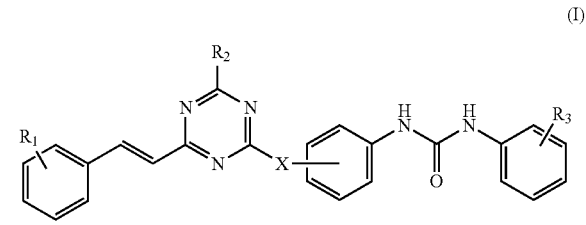

wherein:

$R_1$ is hydrogen, halogen, nitro, amino, hydroxyl, $C_1$-$C_{12}$ alkyl, $C_1$-$C_6$ alkoxyl, $C_1$-$C_6$ alkylamino, di-$C_1$-$C_6$ alkylamino, hydroxymethyl, aminomethyl;

$R_2$ is —$NR_4R_5$, wherein $R_4$ and $R_5$ are independently selected from a group consisting of hydrogen, $C_1$-$C_6$ alkyl, and $C_1$-$C_6$ haloalkyl; or $R_4$, $R_5$ and the nitrogen atom bonded to them form a saturated or unsaturated 4 to 6-member heterocyclic ring containing optionally an additional heteroatom selected from a group consisting of $NR_6$, O and S, wherein the heterocyclic ring may be substituted with hydroxyl, halogen, nitro, amino or $C_1$-$C_6$ alkyl, wherein $R_6$ is hydrogen, hydroxyl, $C_1$-$C_6$ alkyl, or $C_1$-$C_6$ haloalkyl;

$R_3$ is hydrogen, halogen, nitro, amino, hydroxyl, $C_1$-$C_{12}$ alkyl, $C_1$-$C_6$ alkoxyl, $C_1$-$C_6$ alkylamino, di-$C_1$-$C_6$ alkylamino, hydroxymethyl, aminomethyl or —$COR_a$;

wherein $R_a$ is OH or $NR_7R_8$, wherein $R_7$ and $R_8$ are independently selected from a group consisting of hydrogen, $C_1$-$C_6$ alkyl optionally substituted with one or more substituents selected from halogen or $NR_9R_{10}$, and $C_1$-$C_6$ alkyl substituted with 3-($C_2$-$C_6$ alkynyl)-3H-diaziridinyl; or $R_7$, $R_8$ and the nitrogen atom bonded to them form a 4 to 6-member heterocyclic ring containing optionally an additional heteroatom selected from a group consisting of N, O and S, and optionally substituted with $C_1$-$C_6$ alkyl;

wherein $R_9$ and $R_{10}$ are independently selected from a group consisting of hydrogen and $C_1$-$C_6$ alkyl; or $R_9$, $R_{10}$ and the nitrogen atom bonded to them form a 4 to 6-member heterocyclic ring containing optionally an additional heteroatom selected from a group consisting of N, O and S; and X is NH or O, linked to the phenyl group on a para- or meta-position.

The present disclosure further includes pharmaceutically acceptable salts, prodrugs or solvates of the compound represented by Formula (I).

In one or more embodiments, $R_1$ is hydrogen, halogen or nitro.

In one or more embodiments, $R_2$ is —$NR_4R_5$, wherein $R_4$ and $R_5$ are independently selected from a group consisting of hydrogen, $C_1$-$C_6$ alkyl and $C_1$-$C_6$ haloalkyl; or $R_4$, $R_5$ and the nitrogen atom bonded to them form a saturated or unsaturated 4 to 6-member heterocyclic ring containing optionally an additional heteroatom selected from a group consisting of $NR_6$, O and S, wherein the heterocyclic ring may be substituted with hydroxyl, halogen, nitro, amino or $C_1$-$C_6$ alkyl, wherein $R_6$ is hydrogen, hydroxyl, or $C_1$-$C_6$ alkyl.

In one or more embodiments, $R_2$ is —$NR_4R_5$, wherein $R_4$ and $R_5$ are independently selected from a group consisting of hydrogen and $C_1$-$C_6$ alkyl; or $R_4$, $R_5$ and the nitrogen atom bonded to them form a saturated 4 to 6-member heterocyclic ring containing optionally an additional heteroatom selected from a group consisting of $NR_6$, O and S, wherein the heterocyclic ring may be substituted with hydroxyl, halogen, nitro, amino or $C_1$-$C_6$ alkyl, wherein $R_6$ is hydrogen or $C_1$-$C_6$ alkyl.

In one or more embodiments, $R_2$ is —$NR_4R_5$, wherein $R_4$, $R_5$ and the nitrogen atom bonded to them form a saturated 4 to 6-member heterocyclic ring containing optionally an additional heteroatom selected from a group consisting of $NR_6$ and O, wherein the heterocyclic ring is optionally substituted with a substituent selected from hydroxyl and $C_1$-$C_6$ alkyl, wherein $R_6$ is hydrogen or $C_1$-$C_6$ alkyl.

In one or more embodiments, $R_3$ is hydrogen, halogen, nitro, amino, hydroxyl, $C_1$-$C_6$ alkyl, hydroxymethyl, aminomethyl or —$COR_a$, wherein $R_a$ is OH or $NR_7R_8$, wherein $R_7$ and $R_8$ are independently selected from a group consisting of hydrogen, $C_1$-$C_6$ alkyl optionally substituted with one or more substituents selected from halogen or $NR_9R_{10}$, and $C_1$-$C_6$ alkyl substituted with 3-($C_2$-$C_6$ alkynyl)-3H-diaziridinyl; or $R_7$, $R_8$ and the nitrogen atom bonded to them form a 4 to 6-member heterocyclic ring containing optionally an additional heteroatom selected from a group consisting of N, O and S, and optionally substituted with $C_1$-$C_6$ alkyl; wherein $R_9$ and $R_{10}$ are independently selected from a group consisting of hydrogen and $C_1$-$C_6$ alkyl; or $R_9$, $R_{10}$ and the nitrogen atom bonded to them form a 4 to 6-member heterocyclic ring containing optionally an additional heteroatom selected from a group consisting of N, O and S.

In one or more embodiments, $R_3$ is halogen, $C_1$-$C_6$ alkoxyl or —$COR_a$; wherein $R_a$ is OH or $NR_7R_8$, wherein $R_7$ and $R_8$ are independently selected from a group consisting of $C_1$-$C_6$ alkyl optionally substituted with $NR_9R_{10}$, and $C_1$-$C_6$ alkyl substituted with 3-($C_2$-$C_6$ alkynyl)-3H-diaziridinyl; or $R_7$, $R_8$ and the nitrogen atom bonded to them form a saturated 4 to 6-member heterocyclic ring containing optionally an additional heteroatom selected from N or O, and optionally substituted with $C_1$-$C_6$ alkyl; wherein $R_9$ and $R_{10}$ are independently selected from a group consisting of hydrogen and $C_1$-$C_6$ alkyl; or $R_9$, $R_{10}$ and the nitrogen atom bonded to them form a saturated 4 to 6-member heterocyclic ring containing optionally an additional heteroatom selected from N or O.

In one or more embodiments, X is NH, linked to the phenyl group on a para- or meta-position.

In one or more embodiments, in Formula (I):

$R_1$ is hydrogen, halogen or nitro;

$R_2$ is —$NR_4R_5$, wherein $R_4$ and $R_5$ are independently selected from a group consisting of hydrogen, $C_1$-$C_6$ alkyl, $C_1$-$C_6$ haloalkyl; or $R_4$, $R_5$ and the nitrogen atom bonded to them form a saturated or unsaturated 4 to 6-member heterocyclic ring containing optionally an additional heteroatom selected from a group consisting of $NR_6$, O and S, wherein the heterocyclic ring may be substituted with hydroxyl, halogen, nitro, amino or $C_1$-$C_6$ alkyl; wherein $R_6$ is hydrogen, hydroxyl or $C_1$-$C_6$ alkyl; and $R_3$ is hydrogen, halogen, nitro, amino, hydroxyl, $C_1$-$C_6$ alkyl, hydroxymethyl, aminomethyl or —$COR_a$; wherein $R_a$ is OH or $NR_7R_8$, wherein $R_7$ and $R_8$ are independently selected from a group consisting of hydrogen, $C_1$-$C_6$ alkyl optionally substituted with one or more substituents selected from halogen or $NR_9R_{10}$, and $C_1$-$C_6$ alkyl substituted with 3-($C_2$-$C_6$ alkynyl)-3H-diaziridinyl; or $R_7$, $R_8$ and the nitrogen atom bonded to them form a 4 to 6-member heterocyclic ring containing optionally an additional heteroatom selected from a group consisting of N, O and S, and optionally substituted with $C_1$-$C_6$ alkyl; wherein $R_9$ and $R_{10}$ are independently selected from a group consisting of hydrogen and $C_1$-$C_6$ alkyl; or $R_9$, $R_{10}$ and the nitrogen atom bonded to them form a 4 to 6-member heterocyclic ring containing optionally an additional heteroatom selected from a group consisting of N, O and S.

In one or more embodiments, in Formula (I):

$R_1$ is hydrogen, halogen or nitro;

$R_2$ is —$NR_4R_5$, wherein $R_4$, $R_5$ and the nitrogen atom bonded to them form a saturated 4 to 6-member heterocyclic ring containing optionally an additional heteroatom selected from a group consisting of $NR_6$ and O, wherein the heterocyclic ring is optionally substituted with a substituent selected from hydroxyl and $C_1$-$C_6$ alkyl; wherein $R_6$ is hydrogen or $C_1$-$C_6$ alkyl;

$R_3$ is halogen or —$COR_a$; wherein $R_a$ is OH or $NR_7R_8$, wherein $R_7$ and $R_8$ are independently selected from a group consisting of $C_1$-$C_6$ alkyl optionally substituted with $NR_9R_{10}$, and $C_1$-$C_6$ alkyl optionally substituted with 3-($C_2$-$C_6$ alkynyl)-3H-diaziridinyl; or $R_7$, $R_8$ and the nitrogen atom bonded to them form a saturated 4 to 6-member heterocyclic ring containing optionally an additional heteroatom selected from N or O, and optionally substituted with $C_1$-$C_6$ alkyl; wherein $R_9$ and $R_{10}$ are independently selected from a group consisting of hydrogen and $C_1$-$C_6$ alkyl; or $R_9$, $R_{10}$ and the nitrogen atom bonded to them form a saturated 4 to 6-member heterocyclic ring containing optionally an additional heteroatom selected from N or O; and X is NH, linked to the phenyl group on a para- or meta-position.

In some embodiments, preferably:

$R_1$ is hydrogen, halogen or nitro;

$R_2$ is —$NR_4R_5$, wherein $R_4$ and $R_5$ are independently selected from a group consisting of hydrogen, $C_1$-$C_6$ alkyl and $C_1$-$C_6$ haloalkyl; or $R_4$, $R_5$ and the nitrogen atom bonded to them form a saturated or unsaturated 4 to 6-member heterocyclic ring containing optionally an additional heteroatom selected from a group consisting of $NR_6$, O and S, wherein the heterocyclic ring may be substituted with hydroxyl, halogen, nitro, amino or $C_1$-$C_6$ alkyl; wherein $R_6$ is hydrogen, hydroxyl or $C_1$-$C_6$ alkyl;

$R_3$ is hydrogen, halogen, nitro, amino, hydroxyl, $C_1$-$C_6$ alkyl, hydroxymethyl, aminomethyl or —$CONR_7R_8$, wherein $R_7$ and $R_8$ are independently selected from a group consisting of hydrogen and optionally substituted $C_1$-$C_6$ alkyl; or $R_7$, $R_8$ and the nitrogen atom bonded to them form a 4 to 6-member heterocyclic ring containing optionally an additional heteroatom selected from N, O or S; wherein the $C_1$-$C_6$ alkyl may be optionally substituted with one or more halogen, $C_1$-$C_6$ alkylamino, di-$C_1$-$C_6$ alkylamino;

X is a para- or meta- NH or O.

In some embodiments, more preferably:

$R_1$ is hydrogen, halogen or nitro;

$R_2$ is —$NR_4R_5$, wherein $R_4$ and $R_5$ are independently selected from a group consisting of hydrogen and $C_1$-$C_6$ alkyl; or $R_4$, $R_5$ and the nitrogen atom bonded to them form a saturated 4 to 6-member heterocyclic ring containing optionally an additional heteroatom selected from a group consisting of $NR_6$, O and S, wherein the heterocyclic ring may be substituted with hydroxyl, halogen, nitro, amino or $C_1$-$C_6$ alkyl; wherein $R_6$ is hydrogen or $C_1$-$C_6$ alkyl;

$R_3$ is hydrogen, halogen, or —$CONR_7R_8$, wherein $R_7$ and $R_8$ are independently selected from a group consisting of hydrogen and optionally substituted $C_1$-$C_6$ alkyl; or $R_7$, $R_8$ and the nitrogen atom bonded to them form a saturated 4 to 6-member heterocyclic ring containing optionally an additional heteroatom selected from N, O or S; wherein the $C_1$-$C_6$ alkyl may be optionally substituted with one or more $C_1$-$C_6$ alkylamino, di-$C_1$-$C_6$ alkylamino;

X is a para- or meta- NH or O.

Preferably, the above Formula (I) compound includes:

(E)-1-(4-chlorophenyl)-3-(4-(4-(morpholin-1-yl)-6-styrenyl-1,3,5-triazinyl-2-amino)phenyl)urea (L1);

(E)-1-(4-fluorophenyl)-3-(4-(4-(morpholin-1-yl)-6-styrenyl-1,3,5-triazinyl-2-amino)phenyl)urea (L2);

(E)-1-(4-chlorophenyl)-3-(4-(4-(4-methylpiperazin-1-yl)-6-styrenyl-1,3,5-triazinyl-2-amino)phenyl)urea (L3);

(E)-1-(4-fluorophenyl)-3-(4-(4-(4-methylpiperazin-1-yl)-6-styrenyl-1,3,5-triazinyl-2-amino)phenyl)urea (L4);

(E)-1-(4-chlorophenyl)-3-(4-(4-(3-hydroxyazetidin-1-yl)-6-styrenyl-1,3,5-triazinyl-2-amino)phenyl)urea (L5);

(E)-1-(4-chlorophenyl)-3-(4-(4-(morpholin-1-yl)-6-(3-chlorostyrenyl)-1,3,5-triazinyl-2-amino)phenyl)urea (L6);

(E)-1-(4-fluorophenyl)-3-(4-(4-(morpholin-1-yl)-6-(3-chlorostyrenyl)-1,3,5-triazinyl-2-amino)phenyl)urea (L7);

(E)-1-(4-chlorophenyl)-3-(4-(4-(4-methylpiperazin-1-yl)-6-(3-chlorostyrenyl)-1,3,5-triazinyl-2-amino)phenyl)urea (L8);

(E)-1-(4-fluorophenyl)-3-(4-(4-(4-methylpiperazin-1-yl)-6-(3-chlorostyrenyl)-1,3,5-triazinyl-2-amino)phenyl)urea (L9);

(E)-1-(4-chlorophenyl)-3-(4-(4-(morpholin-1-yl)-6-(4-chlorostyrenyl)-1,3,5-triazinyl-2-amino)phenyl)urea (L10);

(E)-1-(4-fluorophenyl)-3-(4-(4-(morpholin-1-yl)-6-(4-chlorostyrenyl)-1,3,5-triazinyl-2-amino)phenyl)urea (L11);

(E)-1-(3-fluorophenyl)-3-(4-(4-(morpholin-1-yl)-6-(4-chlorostyrenyl)-1,3,5-triazinyl-2-amino)phenyl)urea (L12);

(E)-1-(4-chlorophenyl)-3-(4-(4-(4-methylpiperazin-1-yl)-6-(4-chlorostyrenyl)-1,3,5-triazinyl-2-amino)phenyl)urea (L13);

(E)-1-(4-fluorophenyl)-3-(4-(4-(4-methylpiperazin-1-yl)-6-(4-chlorostyrenyl)-1,3,5-triazinyl-2-amino)phenyl)urea (L14);

(E)-1-(3-fluorophenyl)-3-(4-(4-(4-methylpiperazin-1-yl)-6-(4-chlorostyrenyl)-1,3,5-triazinyl-2-amino)phenyl)urea (L15);

(E)-1-(4-chlorophenyl)-3-(4-(4-(morpholin-1-yl)-6-(3-nitrostyrenyl)-1,3,5-triazinyl-2-amino)phenyl)urea (L16);

(E)-1-(4-fluorophenyl)-3-(4-(4-(morpholin-1-yl)-6-(3-nitrostyrenyl)-1,3,5-triazinyl-2-amino)phenyl)urea (L17);

(E)-1-(4-chlorophenyl)-3-(4-(4-(4-methylpiperazin-1-yl)-6-(3-nitrostyrenyl)-1,3,5-triazinyl-2-amino)phenyl)urea (L18);

(E)-1-(4-fluorophenyl)-3-(4-(4-(4-methylpiperazin-1-yl)-6-(3-nitrostyrenyl)-1,3,5-triazinyl-2-amino)phenyl)urea (L19);

(E)-1-(4-chlorophenyl)-3-(4-(4-dimethylamino-6-(3-nitrostyrenyl)-1,3,5-triazinyl-2-amino)phenyl)urea (L20);

(E)-1-(4-chlorophenyl)-3-(4-(4-(pyrrolidin-1-yl)-6-(3-nitrostyrenyl)-1,3,5-triazinyl-2-amino)phenyl)urea (L21);

(E)-1-(4-chlorophenyl)-3-(4-(4-(3-hydroxyazetidin-1-yl)-6-(3-nitrostyrenyl)-1,3,5-triazinyl-2-amino)phenyl)urea (L22);

(E)-1-(4-chlorophenyl)-3-(3-(4-(morpholin-1-yl)-6-styrenyl-1,3,5-triazinyl-2-amino)phenyl)urea (L23);

(E)-1-(4-chlorophenyl)-3-(3-(4-(4-methylpiperazin-1-yl)-6-styrenyl-1,3,5-triazinyl-2-amino)phenyl)urea (L24);

(E)-1-(4-chlorophenyl)-3-(3-(4-(morpholin-1-yl)-6-(3-chlorostyrenyl)-1,3,5-triazinyl-2-amino)phenyl)urea (L25);

(E)-1-(4-chlorophenyl)-3-(3-(4-(4-methylpiperazin-1-yl)-6-(3-chlorostyrenyl)-1,3,5-triazinyl-2-amino)phenyl)urea (L26);

(E)-1-(4-chlorophenyl)-3-(3-(4-(morpholin-1-yl)-6-(3-nitrostyrenyl)-1,3,5-triazinyl-2-amino)phenyl)urea (L27);

(E)-1-(4-chlorophenyl)-3-(3-(4-(4-methylpiperazin-1-yl)-6-(3-nitrostyrenyl)-1,3,5-triazinyl-2-amino)phenyl)urea (L28);

(E)-N,N-dimethyl-4-(3-(4-(4-(morpholin-1-yl)-6-styrenyl-1,3,5-triazinyl-2-amino)phenyl)urea)benzamide (L29);

(E)-1-(4-((4-methylpiperidin-1-yl)formyl)phenyl)-3-(4-(4-(morpholin-1-yl)-6-styrenyl-1,3,5-triazinyl-2-amino)phenyl)urea (L30);

(E)-1-(4-((4-methylpiperazin-1-yl)formyl)phenyl)-3-(4-(4-(morpholin-1-yl)-6-styrenyl-1,3,5-triazinyl-2-amino)phenyl)urea (L31);

(E)-N-(2-(dimethylamino)ethyl)-4-(3-(4-(4-(morpholin-1-yl)-6-styrenyl-1,3,5-triazinyl-2-amino)phenyl)urea)benzamide (L32);

(E)-N-(2-(diethylamino)ethyl)-4-(3-(4-(4-(morpholin-1-yl)-6-styrenyl-1,3,5-triazinyl-2-amino)phenyl)urea)benzamide (L33);

(E)-N-(3-(dimethylamino)propyl)-4-(3-(4-(4-(morpholin-1-yl)-6-styrenyl-1,3,5-triazinyl-2-amino)phenyl)urea)benzamide (L34);

(E)-N-(2-(pyrrolidin-1-yl)ethyl)-4-(3-(4-(4-(morpholin-1-yl)-6-styrenyl-1,3,5-triazinyl-2-amino)phenyl)urea)benzamide (L35);

(E)-N-(2-(piperidin-1-yl)ethyl)-4-(3-(4-(4-(morpholin-1-yl)-6-styrenyl-1,3,5-triazinyl-2-amino)phenyl)urea)benzamide (L36);

(E)-N-(2-(morpholin-1-yl)ethyl)-4-(3-(4-(4-(morpholin-1-yl)-6-styrenyl-1,3,5-triazinyl-2-amino)phenyl)urea)benzamide (L37);

(E)-1-(4-methoxyphenyl)-3-(4-((4-(morpholin-1-yl)-6-styrenyl-1,3,5-triazin-2-yl)oxo)phenyl)urea (L38);

(E)-1-(4-chlorophenyl)-3-(4-((4-(morpholin-1-yl)-6-styrenyl-1,3,5-triazin-2-yl)oxo)phenyl)urea (L39);

(E)-1-(4-fluorophenyl)-3-(4-((4-(morpholin-1-yl)-6-styrenyl-1,3,5-triazin-2-yl)oxo)phenyl)urea (L40);

(E)-N-(2-(3-(1-butyn-4-yl)-3H-diaziridin-3-yl)ethyl)-4-(3-(4-((4-(morpholin-1-yl)-6-styrenyl-1,3,5-triazin-2-yl)amino)phenyl)urea)benzamide (79); and (E)-1-(4-carboxyphenyl)-3-(4-(4-(morpholin-1-yl)-6-styrenyl-1,3,5-triazinyl-2-amino)phenyl)urea (14).

DETAILED DESCRIPTION

Figure 1:
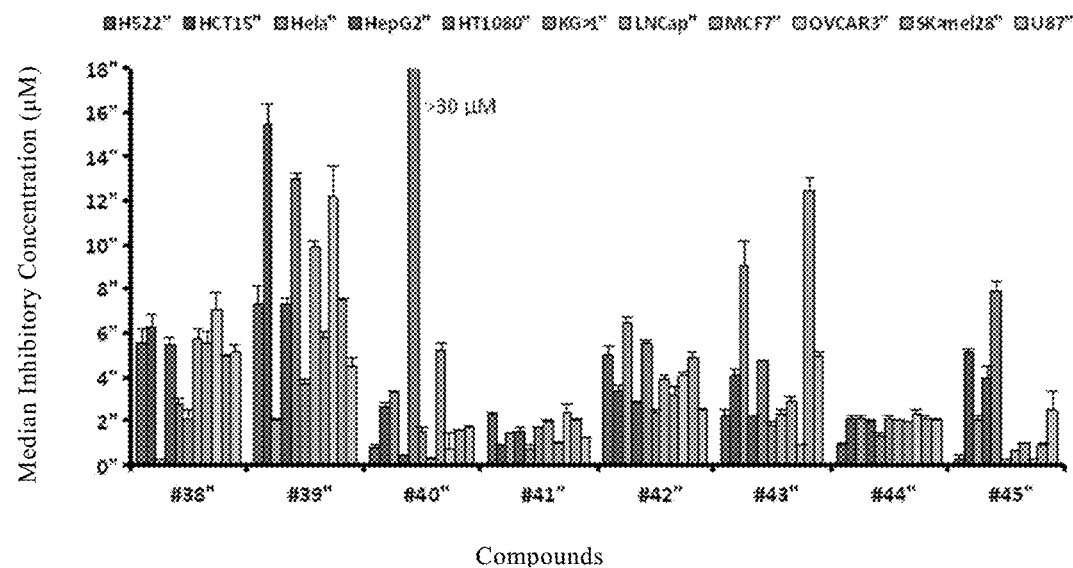
FIG. 1 In vitro inhibiting effect of compounds on various types of tumor cells. 8 compounds having different structural features (#38-#45, which are L20, L21, L16, L18, L14, L10, L13 and L11, respectively) were chosen. For tumor cells originated from 11 different types of cell sources, activity of the same compound on different tumor cells and sensitivity of the same tumor on compounds of different structural features were determined. For each compound, the bars from left to right are associated with H522、HCT15、Hela, HepG2、HT1080、KG1、LNCap、MCF7、OVCAR3、SK-me128 and U87, respectively. The data come from three independent sets of experiments, expressed as average±standard error.

It should be appreciated that, within the scope of this disclosure, the various technical features (e.g. the various scopes of the various groups) defined in the embodiments described above and the various technical features to be described specifically in the following (e.g. Examples) can be combined with each other, so as to form preferred technical solutions.

As used herein, "alkyl" refers to $C_1$-$C_{12}$ alkyl, for example, $C_1$-$C_6$ alkyl, such as methyl, ethyl, n-propyl, iso-propyl, n-butyl, iso-butyl, tert-butyl, n-amyl, etc.

"Heterocyclic ring" refers to a 4 to 6-member heterocyclic ring containing optionally a heteroatom selected from a group consisting of N, O and S. Heterocyclic ring may be a saturated or unsaturated heterocyclic ring. Exemplary heterocyclic rings include but are not limited to, for example, morpholinyl, pyrrolidinyl, piperazinyl, piperidinyl, azetidinyl, pyrazolyl, etc.

"Halogen" includes F, Cl, Br and I. "Carboxyl" refers to —COOH.

In "3-($C_2$-$C_6$ alkynyl)-3H-diaziridinyl", the alkynyl of the $C_2$-$C_6$ alkynyl is generally located on 1-position. In some embodiments, the "3-($C_2$-$C_6$ alkynyl)-3H-diaziridinyl" is "3-(1-butyn-4-yl)-3H-diaziridin-3-yl".

As used herein, $NR_7R$ and $NR_9R_{10}$ may be mono-$C_1$-$C_6$ alkylamino or di-$C_1$-$C_6$ alkylamino, wherein the $C_1$-$C_6$ alkyl may optionally be substituted, for example, by one or more halogen atoms, mono-$C_1$-$C_6$ alkylamino or di-$C_1$-$C_6$ alkylamino, or by a 4 to 6-member saturated heterocyclic ring containing N and optionally additional N or O. These heterocyclic rings include but are not limited to piperidinyl, piperazinyl, pyrrolidinyl, morpholinyl, etc. The heterocyclic ring may also be optionally substituted, for example, by $C_1$-$C_6$ alkyl.

In this disclosure, when a group is substituted, the number of the substituents may be for example 1, 2, 3 or 4. Generally, unless otherwise specified, substituents may be selected from halogen, $C_1$-$C_6$ alkyl, hydroxyl, carboxyl, amino, mono-$C_1$-$C_6$ alkylamino, di-$C_1$-$C_6$ alkylamino, nitro, 3-($C_2$-$C_6$ alkynyl)-3H-diaziridinyl, heterocyclic group (e.g. morpholinyl, pyrrolidinyl, piperazinyl, piperidinyl, azetidinyl, pyrazolyl, etc), $C_6$-$C_{14}$ aryl (e.g. phenyl) and the like.

In addition, related terms such as "isomer", "raceme", "prodrug", "solvate" used herein do not have obviously different meanings from the general meanings of said terms in the art. Those skilled in the art should know the meanings of these terms. For example, the term "isomer" refers to one of two or more compounds having the same molecular composition but different structures and properties. The term "raceme" refers to an equimolar mixture of an optically active chiral molecule and its enantiomer. The term "prodrug", also named prodrug, precursor drug, drug precursor and the like, refers to a compound exhibiting a pharmacological action only after conversion in vivo. The term "solvate" refers to a mixture consisting of a solvent and a compound.

In light of tumor plasticity and heterogeneity, by targeting a plurality of signal transduction pathways distinctly related with proliferation and death of tumor cells, and integrating pharmacophores acting on target molecules of these signal pathways, this disclosure proposes a new genus of compounds, i.e. s-triazine compounds formed by substituting with diaryl urea, aryl vinyl and saturated nitrogen (oxygen) heterocyclic ring, wherein this genus of compounds have a structure of Formula (I) as follows:

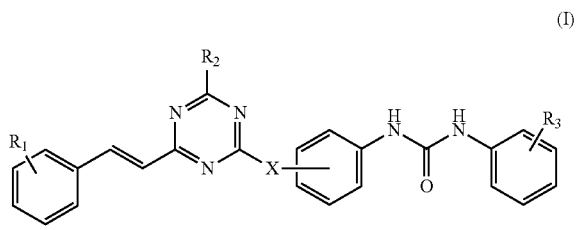

wherein $R_1$, $R_2$, $R_3$ and X are described above.

In some embodiments, $R_1$ is hydrogen, halogen or nitro; more preferably H, F, Cl or nitro.

In various forms of the structure herein, when $R_1$ is a group other than hydrogen, it is generally located on a meta- or para-position of the phenyl ring.

In some embodiments, $R_4$ and $R_5$ in $R_2$ are independently selected from a group consisting of hydrogen, $C_1$-$C_6$ alkyl and $C_1$-$C_6$ haloalkyl; or $R_4$, $R_5$ and the nitrogen atom bonded to them form a saturated or unsaturated 4 to 6-member heterocyclic ring containing optionally an additional heteroatom selected from a group consisting of $NR_6$, O and S, wherein the heterocyclic ring may be substituted with hydroxyl, halogen, nitro, amino or $C_1$-$C_6$ alkyl; wherein $R_6$ is hydrogen, hydroxyl, or $C_1$-$C_6$ alkyl. In some embodiments, $R_4$ and $R_5$ are independently selected from a group consisting of hydrogen and $C_1$-$C_6$ alkyl; or $R_4$, $R_5$ and the nitrogen atom bonded to them form a saturated 4 to 6-member heterocyclic ring containing optionally an additional heteroatom selected from a group consisting of $NR_6$, O and S, wherein the heterocyclic ring may be substituted with hydroxyl, halogen, nitro, amino or $C_1$-$C_6$ alkyl; wherein $R_6$ is hydrogen or $C_1$-$C_6$ alkyl. In some embodiments, $R_2$ is —$NR_4R_5$, wherein $R_4$, $R_5$ and the nitrogen atom bonded to them form a saturated 4 to 6-member heterocyclic ring containing optionally an additional heteroatom selected from a group consisting of $NR_6$ and O, wherein the heterocyclic ring is optionally substituted with a substituent selected from hydroxyl and $C_1$-$C_6$ alkyl; wherein $R_6$ is hydrogen or $C_1$-$C_6$ alkyl. In some embodiments, the saturated 4 to 6-member heterocyclic rings include but are not limited to morpholinyl, pyrrolidinyl, piperazinyl, piperidinyl, azetidinyl.

In some embodiments, $R_3$ is hydrogen, halogen, nitro, amino, hydroxyl, $C_1$-$C_6$ alkyl, hydroxymethyl, aminomethyl or —$COR_a$; wherein $R_a$ is OH or $NR_7R_8$, wherein $R_7$ and $R_8$ are independently selected from a group consisting of hydrogen, $C_1$-$C_6$ alkyl optionally substituted with one or more substituents selected from halogen or $NR_9R_{10}$, and $C_1$-$C_6$ alkyl substituted with 3-($C_2$-$C_6$ alkynyl)-3H-diaziridinyl; or $R_7$, $R_8$ and the nitrogen atom bonded to them form a 4 to 6-member heterocyclic ring containing optionally an additional heteroatom selected from a group consisting of N, O and S, and optionally substituted with $C_1$-$C_6$ alkyl; wherein $R_9$ and $R_{10}$ are independently selected from a group consisting of hydrogen and $C_1$-$C_6$ alkyl; or $R_9$, $R_{10}$ and the nitrogen atom bonded to them form a 4 to 6-member heterocyclic ring containing optionally an additional heteroatom selected from a group consisting of N, O and S. In some embodiments, $R_3$ is halogen, $C_1$-$C_6$ alkoxyl or —$COR_a$; wherein $R_a$ is OH or $NR_7R_8$, wherein $R_7$ and $R_8$ are independently selected from a group consisting of $C_1$-$C_6$ alkyl optionally substituted with $NR_9R_{10}$, and $C_1$-$C_6$ alkyl substituted with 3-($C_2$-$C_6$ alkynyl)-3H-diaziridinyl; or $R_7$, $R_8$ and the nitrogen atom bonded to them form a saturated 4 to 6-member heterocyclic ring containing optionally an additional heteroatom selected from N or O, and optionally substituted with $C_1$-$C_6$ alkyl; wherein $R_9$ and $R_{10}$ are independently selected from a group consisting of hydrogen and $C_1$-$C_6$ alkyl; or $R_9$, $R_{10}$ and the nitrogen atom bonded to them form a saturated 4 to 6-member heterocyclic ring containing optionally an additional heteroatom selected from N or O. In some embodiments, the heterocyclic ring formed by $R_7$, $R_8$ and the nitrogen atom bonded to them, and the heterocyclic ring formed by $R_9$, $R_{10}$ and the nitrogen atom bonded to them include but are not limited to piperidinyl, piperazinyl, pyrrolidinyl, and morpholinyl.

In various forms of the structure herein, when $R_3$ is a group other than H, it is generally located on a meta- or para-position of the phenyl group.

In some embodiments, X is NH, linked to the phenyl group on a para- or meta-position. In some embodiments, X is O, linked to the phenyl group on a para-position.

As described above, the various substituents or technical features in the various embodiments herein may be combined arbitrarily within the scope of the structure of Formula (I). Thus, for example, in some embodiments, in Formula (I), $R_1$ is hydrogen, halogen or nitro; $R_2$ is —$NR_4R_5$, wherein $R_4$ and $R_5$ are independently selected from a group consisting of hydrogen, $C_1$-$C_6$ alkyl and $C_1$-$C_6$ haloalkyl; or $R_4$, $R_5$ and the nitrogen atom bonded to them form a saturated or unsaturated 4 to 6-member heterocyclic ring containing optionally an additional heteroatom selected from a group consisting of $NR_6$, O and S, wherein the heterocyclic ring may be substituted with hydroxyl, halogen, nitro, amino or $C_1$-$C_6$ alkyl; wherein $R_6$ is hydrogen, hydroxyl, or $C_1$-$C_6$ alkyl; and $R_3$ is hydrogen, halogen, nitro, amino, hydroxyl, $C_1$-$C_6$ alkyl, hydroxymethyl, aminomethyl or —$COR_a$; wherein $R_a$ is OH or $NR_7R_8$, wherein $R_7$ and $R_8$ are independently selected from a group consisting of hydrogen, $C_1$-$C_6$ alkyl optionally substituted with one or more substituents selected from halogen or $NR_9R_{10}$, and $C_1$-$C_6$ alkyl substituted with 3-($C_2$-$C_6$ alkynyl)-3H-diaziridinyl; or $R_7$, $R_8$ and the nitrogen atom bonded to them form a 4 to 6-member heterocyclic ring containing optionally an additional heteroatom selected from a group consisting of N, O and S, and optionally substituted with $C_1$-$C_6$ alkyl; wherein $R_9$ and $R_{10}$ are independently selected from a group consisting of hydrogen and $C_1$-$C_6$ alkyl; or $R_9$, $R_{10}$ and the nitrogen atom bonded to them form a 4 to 6-member heterocyclic ring containing optionally an additional heteroatom selected from a group consisting of N, O and S. In other embodiments, in Formula (I), $R_1$ is hydrogen, halogen or nitro; $R_2$ is —$NR_4R_5$, wherein $R_4$, $R_5$ and the nitrogen atom bonded to them form a saturated 4 to 6-member heterocyclic ring containing optionally an additional heteroatom selected from a group consisting of $NR_6$ and O, wherein the heterocyclic ring is optionally substituted with a substituent selected from hydroxyl and $C_1$-$C_6$ alkyl; wherein $R_6$ is hydrogen or $C_1$-$C_6$ alkyl; $R_3$ is halogen or —$COR_a$; wherein $R_a$ is OH or $NR_7R_8$, wherein $R_7$ and $R_8$ are independently selected from a group consisting of $C_1$-$C_6$ alkyl optionally substituted with $NR_9R_{10}$, and $C_1$-$C_6$ alkyl substituted with 3-($C_2$-$C_6$ alkynyl)-3H-diaziridinyl; or $R_7$, $R_8$ and the nitrogen atom bonded to them form a saturated 4 to 6-member heterocyclic ring containing optionally an additional heteroatom selected from N or O, and optionally substituted with $C_1$-$C_6$ alkyl; wherein $R_9$ and $R_{10}$ are independently selected from a group consisting of hydrogen and $C_1$-$C_6$ alkyl; or $R_9$, $R_{10}$ and the nitrogen atom bonded to them form a saturated 4 to 6-member heterocyclic ring containing optionally an additional heteroatom selected from N or O; and X is NH, linked to the phenyl group on a para- or meta-position.

In some embodiments, the compound of Formula (I) herein has a structure shown by Formula (I-1) or Formula (I-2) as follows:

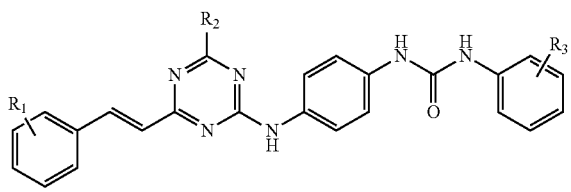

(I-1)

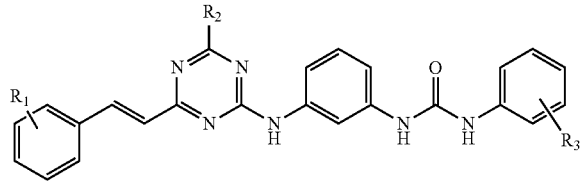

(I-2)

wherein:

$R_1$ is selected from a group consisting of hydrogen, halogen or nitro;

$R_2$ is selected from a group consisting of morpholinyl, pyrrolidinyl, piperazinyl, and azetidinyl optionally substituted with hydroxyl or $C_1$-$C_6$ alkyl; and $R_3$ is halogen or —$COR_a$; wherein $R_a$ is OH or $NR_7R_8$, wherein $R_7$ and $R_8$ are independently selected from a group consisting of $C_1$-$C_6$ alkyl optionally substituted with $NR_9R_{10}$, and $C_1$-$C_6$ alkyl substituted with 3-($C_2$-$C_6$ alkynyl)-3H-diaziridinyl; or $R_7$, $R_8$ and the nitrogen atom bonded to them form a saturated 4 to 6-member heterocyclic ring containing optionally an additional heteroatom selected from N or O, and optionally substituted with $C_1$-$C_6$ alkyl; wherein $R_9$ and $R_{10}$ are independently selected from a group consisting of hydrogen and $C_1$-$C_6$ alkyl; or $R_9$, $R_{10}$ and the nitrogen atom bonded to them form a saturated 4 to 6-member heterocyclic ring containing optionally an additional heteroatom selected from N or O.

In some embodiments of the above Formula (I-2), $R_3$ is halogen.

In some embodiments, the compound of Formula (I) herein has a structure shown by Formula (I-3) as follows:

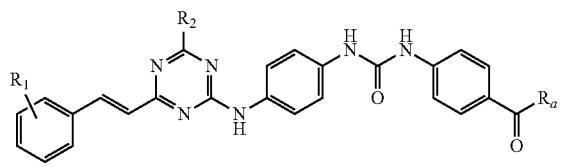

(I-3)

wherein:

$R_1$ is H;

$R_2$ is morpholinyl;

$R_a$ is OH or $NR_7R_8$, wherein $R_7$ and $R_8$ are independently selected from a group consisting of $C_1$-$C_6$ alkyl optionally substituted with $NR_9R_{10}$, and $C_1$-$C_6$ alkyl substituted with 3-($C_2$-$C_6$ alkynyl)-3H-diaziridinyl; or $R_7$, $R_8$ and the nitrogen atom bonded to them form a saturated 4 to 6-member heterocyclic ring containing optionally an additional heteroatom selected from N or O, and optionally substituted with $C_1$-$C_6$ alkyl; wherein $R_9$ and $R_{10}$ are independently selected from a group consisting of hydrogen and $C_1$-$C_6$ alkyl; or $R_9$, $R_{10}$ and the nitrogen atom bonded to them form a saturated 4 to 6-member heterocyclic ring containing optionally an additional heteroatom selected from N or O.

In some embodiments of Formula (I-1), $R_1$ is selected from a group consisting of hydrogen, halogen and nitro; $R_2$ is morpholinyl; $R_3$ is halogen or —$COR_a$; wherein $R_a$ is OH or $NR_7R_8$, wherein $R_7$ and $R_8$ are independently selected from a group consisting of $C_1$-$C_6$ alkyl optionally substituted with $NR_9R_{10}$, and $C_1$-$C_6$ alkyl substituted with 3-($C_2$-$C_6$ alkynyl)-3H-diaziridinyl; or $R_7$, $R_8$ and the nitrogen atom bonded to them form a saturated 4 to 6-member heterocyclic ring containing optionally an additional heteroatom selected from N or O, and optionally substituted with $C_1$-$C_6$ alkyl; wherein $R_9$ and $R_{10}$ are independently selected from a group consisting of hydrogen and $C_1$-$C_6$ alkyl; or $R_9$, $R_{10}$ and the nitrogen atom bonded to them form a saturated 4 to 6-member heterocyclic ring containing optionally an additional heteroatom selected from N or O. In some embodiments, in these compounds, $R_1$ (in the case of a substituent other than hydrogen) and $R_3$ are independently located on a meta- or para-position of the phenyl group, respectively. In some embodiments, in these compounds, when $R_1$ is a substituent other than hydrogen, it is located on a meta-position of the phenyl ring, and $R_3$ is located on a para-position of the phenyl group. In some embodiments, in these compounds, the saturated heterocyclic ring includes but is not limited to piperazinyl, piperidinyl, pyrrolidinyl, morpholinyl. In some embodiments, these compounds may particularly be used to induce vesicle aggregation in tumor cells, thereby leading to cell death by methuosis.

2,4,6-trisubstituted s-triazine compounds of the disclosure may be synthesized using the following methods:

Synthetic Scheme 1: Metaphenylene diamine or paraphenylene diamine (1) is used as a starting material, of which one amino group is protected by (Boc)$_2$O, to obtain intermediate 2 which reacts with one of various types of substituted phenyl isocyanates to obtain intermediate 3 from which the protective group Boc (t-butyloxycarbonyl) is removed via trifluoroacetic acid to obtain intermediate 4; cyanuric chloride (5) is reacted with methyl magnesium bromide (CH$_3$MgBr) to prepare intermediate 6 which reacts with one of various types of substituted benzaldehydes under reflux of concentrated hydrochloric acid to obtain intermediate 7 which is chlorinated with phosphorus oxychloride to obtain intermediate 8; and intermediate 8 and intermediate 4 undergo a reaction catalyzed by di-isopropyl ethylamine to obtain intermediate 9 which reacts with a heterocyclic amine such as morpholine or methyl pyperazine in the presence of di-isopropyl ethylamine to obtain a target compound.

The reaction formulae in Synthetic Scheme 1 are as follows:

Reagents in the reaction formulae in the above synthetic scheme: (a) a base, preferably potassium carbonate, (Boc)$_2$O, water, tetrahydrofuran, DMF; (b) substituted phenyl isocyanate, methylene dichloride; (c) trifluoroacetic acid, methylene dichloride; (d) a solution of methyl magnesium bromide in tetrahydrofuran; (e) substituted benzaldehyde, concentrated hydrochloric acid; (f) phosphorus oxychloride; (g) di-iso-propyl ethylamine, tetrahydrofuran; (h) heterocyclic amine, di-iso-propyl ethylamine, tetrahydrofuran.

The structural formulae of the target compounds of Synthetic Scheme 1 may include:

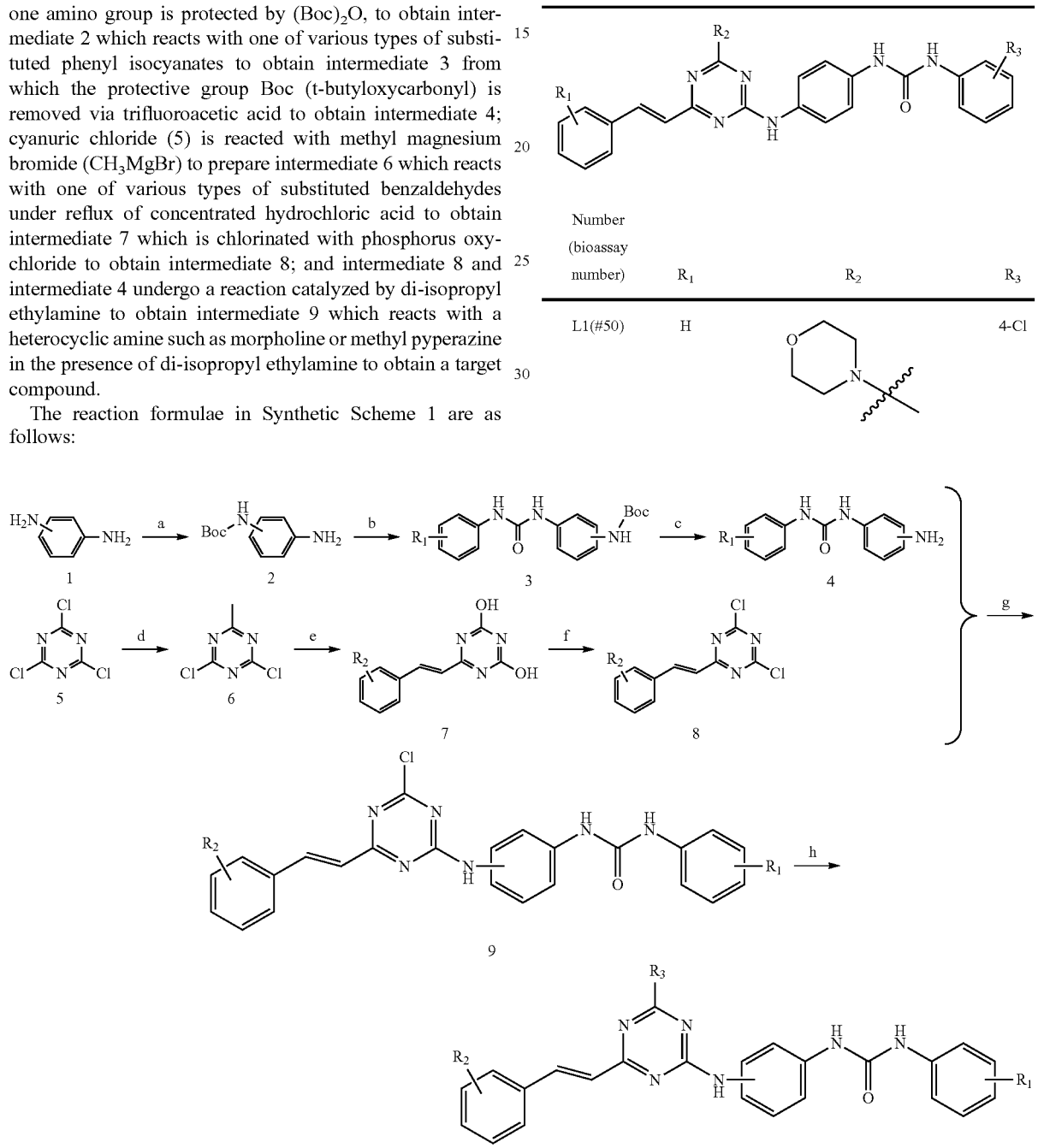

wherein $R_1$, $R_2$, $R_3$ are described above.

-continued

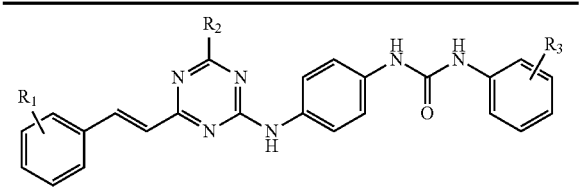

| Number (bioassay number) | $R_1$ | $R_2$ | $R_3$ |
|---|---|---|---|
| L2(#52) | H | 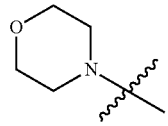 [SMILES: *N1CCOCC1] morpholine | 4-F |
| L3(#51) | H | N-methylpiperazine | 4-Cl |
| L4(#53) | H | N-methylpiperazine | 4-F |
| L5(#57) | H | 3-hydroxyazetidine | 4-Cl |
| L6(#54) | 3-Cl | morpholine | 4-Cl |
| L7(#60) | 3-Cl | morpholine | 4-F |
| L8(#55) | 3-Cl | N-methylpiperazine | 4-Cl |
| L9(#61) | 3-Cl | N-methylpiperazine | 4-F |
| L10(#43) | 4-Cl | morpholine | 4-Cl |

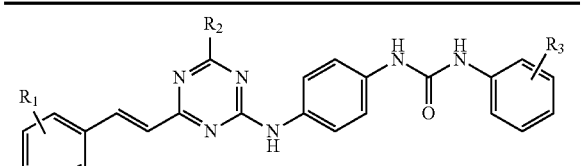

| Number (bioassay number) | $R_1$ | $R_2$ | $R_3$ |
|---|---|---|---|
| L11(#45) | 4-Cl | 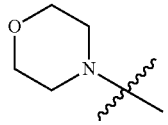 [SMILES: *N1CCOCC1] morpholine | 4-F |
| L12(#49) | 4-Cl | morpholine | 3-F |
| L13(#44) | 4-Cl | N-methylpiperazine | 4-Cl |
| L14(#42) | 4-Cl | N-methylpiperazine | 4-F |
| L15(#48) | 4-Cl | N-methylpiperazine | 3-F |
| L16(#40) | 3-$NO_2$ | morpholine | 4-Cl |
| L17(#62) | 3-$NO_2$ | morpholine | 4-F |
| L18(#41) | 3-$NO_2$ | N-methylpiperazine | 4-Cl |
| L19(#63) | 3-$NO_2$ | N-methylpiperazine | 4-F |

17
-continued

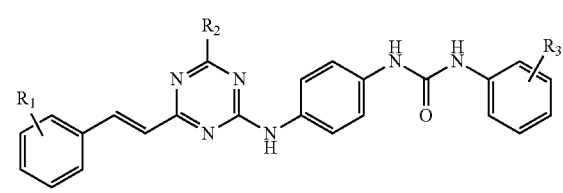

| Number (bioassay number) | R₁ | R₂ | R₃ |
|---|---|---|---|
| L20(#38) | 3-NO₂ | | 4-Cl |
| L21(#39) | 3-NO₂ | | 4-Cl |
| L22(#58) | 3-NO₂ | | 4-Cl |

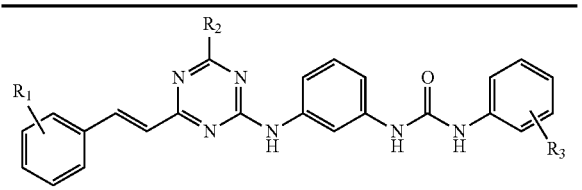

| Number (bioassay number) | R₁ | R₂ | R₃ |
|---|---|---|---|
| L23(#64) | H | | 4-Cl |
| L24(#65) | H | | 4-Cl |

18
-continued

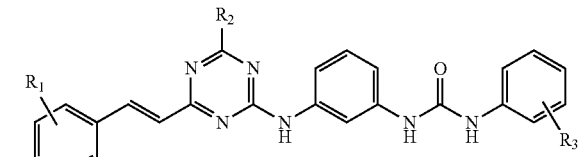

| Number (bioassay number) | R₁ | R₂ | R₃ |
|---|---|---|---|
| L25(#59) | 3-Cl | | 4-Cl |
| L26(#56) | 3-Cl | | 4-Cl |
| L27(#66) | 3-NO₂ | | 4-Cl |
| L28(#67) | 3-NO₂ | | 4-Cl |

Synthetic Scheme 2: Metaphenylene diamine or paraphenylene diamine (1) is used as a starting material, of which one amino group is protected by (Boc)₂O, to obtain intermediate 2 which reacts with methyl p-amino benzoate in the presence of triphosgene to obtain intermediate 10 from which the protective group Boc is removed via trifluoroacetic acid to obtain intermediate 11; cyanuric chloride (5) is reacted with methyl magnesium bromide to prepare intermediate 6 which reacts with one of various types of substituted benzaldehydes under reflux of concentrated hydrochloric acid to obtain intermediate 7 which is chlorinated with phosphorus oxychloride to obtain intermediate 8; and intermediate 8 and intermediate 11 undergo a reaction catalyzed by di-isopropyl ethylamine to obtain intermediate 12 which further reacts with a heterocyclic amine such as morpholine or methyl pyperazine in the presence of di-isopropyl ethylamine to obtain compound 13; compound 13 is hydrolyzed in the presence of lithium hydroxide monohydrate, acidified with hydrochloric acid to obtain intermediate 14 which finally undergoes a condensation reaction with one of various amines in the presence of catalysts HOBt (1-hydroxybenzotriazole), EDCl [1-(3-dimethylaminopropyl)-3-ethylcarbodiimide hydrochloride] to obtain a target compound.

The reaction formulae in Synthetic Scheme 2 are as follows:

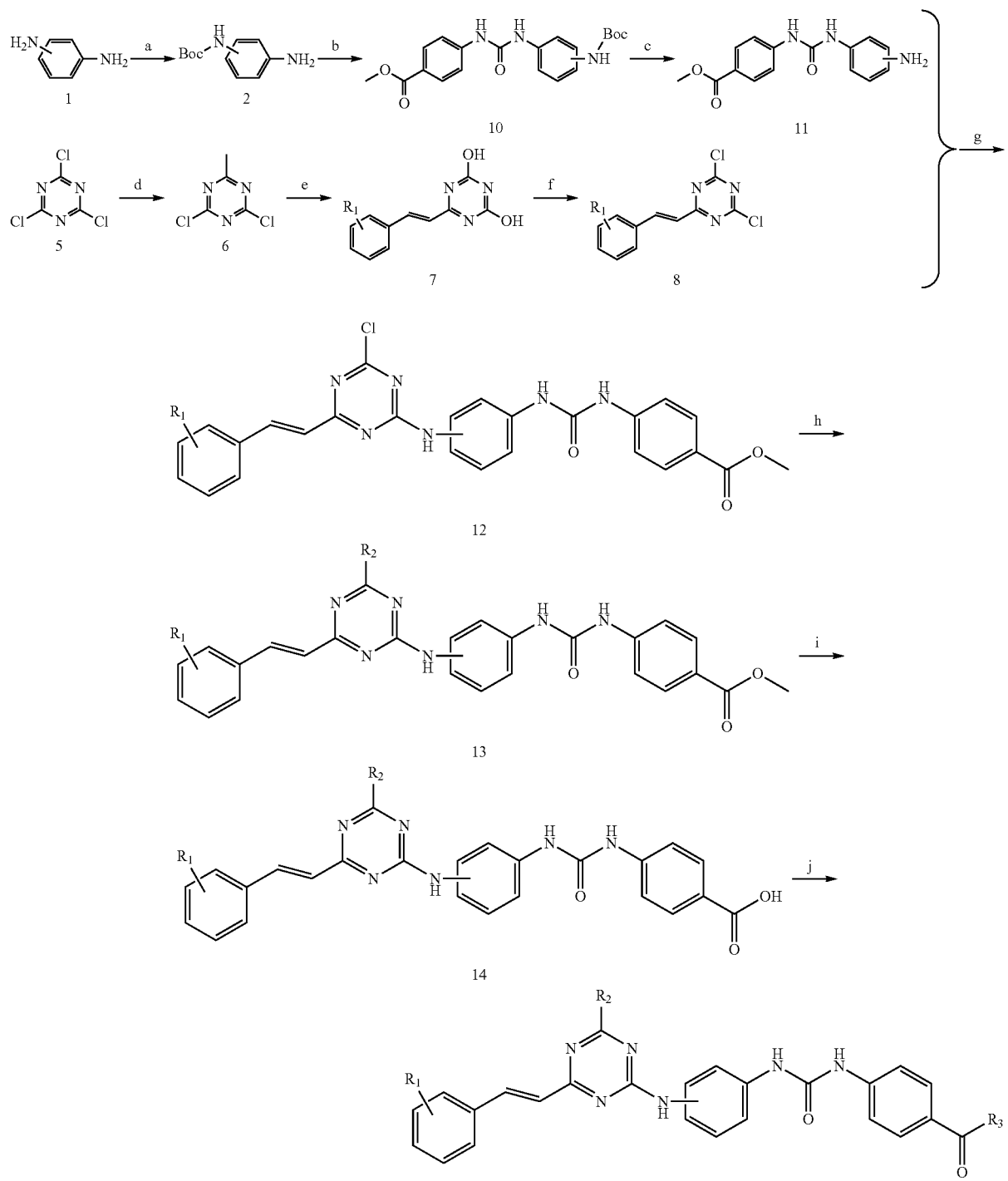

wherein $R_1$, $R_2$, $R_3$ are described above.

Reagents in the reaction formulae in the above synthetic scheme: (a) a base, preferably potassium carbonate, (Boc)$_2$O, water, tetrahydrofuran, DMF; (b) triphosgene, triethylamine, methyl p-amino benzoate, methylene dichloride; (c) trifluoroacetic acid, methylene dichloride; (d) a solution of methyl magnesium bromide in tetrahydrofuran; (e) substituted benzaldehyde, concentrated hydrochloric acid, reflux for 12 hours; (f) phosphorus oxychloride, reflux for 16 hours; (g) di-iso-propyl ethylamine, tetrahydrofuran; (h) heterocyclic amine, di-iso-propyl ethylamine, tetrahydrofuran; (i) lithium hydroxide monohydrate, tetrahydrofuran, water, concentrated hydrochloric acid; (j) HOBt, EDCI, triethylamine, substituted amine, DMF.

The structural formula of the target compound of Synthetic Scheme 2 is shown as the following example:

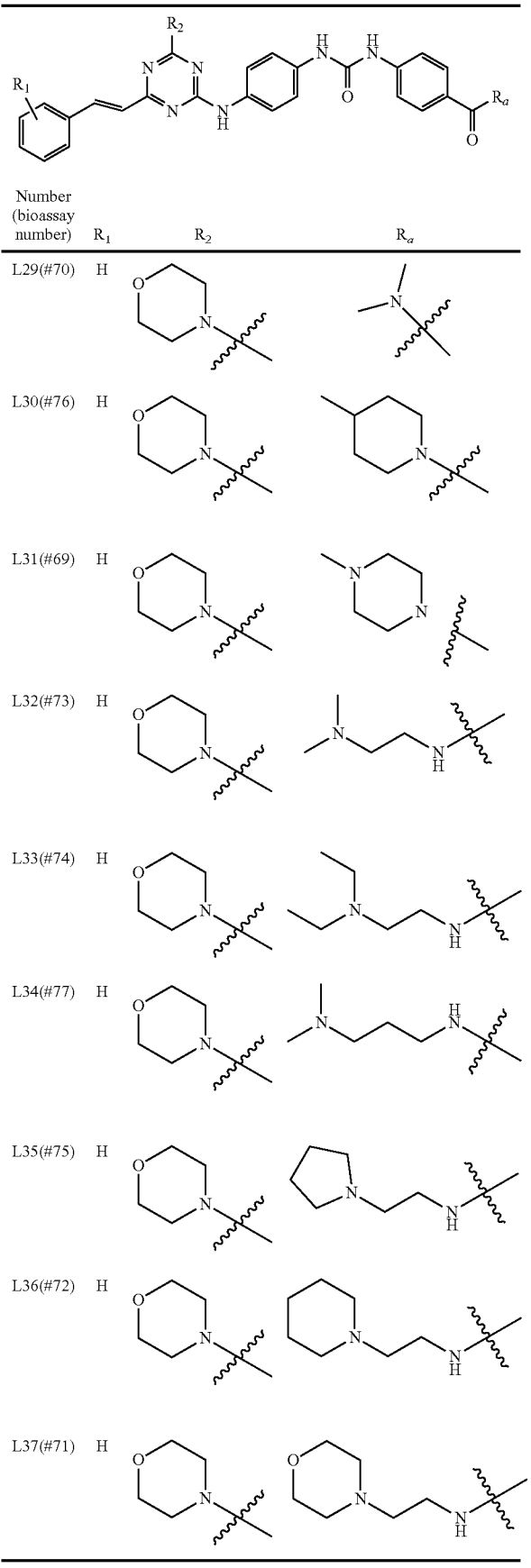

Synthetic Scheme 3: cyanuric chloride (5) is reacted with methyl magnesium bromide to prepare intermediate 6 which reacts with one of various types of substituted benzaldehydes under reflux of concentrated hydrochloric acid to obtain intermediate 7 which is chlorinated with phosphorus oxychloride to obtain intermediate 8; intermediate 8 reacts with sodium p-nitrophenol to obtain intermediate 15; intermediate 15 reacts with a heterocyclic amine such as morpholine or methyl pyperazine in the presence of catalyst di-isopropyl ethylamine to obtain compound 16. Compound 16 is reduced in a system of iron powder and ammonium chloride to obtain intermediate 17 which reacts with one of various types of substituted phenyl isocyanates to obtain a target compound.

The reaction formulae in Synthetic Scheme 3 are as follows:

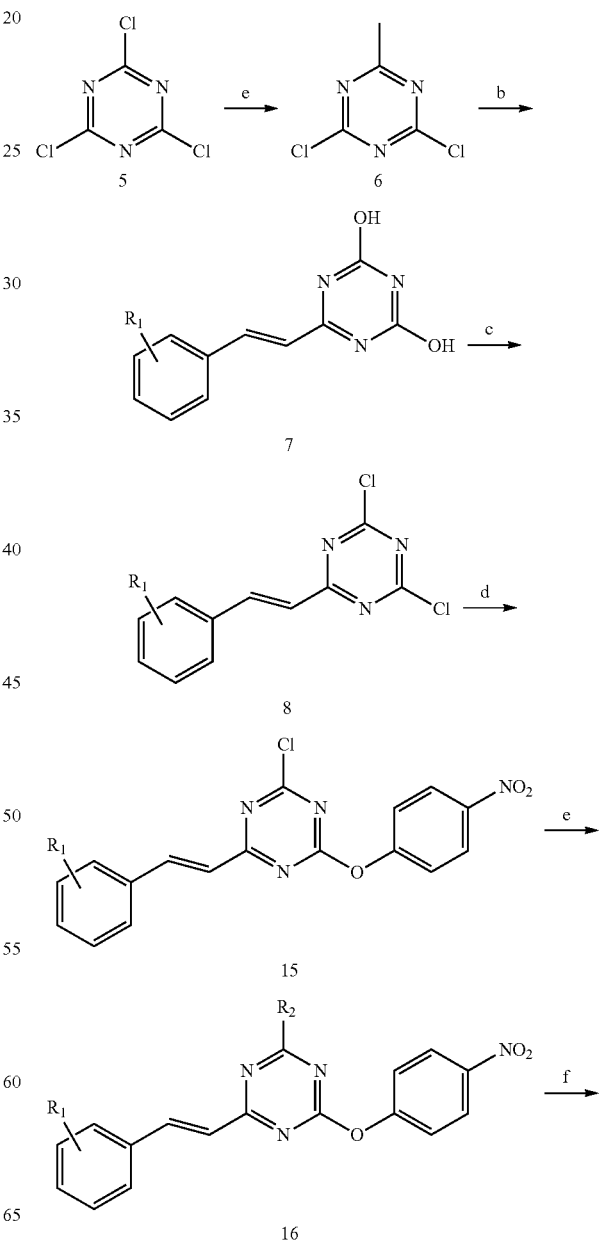

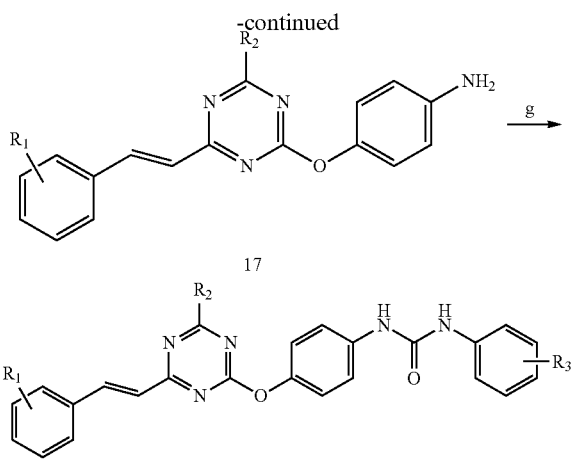

wherein $R_1$, $R_2$, $R_3$ are described above. In some embodiments, $R_1$ is hydrogen; electron withdrawing groups such as halogen, nitro, etc; electron donating groups such as alkyl, amino, hydroxyl, hydroxymethyl, aminomethyl, aminoformyl, etc; $R_2$ is amino, alkylamino, arylamino, heteroarylamino; $R_3$ is hydrogen; electron withdrawing groups such as halogen, nitro, etc; electron donating groups such as alkyl, amino, hydroxyl, hydroxymethyl, aminomethyl.

Reagents in the reaction formulae in the above synthetic scheme: (a) a solution of methyl magnesium bromide in tetrahydrofuran; (b) substituted benzaldehyde, concentrated hydrochloric acid, reflux for 12 hours; (c) phosphorus oxychloride, reflux for 16 hours; (d) water, tetrahydrofuran, sodium p-nitrophenol; (e) heterocyclic amine, di-iso-propyl ethylamine, tetrahydrofuran; (f) iron powder, ammonium chloride, ethanol, water, reflux for 3 hours; (g) substituted phenyl isocyanate, methylene dichloride.

The structural formula of the target compound of Synthetic Scheme 3 is shown as the following example:

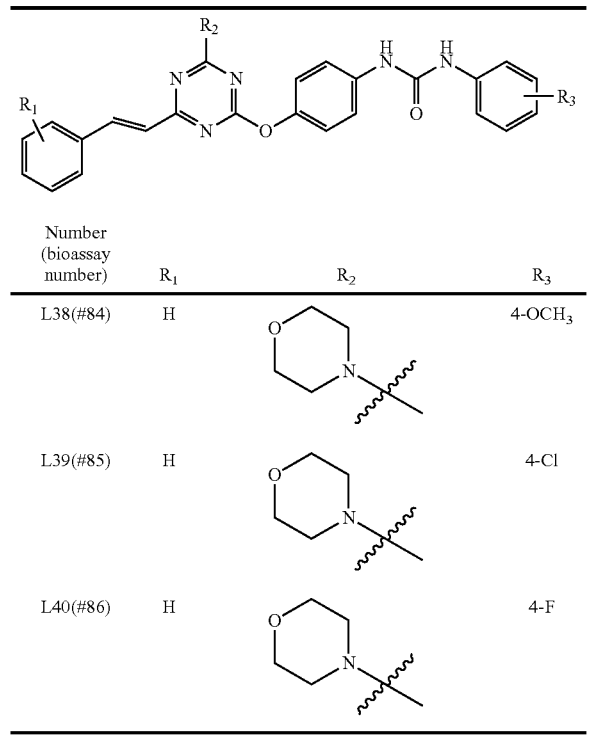

| Number (bioassay number) | $R_1$ | $R_2$ | $R_3$ |
|---|---|---|---|
| L38(#84) | H | morpholine-N-yl | 4-OCH$_3$ |
| L39(#85) | H | morpholine-N-yl | 4-Cl |
| L40(#86) | H | morpholine-N-yl | 4-F |

The specific process steps for the compounds will be described in detail in the Examples.

The above steps may be modified by those skilled in the art to increase yields. They may determine a synthetic scheme based on the basic knowledge in the art, for example, choosing reactants, solvents and temperatures, using various conventional protective groups to avoid side reactions to increase yields.

The present disclosure further includes pharmaceutically acceptable salts, prodrugs or solvates of the compound represented by Formula (I). Examples of pharmaceutically acceptable salts include inorganic and organic salts, such as hydrochloride salts, hydrobromide salts, phosphate salts, sulfate salts, citrate salts, lactate salts, tartrate salts, maleate salts, fumarate salts, mandelate salts and oxalate salts; and inorganic and organic salts formed with bases such as sodium hydroxide, tri(hydroxymethyl)amino methane (TRIS, trometamol) and N-methyl glucosamine. Examples of prodrugs include simple esters of carboxyl-containing compounds; esters of hydroxyl-containing compounds; imines of amino-containing compounds; urethanes of amino-containing compounds; acetals or ketals of alcohol-containing compounds.

The present disclosure further includes pharmaceutical compositions of pharmaceutically acceptable salts, prodrugs or solvates of the compound represented by Formula (I). The pharmaceutical compositions may further comprise various pharmaceutically acceptable carriers conventionally used for preparation of pharmaceutical compositions. As used herein, "pharmaceutically acceptable carrier" refers to an inactive component, such as a solid, semi-solid or liquid filler, a diluent, a coating material, a formulation auxiliary agent, or an excipient, used together with the compound of the disclosure to form a "pharmaceutical composition" to be administered to a subject. The pharmaceutically acceptable carrier is nontoxic to the subject of administration at the dosage and concentration used, and compatible with the other components in the formulation. The pharmaceutically acceptable carrier is appropriate for the formulation employed. For example, if a therapeutic agent is to be administered orally, the carrier may be a gel capsule. If the therapeutic agent is to be administered subcutaneously, the carrier is desirably non-irritating to skin, and does not render reaction at the injection point. The pharmaceutical composition may be any suitable form of a formulation, such as tablet, lozenge and capsule.

Generally, the pharmaceutical composition comprises a therapeutically or preventively effective amount of a pharmaceutical acceptable salt, prodrug or solvate of the compound of Formula (I) in this disclosure. As used herein, "effective amount" means an amount of the compound, or a pharmaceutically acceptable salt, prodrug or solvate thereof that allows for effective treatment or prevention in the process of treatment or prevention of a disease. The "effective amount" may be varied according to the active ingredient administered, the administration method, the disease and severity thereof, the health condition, the age, the body weight, the family history, the genetic constitution, the stage of the pathological development, the type of treatment conducted before administration and concurrently, and other individual characteristics of the subject to be treated.

The compounds disclosed herein exhibit strong inhibiting effect for a plurality of tumor cells of various types. Therefore, the compounds of Formula (I) and the compounds of Formulae (I-1), (I-2) and (I-3) may be used to prevent and treat various solid tumors and hematological tumors, including without limitation to lung cancer (e.g. non-small cell lung cancer), colon cancer, cervical cancer, liver cancer, fibrosarcoma, erythroleukemia, prostate cancer, breast cancer, pancreatic cancer, ovarian cancer, melanoma, brain glioma and the like.

Some of the compounds of the disclosure may cause non-apoptosis death of tumor cells—methuosis. This form of death is attributed to the specific bonding of this genus of compounds to a cellular intermediate filament, i.e. vimentin. Therefore, the disclosure also relates to use of the compounds disclosed by the disclosure to intervene in pathophysiological processes related with vimentin and treat diseases associated therewith, including without limitation to epithelial-mesenchymal transition; differentiation of stem cells; infiltrative growth, metastasis, drug resistance and relapse of tumors; tissue fibrosis; infectious diseases and cardiovascular diseases (e.g. atherosclerosis), etc. In some embodiments, the disclosure provides use of the compounds described herein in preparation of drugs for preventing or treating mammal diseases associated with vimentin dysregulation; formation, transportation and secretion of vesicles; and/or cell vacuolization. Further, the mammal diseases associated with vimentin dysregulation; formation, transportation and secretion of vesicles; and/or cell vacuolization include cancers, neurodegenerative diseases, tissue fibrosis and atherosclerosis. Still further, the mammal diseases associated with vimentin dysregulation; formation, transportation and secretion of vesicles; and/or cell vacuolization include various solid tumors, such as colon cancer, pancreatic cancer, ovarian cancer, gastric cancer, breast cancer, thyroid cancer, liver cancer, kidney cancer, lung cancer, prostate cancer, sarcoma, glioma, etc. and leukemia, multiple myeloma, and the like. In some embodiments, the infectious diseases described herein include but are not limited to diseases caused by virus infection, such as diseases caused by infection of hepatitis C virus, SARS virus, HIV and dengue fever virus, etc.

Therefore, in some embodiments, the disclosure provides uses of the compounds shown by Formula (I), the pharmaceutically acceptable salts, prodrugs or solvates thereof in preparation of drugs for treating or preventing tumors. In some embodiments, the disclosure provides the compounds shown by Formula (I), the pharmaceutically acceptable salts, prodrugs or solvates thereof for treating or preventing tumors. The tumors are described above.

In some embodiments, the disclosure provides uses of the compounds shown by Formula (I), the pharmaceutically acceptable salts, prodrugs or solvates thereof in preparation of drugs for intervening transportation of cellular vesicles and release thereof to outside of the cells, or preparation of drugs for promoting cell death by methuosis, or preparation of drugs for treating or preventing diseases mediated by vimentin. Alternatively, in some embodiments, the disclosure provides the compounds shown by Formula (I) herein, the pharmaceutically acceptable salts, prodrugs or solvates thereof for intervening transportation of cellular vesicles and release thereof to outside of the cells, promoting cell death by methuosis, treating or preventing diseases mediated by vimentin. Particularly, the diseases mediated by vimentin include those associated with epithelial-mesenchymal transition; differentiation of stem cells; metastasis, drug resistance and relapse of tumors; tissue fibrosis; and cardiovascular diseases (e.g. atherosclerosis). Still further, the tumors include various solid tumors such as colon cancer, pancreatic cancer, ovarian cancer, gastric cancer, breast cancer, thyroid cancer, liver cancer, kidney cancer, lung cancer, prostate cancer, sarcoma, glioma, and hematological tumors such as leukemia, multiple myeloma and the like.

In some embodiments, the disclosure further provides a method for treating or preventing tumors, including solid tumors and hematological tumors, wherein the method comprises administration of a therapeutically effective amount of a compound shown by Formula (I) herein or a pharmaceutical composition thereof. The disclosure further provides a method for intervening transportation of cellular vesicles and release thereof to outside of the cells, promoting cell death by methuosis, treating or preventing diseases mediated by vimentin, wherein the method comprises administration of a therapeutically effective amount of a compound shown by Formula (I) herein or a pharmaceutical composition thereof. The drugs may be administered through a suitable route to achieve the anticipated aim. For example, the drugs may be administered parenterally, subcutaneously, intravenously, intramuscularly, intraperitoneally, transdermally, buccally, intrathecally, encephalically, nasally or externally. A drug dosage may be determined in light of the age, health condition, body weight, parallel treatment, treatment frequency of a patient and the desired treatment efficiency.

In order to demonstrate the technical contents of the disclosure better, the disclosure will be further illustrated with reference to the following specific examples to which the disclosure is not limited. It's to be understood that the compounds of Formula (I), when mentioned, include the compounds presented by Formulae (I-1), (I-2) and (I-3) herein. Unless otherwise indicated, the methods and reagents used in the examples are conventional methods and reagents in the art.

In the following examples where compounds were synthesized, a conventional working process is addition of an appropriate amount of water to a reaction liquid after completion of a reaction, followed by separation of an organic phase and an aqueous phase, and combination of organic phases from a number of separation operations. If necessary, drying is conducted using a 5% HCl solution and/or saturated $NaSO_4$ in sequence, followed by filtration and vacuum drying to obtain a crude product which is separated and purified by column chromatography to obtain a final product.

EXAMPLE 1

Synthesis of L16

1) Preparation of 4-((t-butyloxycarbonyl)amino)aniline (2)

P-phenylenediamine (3.24 g, 30.0 mmol) and potassium carbonate (1.52 g, 11.0 mmol) were dissolved in 10 mL DMF and 5 mL water. At room temperature, a solution of $(Boc)_2O$ (2.18 g, 10.0 mmol) in tetrahydrofuran (30 mL) was added dropwise slowly. After dropping, the solution was stirred at room temperature for reaction for 4 hours. The reaction liquid was poured into 100 mL iced water, extracted with methylene dichloride (200 mL), and washed in sequence with water and saturated brine. The organic layer was dried with anhydrous sodium sulfate, and the solvent was evaporated completely, followed by silica gel column chromatography to obtain 1.79 g white solid at a yield of 86%.

2) Preparation of 1-(4-chlorophenyl)-3-(4-((t-butyloxycarbonyl)amino)phenyl)urea (3)

At room temperature, a solution of p-chlorophenyl isocyanate (461 mg, 3.0 mmol) in methylene dichloride (5 mL)

was added dropwise slowly to a solution of intermediate 2 (625 mg, 3.0 mmol) in methylene dichloride (10 mL), followed by stirring at room temperature for 5 hours after completion of dropping. The reaction liquid was suction-filtrated directly, and the filter cake was dried to obtain 977 mg white solid at a yield of 90%.

3) Preparation of 1-(4-chlorophenyl)-3-(4-aminophenyl)urea (4)

At room temperature, a solution of trifluoroacetic acid (47 mg, 4.16 mmol) in methylene dichloride (5 mL) was added dropwise slowly to a solution of intermediate 3 (188 mg, 0.52 mmol) in methylene dichloride (10 mL), followed by stirring at room temperature for 3 hours after completion of dropping. The reaction liquid was dried by rotary evaporation directly, and pH was adjusted with saturated sodium carbonate to weak alkalinity. The resultant was extracted with ethyl acetate, followed by washing in sequence with water and saturated brine.

The organic layer was dried with anhydrous sodium sulfate, and the solvent was evaporated completely to obtain 129 mg white solid at a yield of 95%. $^1$H NMR (300 MHz, DMSO): δ8.63 (s, 1H,NH); 8.16 (s, 1H,NH); 7.45 (d,2H, J=8.8 Hz); 7.29 (d,2H,J=8.8 Hz); 7.06 (d,2H,J=8.6 Hz); 6.50 (d,2H,J=8.6 Hz); 4.80 (s,2H, —NH$_2$).

4) 2-methyl-4,6-dichloro-1,3,5-triazine (6)

Under the protection of nitrogen gas at −20° C., a solution of methyl magnesium bromide in diethyl ether (3 mL, 9 mmol) was added dropwise slowly to a solution of cyanuric chloride (1.38 g, 7.5 mmol) in 8 mL tetrahydrofuran; after dropping, the mixture was stirred at ambient temperature for reaction for 2 hours; and then the reaction was stopped and quenched by addition of 20 mL saturated ammonium chloride. The reaction liquid was extracted twice with 20 mL ethyl acetate and 20 mL saturated sodium chloride; and the organic phase was dried with anhydrous sodium sulfate. After silica gel column chromatography, 615 mg white solid was obtained at a yield of 50%. $^1$H NMR (CDCl$_3$) δ:2.71 (s,3H,CH$_3$).

5) 2,4-dihydroxy-6-(3-nitrostyrenyl)-1,3,5-triazine (7)

Intermediate 6 (1.60 g, 9.76 mmol) and 3-nitrobenzaldehyde (1.47 g, 9.76 mmol) were dissolved in 30 mL concentrated hydrochloric acid, heated to 100° C., and allowed to react for 12 hours under agitation. The reaction was stopped. The reaction liquid was cooled to room temperature, poured into 60 mL iced water, suction-filtered, and washed in sequence with 10 mL ethyl acetate and 10 mL water-petroleum ether. The filter cake was dried to obtain 2.01 g white crude product at a yield of 79.2%.

6) 2,4-dichloro-6-(3-nitrostyrenyl)-1,3,5-triazine (8)

A liquid mixture of intermediate 7 (960 mg, 3.69 mmol) and phosphorus oxychloride (10 mL) was heated to 140° C. and allowed to react for 19 hours under agitation. The reaction was stopped. The reaction liquid was cooled to room temperature, and dried by rotary evaporation. The remaining part was poured into 60 mL iced water, extracted with 60 mL ethyl acetate, and washed in sequence with water and saturated brine. The organic layer was dried with anhydrous sodium sulfate, and the solvent was evaporated completely. After silica gel column chromatography, 660 mg white solid was obtained at a yield of 60.2%.

7) 1-(4-chlorophenyl)-3-(4-chloro-6-(3-nitrostyrenyl)-1,3,5-triazinyl-2-amino)phenyl)urea (9)

Under the protection of nitrogen gas, intermediate 4 (342 mg, 1.15 mmol), intermediate 8 (300 mg, 1.15 mmol) and di-isopropyl ethylamine (149 mg, 1.15 mmol) were dissolved in 50 mL tetrahydrofuran, and allowed to react for 5 hours at room temperature under agitation. After completion of the reaction, half of the solvent was removed by rotary evaporation. The remaining part was poured into 60 mL water, extracted with 120 mL ethyl acetate, and washed in sequence with water and saturated brine. The organic layer was dried with anhydrous sodium sulfate; the solvent was evaporated completely; 2 mL anhydrous ethanol was added, followed by ultrasonication for 30 seconds and suction filtration. The filter cake was dried to obtain 522 mg crude product at a yield of 86.9%.

8) 1-(4-chlorophenyl)-3-(4-(4-(morpholin-1-yl)-6-(3-nitrostyrenyl)-1,3,5-triazinyl-2-amino)phenyl)urea (L16)

Under the protection of nitrogen gas, intermediate 9 (270 mg, 0.52 mmol), morpholine (181 mg, 2.08 mmol) and di-isopropyl ethylamine (202 mg, 1.56 mmol) were dissolved in 60 mL tetrahydrofuran, and allowed to react for 4 hours at room temperature under agitation. After completion of the reaction, half of the solvent was removed by rotary evaporation. The remaining part was poured into 100 mL water, extracted with 100 mL ethyl acetate, and washed in sequence with water and saturated brine. The organic layer was dried with anhydrous sodium sulfate; the solvent was evaporated completely; 1 mL anhydrous ethanol was added, followed by ultrasonication for 30 seconds and suction filtration. The filter cake was dried to obtain 206 mg pale yellow solid at a yield of 69.0%. $^1$H NMR (300 MHz, DMSO-d6): δ 9.46 (s, 1H), 9.19 (s, 1H), 8.96 (s, 1H), 8.40 (s, 1H), 8.10 (d, J=8.0 Hz, 2H), 7.95 (d, J=15.9 Hz, 1H), 7.62 (d, J=8.0 Hz, 2H), 7.53-7.58 (m, 1H), 7.39 (d, J=8.6 Hz, 2H), 7.31 (d, J=8.6 Hz, 2H), 7.21 (d, J=8.6 Hz, 2H), 6.95 (d, J=15.9 Hz, 1H), 3.73 (m, 4H),3.59 (m, 4H) ppm. HRMS calcd for C$_{28}$H$_{26}$ClN$_8$O$_4$ [M+H]$^+$, 573.1760, found 573.1750.

EXAMPLE 2

Synthesis of L31

1) Preparation of 4-((t-butyloxycarbonyl)amino)aniline (2)

P-phenylenediamine (3.24 g, 30.0 mmol) and potassium carbonate (1.52 g, 11.0 mmol) were dissolved in 10 mL DMF and 5 mL water. At room temperature, a solution of (Boc)$_2$O (2.18 g, 10.0 mmol) in tetrahydrofuran (30 mL) was added dropwise slowly. After dropping, the solution was stirred at room temperature for reaction for 4 hours. The reaction liquid was poured into 100 mL iced water, extracted with methylene dichloride (200 mL), and washed in sequence with water and saturated brine. The organic layer was dried with anhydrous sodium sulfate, and the solvent was evaporated completely. After silica gel column chromatography, 1.79 g white solid was obtained at a yield of 86%.

2) Preparation of methyl 4-(3-(4-((t-butyloxycarbonyl)amino)phenyl)urea)benzoate (10)

In an ice bath, a solution of methyl p-aminobenzoate (500 mg, 3.3 mmol) in methylene dichloride (5 mL) was added dropwise slowly to a solution of triphosgene (980.1 mg, 3.3 mmol) in methylene dichloride (10 mL). After dropping, a solution of triethylamine (667 mg, 6.6 mmol) in methylene dichloride (5 mL) was added dropwise. After dropping, the solvent in the reaction liquid was dried by rotary evaporation. Methylene dichloride (20 mL) was added again, and intermediate 2 (618 mg, 2.97 mmol) was added, followed by agitation at room temperature for 5 hours. Saturated sodium carbonate was added to the reaction liquid to adjust pH to weak alkalinity. The reaction liquid was extracted with ethyl acetate, and washed in sequence with water and saturated brine. The organic layer was dried with anhydrous sodium sulfate. The solvent was evaporated completely. The resultant was washed with ethyl acetate/petroleum ether having a volumetric ratio=1/4, and suction-filtered. The filter cake was dried to obtain 600 mg white solid at a yield of 52.4%. $^1$H NMR (300 MHz, DMSO) δ 9.20 (s, 1H), 9.01 (s, 1H), 8.64 (s, 1H), 7.88 (d, J=8.7 Hz, 2H), 7.58 (d, J=8.7 Hz, 2H), 7.41-7.30 (m, 4H), 3.82 (s, 3H), 1.47 (s, 9H) ppm.

3) Preparation of methyl 4-(3-(4-aminophenyl)urea)benzoate (11)

At room temperature, a solution of trifluoroacetic acid (474 mg, 4.16 mmol) in methylene dichloride (5 mL) was added dropwise slowly to a solution of intermediate 10 (200 mg, 0.52 mmol) in methylene dichloride (10 mL), followed by agitation at room temperature for 3 hours after completion of the dropping. The reaction liquid was dried by rotary evaporation directly, and pH was adjusted with saturated sodium carbonate to weak alkalinity. The resultant was extracted with ethyl acetate, followed by washing in sequence with water and saturated brine. The organic layer was dried with anhydrous sodium sulfate, and the solvent was evaporated completely to obtain 141 mg white solid at a yield of 95%. $^1$H NMR (300 MHz, DMSO): δ8.63 (s, 1H); 8.16 (s, 1H); 7.45 (d, J=8.8 Hz, 2H); 7.29 (d, J=8.8 Hz, 2H); 7.06 (d, 8.6 Hz, 2H); 6.50 (d, J=8.6 Hz, 2H); 4.80 (s, 2H), 3.82 (s, 3H).

4) 2-methyl-4,6-dichloro-1,3,5-triazine (6)

Under the protection of nitrogen gas at −20° C., a solution of methyl magnesium bromide in diethyl ether (3 mL, 9 mmol) was added dropwise slowly to a solution of cyanuric chloride (1.38 g, 7.5 mmol) in 8 mL tetrahydrofuran; after dropping, the mixture was placed at ambient temperature for reaction for 2 hours under agitation; and then the reaction was stopped and quenched by addition of 20 mL saturated ammonium chloride. The reaction liquid was extracted twice with 20 mL ethyl acetate and 20 mL saturated sodium chloride; and the organic phase was dried with anhydrous sodium sulfate. After silica gel column chromatography, 615 mg white solid was obtained at a yield of 50%. $^1$H NMR (CDCl$_3$) δ:2.71 (s,3H,CH$_3$).

5) 2, 4-dihydroxy-6-styrenyl-1,3,5-triazine (7)

Intermediate 6 (1.60 g, 9.76 mmol) and benzaldehyde (1.04 g, 9.76 mmol) were dissolved in 30 mL concentrated hydrochloric acid, heated to 100° C., and allowed to react for 12 hours under agitation. The reaction was stopped. The reaction liquid was cooled to room temperature, poured into 60 mL iced water, suction-filtered, and washed in sequence with 10 mL ethyl acetate and 10 mL water-petroleum ether. The filter cake was dried to obtain 1.66 g white crude product at a yield of 79.2%.

6) 2, 4-dichloro-6-styrenyl-1,3,5-triazine (8)

A liquid mixture of intermediate 7 (794 mg, 3.69 mmol) and phosphorus oxychloride (10 mL) was heated to 140° C. and allowed to react for 19 hours under agitation. The reaction was stopped. The reaction liquid was cooled to room temperature, and dried by rotary evaporation. The remaining part was poured into 60 mL iced water, extracted with 60 mL ethyl acetate, and washed in sequence with water and saturated brine. The organic layer was dried with anhydrous sodium sulfate, and the solvent was evaporated completely. After silica gel column chromatography, 560 mg white solid was obtained at a yield of 60.2%.

7) 1-(4-(methoxycarbonyl)phenyl)-3-(4-chloro-6-styrenyl-1,3,5-triazinyl-2-amino)phenyl)urea (12)

Under the protection of nitrogen gas, intermediate 11 (441 mg, 1.75 mmol), intermediate 8 (500 mg, 1.75 mmol) and di-isopropyl ethylamine (226 mg, 1.75 mmol) were dissolved in 50 mL tetrahydrofuran, and allowed to react for 5 hours at room temperature under agitation. After completion of the reaction, half of the solvent was removed by rotary evaporation. The remaining part was poured into 60 mL water, extracted with 120 mL ethyl acetate, and washed in sequence with water and saturated brine. The organic layer was dried with anhydrous sodium sulfate; the solvent was evaporated completely; 2 mL anhydrous ethanol was added, followed by ultrasonication for 30 seconds and suction filtration. The filter cake was dried to obtain 762 mg crude product at a yield of 86.9%.

8) 1-(4-(methoxycarbonyl)phenyl)-3-(4-(4-(morpholin-1-yl))-6-styrenyl-1,3,5-triazinyl-2-amino)phenyl)urea (13)

Under the protection of nitrogen gas, intermediate 12 (840 mg, 1.68 mmol), morpholine (584 mg, 6.72 mmol) and di-isopropyl ethylamine (651 mg, 5.04 mmol) were dissolved in 60 mL tetrahydrofuran, and allowed to react for 4 hours at room temperature under agitation. After completion of the reaction, half of the solvent was removed by rotary evaporation. The remaining part was poured into 100 mL water, extracted with 100 mL ethyl acetate, and washed in sequence with water and saturated brine. The organic layer was dried with anhydrous sodium sulfate; the solvent was evaporated completely; 1 mL anhydrous ethanol was added, followed by ultrasonication for 30 seconds and suction filtration. The filter cake was dried to obtain 639 mg pale yellow solid at a yield of 69.0%. $^1$H NMR(300 MHz, DMSO) δ 9.61(s, 1H), 9.37(s, 1H), 8.98(s, 1H), 7.95(d, J=15.9 Hz, 1H), 7.89(d, J=8.7 Hz, 2H), 7.75-7.64(m, 4H), 7.60(d, J=8.7 Hz, 2H), 7.42(t, J=7.6 Hz, 5H), 6.89(d, J=15.9 Hz, 1H), 3.82(s, 7H), 3.69(s, 4H)ppm.

9) Preparation of 4-(3-(4-(4-(morpholin-1-yl)-6-styrenyl-1,3,5-triazinyl-2-amino)phenyl)urea)benzoic acid (14)

At room temperature, intermediate 13 (300 mg, 0.54 mmol) and lithium hydroxide monohydrate (68.5 mg, 1.63 mmol) were dissolved in tetrahydrofuran (10 mL), methanol (5 mL) and water (1 mL), heated to reflux, and stirred for reaction for 12 hours. After completion of the reaction, the reaction liquid was suction-filtered. pH of the filter cake was adjusted to 4 with 2 M hydrochloric acid, followed by suction filtration. The filter cake was dried, and 1 mL anhydrous ethanol was added. After ultrasonication for 30 seconds, the filter cake was suction-filtered, and dried to obtain 171 mg pale yellow solid at a yield of 59.0%. $^1$H NMR(300 MHz, DMSO) δ 12.33(s, 1H), 9.59(s, 1H), 9.41(s, 1H), 9.09(s, 1H), 7.94(d, J=15.9 Hz, 1H), 7.88(d, J=8.3 Hz, 2H), 7.77-7.63(m, 4H), 7.59(d, J=8.3 Hz, 2H), 7.51-7.36(m, 5H), 6.89(d, J=15.9 Hz, 1H), 3.83(s, 4H), 3.69(s, 4H)ppm.

10) 1-(4-((4-methylpiperazin-1-yl)formyl)phenyl)-3-(4-(4-(morpholin-1-yl)-6-styrenyl-1,3,5-triazinyl-2-amino)phenyl)urea (L31)

At room temperature, intermediate 14 (100 mg, 0.186 mmol), HOBt (32.7 mg, 0.242 mmol), DMF (2 mL), EDCI (53.5 mg, 0.279 mmol), 4-methyl piperazine (24.2 mg, 0.242 mmol) and triethylamine (37.6 mg, 0.372 mmol) were added in sequence to a 25 mL reaction flask, and stirred for reaction for 8 hours. After completion of the reaction, the reaction liquid was poured into 10 mL iced water, extracted with methylene dichloride (20 mL), and washed with water and saturated brine in sequence. The organic layer was dried with anhydrous sodium sulfate, and the solvent was evaporated completely, followed by silica gel column chromatography to obtain 87.6 mg pale yellow solid at a yield of 76%. $^1$H NMR(300 MHz, DMSO-d6): δ 9.60(s, 1H), 8.91(s, 1H), 8.67(s, 1H), 7.95(d, J=15.9 Hz, 1H), 7.65-7.72(m, 4H), 7.52(d, J=8.5 Hz, 2H), 7.41-7.43(m, 5H), 7.34(d, J=8.5 Hz, 2H), 6.89(d, J=15.9 Hz, 1H)3.83(m, 4H),3.69(m, 4H),3.50(m, 4H),2.33(m, 4H), 2.21(s, 3H)ppm. $^{13}$C NMR (75 MHz, DMSO-d6) δ: 169.98, 168.92, 164.41, 152.41, 141.17, 138.65, 135.20, 134.18, 134.09, 129.45, 128.91, 128.55, 128.18, 127.76, 127.14, 120.57, 118.71, 117.30, 65.96, 54.78, 53.58, 47.60, 45.50, 43.38. HRMS calcd for $C_{34}H_{38}N_9O_3$ [M+H]$^+$, 620.3092, found 620.3105.

EXAMPLE 3

Synthesis of L39

1) 2-methyl-4,6-dichloro-1,3,5-triazine (6)

Under the protection of nitrogen gas at −20° C., a solution of methyl magnesium bromide in diethyl ether (3 mL, 9 mmol) was added dropwise slowly to a solution of cyanuric chloride (1.38 g, 7.5 mmol) in 8 mL tetrahydrofuran; after dropping, the mixture was placed at ambient temperature for reaction for 2 hours under agitation; and then the reaction was stopped and quenched by addition of 20 mL saturated ammonium chloride. The reaction liquid was extracted twice with 20 mL ethyl acetate and 20 mL saturated sodium chloride; and the organic phase was dried with anhydrous sodium sulfate. After silica gel column chromatography, 615 mg white solid was obtained at a yield of 50%. $^1$H NMR (CDCl$_3$) δ:2.71 (s,3H,CH$_3$).

2) 2, 4-dihydroxy-6-(3-nitrostyrenyl)-1,3,5-triazine (7)

Intermediate 6 (1.60 g, 9.76 mmol) and 3-nitrobenzaldehyde (1.47 g, 9.76 mmol) were dissolved in 30 mL concentrated hydrochloric acid, heated to 100° C., and allowed to react for 12 hours under agitation. The reaction was stopped. The reaction liquid was cooled to room temperature, poured into 60 mL iced water, suction-filtered, and washed in sequence with 10 mL ethyl acetate and 10 mL water-petroleum ether. The filter cake was dried to obtain 2.01 g white crude product at a yield of 79.2%.

3) 2,4-dichloro-6-(3-nitrostyrenyl)-1,3,5-triazine (8)

A liquid mixture of intermediate 7 (960 mg, 3.69 mmol) and phosphorus oxychloride (10 mL) was heated to 140° C. and allowed to react for 19 hours under agitation. The reaction was stopped. The reaction liquid was cooled to room temperature, and dried by rotary evaporation. The remaining part was poured into 60 mL iced water, extracted with 60 mL ethyl acetate, and washed in sequence with water and saturated brine. The organic layer was dried with anhydrous sodium sulfate, and the solvent was evaporated completely. After silica gel column chromatography, 660 mg white solid was obtained at a yield of 60.2%.

4) 2-chloro-4-(4-nitrophenoxy)-6-(styrenyl)-1,3,5-triazine (15)

Under the protection of nitrogen gas, intermediate 8 (78 mg, 0.31 mmol) was dissolved in 5 mL tetrahydrofuran; and sodium p-nitrophenol (50 mg, 0.31 mmol) was dissolved in 5 mL water. The aqueous solution of sodium p-nitrophenol was added dropwise slowly to the mixed liquid of intermediate 8, and allowed to react at room temperature for 3 hours under agitation. After completion of the reaction, half of the solvent was removed by rotary evaporation. The remaining part was poured into 20 mL water, extracted with 50 mL ethyl acetate, and washed in sequence with water and saturated brine. The organic layer was dried with anhydrous sodium sulfate; the solvent was evaporated completely; 0.5 mL anhydrous ethanol was added, followed by ultrasonication for 30 seconds and suction filtration. The filter cake was dried to obtain 84 mg crude product at a yield of 76.9%.

5) 2-(morpholin-1-yl)-4-(4-nitrophenoxy)-6-(styrenyl)-1,3,5-triazine (16)

Under the protection of nitrogen gas, intermediate 15 (84 mg, 0.24 mmol), morpholine (63 mg, 0.72 mmol) and di-isopropyl ethylamine (93 mg, 0.72 mmol) were dissolved in 15 mL tetrahydrofuran, and allowed to react for 4 hours at room temperature under agitation. After completion of the reaction, half of the solvent was removed by rotary evaporation. The remaining part was poured into 30 mL water, extracted with 30 mL ethyl acetate, and washed in sequence with water and saturated brine. The organic layer was dried with anhydrous sodium sulfate; the solvent was evaporated completely; 0.5 mL anhydrous ethanol was added, followed by ultrasonication for 30 seconds and suction filtration. The filter cake was dried to obtain 84 mg pale yellow solid at a yield of 86.0%.

6) 4-(4-(morpholin-1-yl)-6-styrenyl-1,3,5-triazine-2-oxo)aniline (17)

Iron powder (100 mg, 1.79 mmol) and ammonium chloride (40 mg, 0.74 mmol) were dissolved in 10 mL aqueous ethanol solution (volumetric ratio of ethanol to water 8:2), and heated to reflux. Intermediate 16 (100 mg, 0.247 mmol) was added rapidly to the above reaction liquid, and the reaction was continued under reflux for 2 hours. After completion of the reaction, suction filtration was performed, and the ethanol in the filtrate was removed by rotary evaporation. The remaining part was poured into 30 mL water, extracted with 30 mL ethyl acetate, and washed in sequence with water and saturated brine. The organic phase was collected and dried with anhydrous sodium sulfate. Preparation of sand was performed, followed by chromatography, wherein the eluant was petroleum ether: ethyl acetate=3:1.85 mg pure product was obtained at a yield of 91.5%. $^1$H NMR(300 MHz, DMSO): δ 7.95(d, J=15.9 Hz, 1H), 7.73(d, J=7.6 Hz, 2H), 7.43-7.41(m, 3H), 6.92(d, J=15.9 Hz, 1H), 6.87(d, J=8.7 Hz, 2H), 6.58(d, J=8.7 Hz, 2H), 5.04(s, 2H), 3.87(s, 2H), 3.66-3.60(m, 4H) ppm.

7) (E)-1-(4-chlorophenyl)-3-(4-((4-(morpholin-1-yl)-6-styrenyl-1,3,5-triazin-2-yl)oxo)phenyl)urea (L39)

At room temperature, a solution of p-chlorophenyl isocyanate (37.8 mg, 0.346 mmol) in methylene dichloride (3 mL) was added dropwise slowly to a solution of intermediate 17 (92.5 mg, 0.246 mmol) in methylene dichloride (5 mL), followed by agitation at room temperature for 5 hours after completion of dropping. The reaction liquid was suction-filtrated directly, and the filter cake was dried to obtain 117 mg white solid at a yield of 90%. $^1$H NMR(300 MHz, DMSO-d6): δ 8.86(s, 1H), 8.80(s, 1H), 7.96(d, J=15.9 Hz, 1H), 7.73-7.11(m, 2H), 7.52-7.45(m, 4H), 7.42-7.40(m, 3H), 7.34(d, J=8.7 Hz, 2H), 7.17(d, J=8.7 Hz, 2H), 6.93(d, J=15.9 Hz, 1H), 3.89(s, 2H), 3.67(s, 2H), 3.60(s, 4H) ppm.

EXAMPLE 4

Preparation of Compounds L1-L15, L17-L30, L32-L38 and L40

Compounds L1-L15 and L17-L28 were prepared using the same method and corresponding materials as in Example 1; compounds L29-L30 and L32-L37 were prepared using the same method and corresponding materials as in Example 2; and compounds L38 and L40 were prepared using the same method and corresponding materials as in Example 3. Related data for the resulting compounds are shown as follows:

L1 (#50):
$^1$H NMR (300 MHz, DMSO-d6)δ: 9.57 (s, 1H), 8.88 (s, 1H), 8.59(s, 1H), 7.93(d, J=15.9 Hz, 1H), 7.70 (d, J=8.7 Hz, 2H), 7.65 (d, J=8.7 Hz, 2H), 7.49 (d, J=8.7 Hz, 2H), 7.43-7.38(m, 5H), 7.32 (d, J=8.7 Hz, 2H), 6.88(d, J=15.9 Hz, 1H), 3.82 (m, 4H), 3.68 (m, 4H) ppm. $^{13}$C NMR (75 MHz, DMSO-d6) δ:169.99, 164.43, 163.80, 152.46, 138.83, 138.63, 135.22, 134.17, 134.11, 129.44, 128.90, 128.55, 127.76, 127.16, 125.13, 120.58, 119.58, 118.75, 65.96, 43.37. HRMS calcd for $C_{28}H_{27}ClN_7O_2$ [M+H]$^+$, 528.1909; found 528.1918.

L2 (#52):
$^1$H NMR (300 MHz, DMSO-d6)δ: 9.65 (s, 1H), 8.78 (s, 1H), 8.66(s, 1H), 7.95(d, J=15.9 Hz, 1H), 7.71 (d, J=6.6 Hz, 2H), 7.62 (d, J=8.5 Hz, 2H), 7.48-7.38(m, 7H), 7.11 (t, J=8.5 Hz, 2H), 6.90(d, J=15.9 Hz, 1H), 3.82 (m, 4H),3.69 (m, 4H) ppm. HRMS calcd for $C_{28}H_{27}FN_7O_2$ [M+H]$^+$, 512.2205, found 512.2215.

L3 (#51)
$^1$H NMR (300 MHz, DMSO-d6)δ: 9.53 (s, 1H), 8.80 (s, 1H), 8.61(s, 1H), 7.93(d, J=15.9 Hz, 1H), 7.71 (d, J=8.7 Hz, 2H), 7.66 (d, J=8.7 Hz, 2H), 7.50 (d, J=8.7 Hz, 2H), 7.44-7.39(m, 5H), 7.32 (d, J=8.7 Hz, 2H), 6.88(d, J=15.9 Hz, 1H), 3.83 (m, 4H), 2.39 (m, 4H), 2.23(s, 3H) ppm. $^{13}$C-NMR (75 MHz, DMSO-d6)δ: 169.99, 164.28, 163.80, 152.47, 138.83, 138.51, 135.24, 134.25, 134.05, 129.40, 128.89, 128.55, 127.75, 127.27, 125.12, 120.52, 119.57, 118.76, 54.34, 45.74, 42.73. HRMS calcd for $C_{29}H_{30}ClN_8O$ [M+H]$^+$,541.2175,found 541.2190.

L4 (#53):
$^1$H NMR (300 MHz, DMSO-d6)δ: 9.55 (s, 1H), 8.69 (s, 1H), 8.56(s, 1H), 7.92(d, J=15.9 Hz, 1H), 7.70 (d, J=6.6 Hz, 2H), 7.64 (d, J=8.5 Hz, 2H), 7.48-7.38(m, 7H), 7.12 (t, J=8.5 Hz, 2H), 6.88(d, J=15.9 Hz, 1H), 3.83 (m, 4H), 2.39 (m, 4H), 2.23(s, 3H) ppm. HRMS calcd for $C_{29}H_{30}FN_8O$ [M+H]$^+$,525.2521,found 525.2534.

L5 (#57):
$^1$H NMR (300 MHz, DMSO-d6)δ: 9.56 (s, 1H), 8.87 (s, 1H), 8.68(s, 1H), 8.50(s, 1H), 8.22 (d, J=8.0 Hz, 2H), 7.98(d, J=15.9 Hz, 1H), 7.74-7.69(m, 3H), 7.49 (d, J=8.0 Hz, 2H), 7.39 (d, J=8.7 Hz, 2H), 7.32 (d, J=8.7 Hz, 2H), 7.08(d, J=15.9 Hz, 1H), 5.78 (d, J=6.6 Hz, 1H), 4.61-4.59 (m, 1H), 4.37-4.32 (m, 2H), 3.90-3.86 (m, 2H) ppm. $^{13}$C-NMR (75 MHz, DMSO-d6)δ: 169.8, 165.4, 163.5, 152.5, 138.6, 135.2, 134.4, 133.9, 129.4, 128.9, 128.6, 127.8, 127.2, 125.1, 120.3, 119.5, 118.7, 60.9, 59.2. HRMS calcd for $C_{27}H_{25}ClN_7O_2$ [M+H]$^+$,514.1753, found 514.1765.

L6 (#54):
$^1$H NMR (300 MHz, DMSO-d6)δ: 9.56 (s, 1H), 8.81 (s, 1H), 8.62 (s, 1H), 7.90 (d, J=15.9 Hz, 1H), 7.83 (s, 1H), 7.66 (d, J=9.0 Hz, 3H), 7.50 (d, J=8.8 Hz, 2H), 7.43 (dd, J=13.2, 6.6 Hz, 4H), 7.33 (d, J=8.8 Hz, 2H), 6.96 (d, J=15.9 Hz, 1H), 3.82 (m, 4H),3.69 (m, 4H) ppm. HRMS calcd for $C_{28}H_{26}Cl_2N_7O_2$ [M+H]$^+$, 562.1520, found 562.1505.

L7 (#60):
$^1$H NMR (300 MHz, DMSO-d6)δ: 9.56 (s, 1H), 8.83 (s, 1H), 8.70(s, 1H), 7.91(d, J=15.9 Hz, 1H) 7.81 (s, 1H), 7.63-7.69(m, 3H), 7.44-7.49(m, 4H), 7.40 (d, J=8.8 Hz, 2H), 7.12 (t, J=8.8 Hz, 2H), 6.95(d, J=15.9 Hz, 1H), 3.82(m, 4H),3.69(m, 4H) ppm. $^{13}$C NMR (75 MHz, DMSO-d6)δ: 169.74, 164.37, 163.83, 158.75, 155.60, 152.72, 137.54, 137.07, 136.23, 134.43, 133.91, 133.72, 130.63, 129.00, 127.36, 126.32, 120.67, 119.72, 119.62, 118.55, 115.33, 115.03, 65.95, 43.35. HRMS calcd for $C_{28}H_{26}Cl FN_7O_2$ [M+H]$^+$, 546.1815, found 546.1821.

L8 (#55):
$^1$H NMR (300 MHz, DMSO-d6)δ: 9.56 (s, 1H), 8.81 (s, 1H), 8.62 (s, 1H), 7.90 (d, J=15.9 Hz, 1H), 7.83 (s, 1H), 7.66 (d, J=9.0 Hz, 3H), 7.50 (d, J=8.8 Hz, 2H), 7.43 (dd, J=13.2, 6.6 Hz, 4H), 7.33 (d, J=8.8 Hz, 2H), 6.96 (d, J=15.9 Hz, 1H), 3.84 (m, 4H), 2.39 (m, 4H), 2.23 (s, 3H). $^{13}$C-NMR (75 MHz, DMSO-d6)δ:169.75, 164.23, 163.84, 152.47, 138.83, 137.57, 136.96, 134.19, 134.10, 133.71, 130.63, 128.98, 128.55, 127.37, 127.31, 125.13, 120.59, 119.59, 118.78, 54.34, 45.73, 42.74. HRMS calcd for $C_{29}H_{29}Cl_2N_8O$ [M+H]$^+$, 575.1836, found 575.1840.

L9 (#61):
$^1$H NMR (300 MHz, DMSO-d6)δ: 9.50 (s, 1H), 8.67 (s, 1H), 8.55 (s, 1H), 7.89(d, J=15.9 Hz, 1H) 7.82 (s, 1H), 7.63-7.69(m, 3H), 7.44-7.49(m, 4H), 7.39 (d, J=8.8 Hz, 2H), 7.12 (t, J=8.8 Hz, 2H), 6.95(d, J=15.9 Hz, 1H), 3.84(m, 4H),2.39 (m, 4H), 2.23(s, 3H)ppm. $^{13}$C-NMR (75 MHz, DMSO-d6)δ: 169.7, 164.2, 163.8, 158.8, 155.6, 152.8, 137.5, 136.9, 134.3, 133.7, 130.6, 129.0, 127.4, 126.3, 120.6, 119.8, 119.7, 118.6, 115.4, 115.1, 54.3, 45.7, 42.7. HRMS calcd for $C_{29}H_{29}Cl FN_8O$ [M+H]$^+$, 559.2131, found 559.2144.

L10 (#43):
$^1$H NMR (300 MHz, DMSO-d6)δ: 10.46 (s, 1H), 10.22 (s, 1H), 9.52(s, 1H), 7.90(d, J=15.9 Hz, 1H),7.75 (d, J=8.0 Hz, 2H), 7.53-7.61(m, 4H), 7.44-7.52(m, 4H), 7.28 (d, J=8.8 Hz,

1H), 6.89(d, J=15.9 Hz, 1H), 3.83(m, 4H), 3.68 (m, 4H) ppm. HRMS calcd for $C_{28}H_{26}Cl_2N_7O_2$ [M+H]$^+$, 562.152, found 562.1517.

L11 (#45):
$^1$H NMR (300 MHz, DMSO-d6)δ: 9.6(s, 1H), 8.66(s, 1H), 8.54(s, 1H), 7.88(d, J=15.9 Hz, 1H),7.75 (d, J=8.4 Hz, 2H), 7.63 (d, J=8.4 Hz, 1H), 7.43-7.49(m, 4H), 7.38 (d, J=8.8 Hz, 2H), 7.11 (t, J=8.8 Hz, 1H),6.89(d, J=15.9 Hz, 1H), 3.82(m, 4H), 3.68 (m, 4H) ppm. HRMS calcd for $C_{28}H_{26}Cl FN_7O_2$ [M+H]$^+$, 546.1815, found 546.1822.

L12 (#49):
$^1$H NMR (300 MHz, DMSO-d6)δ: 9.60(s, 1H), 8.86 (s, 1H), 8.62(s, 1H), 7.91(d, J=15.9 Hz, 1H), 7.75 (d, J=8.0 Hz, 2H), 7.53-7.58(m, 1H), 7.39 (d, J=8.6 Hz, 2H), 7.31 (d, J=8.6 Hz, 2H), 7.21 (d, J=8.6 Hz, 2H), 6.95 (d, J=15.9 Hz, 1H), 3.73 (m, 4H),3.59 (m, 4H) ppm. $^{13}$C NMR (75 MHz, DMSO-d6)δ: 169.8, 164.0, 152.4, 141.8, 141.6, 137.3, 134.2, 134.0, 133.9, 130.3, 130.2, 129.5, 128.9, 120.6, 118.8, 113.7, 108.0, 107.8, 104.8, 104.5, 65.9, 43.3. HRMS calcd for $C_{28}H_{26}ClFN_7O_2$ [M+H]$^+$, 546.1815, found 546.1823.

L13 (#44):
$^1$H NMR (300 MHz, DMSO-d6)δ: 9.50 (s, 1H), 8.84 (s, 1H), 8.64 (s, 1H), 7.89(d, J=15.9 Hz, 1H),7.75 (d, J=8.6 Hz, 2H), 7.64 (d, J=8.6 Hz, 2H), 7.46-7.50(m, 4H), 7.39 (d, J=8.9 Hz, 2H), 7.32 (d, J=8.9 Hz, 1H), 6.91(d, J=15.9 Hz, 1H), 3.83(m, 4H), 2.38 (m, 4H), 2.23 (s, 3H) ppm. $^{13}$C NMR (75 MHz, DMSO-d6)δ: 169.9, 164.5, 163.8, 152.5, 138.9, 137.1, 134.2, 133.8, 129.5, 128.9, 128.6, 128.1, 125.1, 120.5, 119.5, 118.7, 54.3, 45.7, 42.7. HRMS calcd for $C_{29}H_{29}Cl_2N_8O$ [M+H]$^+$, 575.1836, found 575.1837.

L14 (#42):
$^1$H NMR (300 MHz, DMSO-d6)δ: 9.51 (s, 1H), 8.88 (s, 1H), 8.66 (s, 1H), 7.89(d, J=15.9 Hz, 1H),7.78 (d, J=8.6 Hz, 2H), 7.64 (d, J=8.6 Hz, 2H), 7.51-7.47(m, 4H), 7.39 (d, J=8.9 Hz, 2H), 7.32 (d, J=8.9 Hz, 1H), 6.91(d, J=15.9 Hz, 1H), 3.85(m, 4H), 2.38 (m, 4H), 2.25 (s, 3H) ppm. HRMS calcd for $C_{29}H_{29}Cl FN_8O$ [M+H]$^+$, 559.2131, found 559.2134.

L15 (#48):
$^1$H NMR (300 MHz, DMSO-d6)δ: 9.61 (s, 1H), 9.37 (s, 1H), 8.98 (s, 1H), 7.95(d, J=15.9 Hz, 1H), 7.89 (d, J=8.8 Hz, 2H), 7.66-7.72(m, 4H), 7.60 (d, J=8.8 Hz, 2H), 7.39-7.44(m, 4H), 6.89(d, J=15.9 Hz, 1H), 3.82(m, 4H), 3.82(s, 4H), 3.69 (m, 4H)ppm. $^{13}$C-NMR (75 MHz, DMSO-d6)δ: 164.2, 163.8, 160.8, 152.4, 141.7, 137.2, 134.2, 134.0, 133.8, 130.3, 130.2, 129.5, 118.7, 113.7, 107.7, 104.8, 104.4, 54.0, 45.3, 42.3. HRMS calcd for $C_{29}H_{29}ClFN_8O$ [M+H]$^+$, 559.2131, found 559.2136.

L17 (#62):
$^1$H NMR (300 MHz, DMSO-d6)δ: 9.58 (s, 1H), 8.84 (s, 1H), 8.72 (s, 1H), 8.52 (s, 1H), 8.22 (d, J=8.0 Hz, 2H),8.06 (d, J=15.9 Hz, 1H), 7.74(d, J=8.0 Hz, 1H), 7.63-7.69(m, 2H), 7.44-7.49(m, 2H),7.40 (d, J=8.8 Hz, 2H), 7.13 (d, J=8.8 Hz, 2H),7.07 (d, J=15.9 Hz, 1H), 3.84(m, 4H),3.70 (m, 4H) ppm. $^{13}$C NMR (75 MHz, DMSO-d6): 164.33, 163.86, 158.69, 152.79, 148.33, 137.14, 136.31, 134.58, 133.76, 133.56, 130.31, 130.13, 123.60, 122.39, 120.71, 119.57, 119.46, 118.39, 115.32, 115.03, 65.96, 43.36. HRMS calcd for $C_{28}H_{26}FN_8O_4$ [M+H]$^+$, 557.2056, found 557.2060.

L18 (#41):
$^1$H NMR (300 MHz, DMSO-d6)δ: 9.53 (s, 1H), 8.84 (s, 1H), 8.66(s, 1H), 8.50 (s, 1H), 8.20 (d, J=7.6 Hz, 2H),8.03(d, J=15.9 Hz, 1H), 7.73-7.64(m, 3H), 7.50 (d, J=8.5 Hz, 2H), 7.41 (d, J=8.5 Hz, 2H), 7.31 (d, J=8.5 Hz, 2H), 7.05 (d, J=15.9 Hz, 1H), 3.84 (m, 4H),2.39 (m, 4H), 2.23(s, 3H) ppm. $^{13}$C NMR (75 MHz, DMSO-d6)δ: 169.53, 164.18, 163.86, 152.48, 148.31, 138.85, 137.15, 136.20, 134.16, 133.55, 130.28, 128.53, 125.09, 123.58, 122.37, 120.60, 119.56, 118.74, 54.33, 45.72, 42.72. HRMS calcd for $C_{29}H_{29}ClN_9O_3$ [M+H]$^+$, 586.2076,found 586.2082.

L19 (#63):
$^1$H NMR (300 MHz, DMSO-d6)δ: 9.52 (s, 1H), 8.67 (s, 1H), 8.55 (s, 1H), 8.51 (s, 1H), 8.22 (d, J=8.0 Hz, 2H), 8.04(d, J=15.9 Hz, 1H), 7.73(d, J=8.0 Hz, 1H), 7.64-7.69(m, 2H), 7.44-7.49(m, 2H), 7.40 (d, J=8.8 Hz, 2H), 7.13 (d, J=8.8 Hz, 2H),7.06 (d, J=15.9 Hz, 1H), 3.85(m, 4H),2.40 (m, 4H), 2.24(s, 3H) ppm. $^{13}$C NMR (75 MHz, DMSO-d6)δ: 169.6, 164.2, 158.8, 152.7, 148.3, 137.2, 136.2, 134.3, 134.0, 133.6, 130.3, 123.6, 122.4, 120.6, 119.8, 119.7, 118.7, 115.4, 115.1, 54.4, 45.7, 42.7. HRMS calcd for $C_{29}H_{29}FN_9O_3$ [M+H]$^+$, 570.2372, found 570.2384.

L20 (#38):
$^1$H NMR (300 MHz, DMSO-d6)δ:9.50 (s, 1H), 8.81 (s, 1H), 8.62(s, 1H), 8.50 (s, 1H), 8.21 (dd, J=8.0 Hz, J=1.8 Hz, 2H),8.03(d, J=15.9 Hz, 1H), 7.74-7.69(m, 3H), 7.49 (d, J=8.9 Hz, 2H), 7.40 (d, J=8.9 Hz, 2H), 7.32 (d, J=8.5 Hz, 2H), 7.06 (d, J=15.9 Hz, 1H), 3.23-3.17 (m, 6H) ppm. $^{13}$C NMR (75 MHz, DMSO-d6)δ: 169.19, 164.90, 163.64, 152.48, 148.35, 138.86, 137.19, 135.97, 134.36, 133.98, 133.59, 130.32, 128.55, 125.09, 123.56, 122.29, 120.41, 119.56, 118.74, 35.86. HRMS calcd for $C_{28}H_{24}ClN_8O_3$ [M+H]$^+$, 531.1654, found 531.1667.

L21(#39):
$^1$H NMR (300 MHz, DMSO-d6)δ: 9.49 (s, 1H), 8.79 (s, 1H), 8.59(s, 1H), 8.49 (s, 1H), 8.21 (dd, J=8.0 Hz, J=1.8 Hz, 2H), 8.01(d, J=15.9 Hz, 1H), 7.77-7.69(m, 3H), 7.49 (d, J=8.9 Hz, 2H), 7.39 (d, J=8.9 Hz, 2H), 7.32 (d, J=8.5 Hz, 2H), 7.06 (d, J=15.9 Hz, 1H), 3.62-3.57 (m, 4H), 1.96-1.94 (m, 4H) ppm. $^{13}$C NMR (75 MHz, DMSO-d6) δ: 162.87, 152.47, 148.35, 138.85, 137.19, 134.55, 133.83, 133.61, 130.33, 128.55, 125.09, 123.55, 122.24, 120.21, 119.55, 118.75, 45.99, 24.76. HRMS calcd for $C_{28}H_{26}ClN_8O_3$ [M+H]$^+$, 557.1811, found 557.1816.

L22(#58):
$^1$H NMR (300 MHz, DMSO-d6)δ: 9.56 (s, 1H), 8.88 (s, 1H), 8.69(s, 1H), 8.50 (s, 1H), 8.22 (d, J=8.0 Hz, 2H),7.98(d, J=15.9 Hz, 1H), 7.68-7.74(m, 3H), 7.49 (d, J=8.8 Hz, 2H), 7.39 (d, J=8.8 Hz, 2H), 7.32 (d, J=8.8 Hz, 2H),7.08 (d, J=15.9 Hz, 1H), 5.78 (d, J=6.6 Hz, 1H),4.58-4.61(m, 1H), 4.32-4.37 (m, 2H), 3.86-3.90(m, 2H) ppm. $^{13}$C NMR (75 MHz, DMSO-d6)δ: 169.36, 165.26, 163.55, 152.51, 148.31, 138.88, 137.09, 136.14, 134.29, 134.05, 133.65, 130.27, 128.54, 125.06, 123.57, 122.25, 120.42, 119.49, 118.67, 60.93, 59.23. HRMS calcd for $C_{27}H_{24}ClN_8O_4$ [M+H]$^+$, 559.1604, found 559.1609.

L23 (#64):
$^1$H NMR (300 MHz, DMSO-d6)δ: 9.63 (s, 1H), 8.81(s, 1H), 8.70 (s, 1H), 8.32 (s, 1H) 8.01 (d, J=15.9 Hz, 1H), 7.69-7.71(m, 2H), 7.49 (d, J=8.8 Hz, 2H), 7.39(m, 3H), 7.33 (d, J=8.8 Hz, 2H), 7.25-7.16(m, 2H), 6.93 (m, 1H), 6.89 (d, J=15.9 Hz, 1H), 3.87 (m, 4H), 3.69(m, 4H) ppm. $^{13}$C NMR (75 MHz, DMSO-d6) δ: 170.09, 164.44, 163.90, 152.30, 140.28, 139.66, 138.92, 138.71, 135.25, 129.42, 128.85, 128.55, 127.77, 127.06, 125.28, 119.68, 113.68, 112.19, 109.91, 66.03, 43.41. HRMS calcd for $C_{28}H_{27}ClN_7O_2$ [M+H]$^+$,528.1909,found 528.1916.

L24(#65):
$^1$H NMR (300 MHz, DMSO-d6)δ: 9.58 (s, 1H), 8.90 (s, 1H), 8.76 (s, 1H), 8.34 (s, 1H) 8.00 (d, J=15.9 Hz, 1H), 7.69-7.71(m, 2H) 7.50 (d, J=8.8 Hz, 2H) 7.38 (m, 3H) 7.32 (d, J=8.8 Hz, 2H) 7.18-7.21(m, 2H), 6.94(m, 1H), 6.89 (d, J=15.9 Hz, 1H), 3.87 (m, 4H),2.39 (m, 4H), 2.23 (s, 3H) ppm. $^{13}$C-NMR (75 MHz, DMSO-d6)δ: 170.1, 164.3, 163.9, 152.3, 140.3, 139.7, 138.8, 135.3, 129.4, 128.8, 128.6, 128.5, 127.8, 127.1, 125.2, 119.6, 113.6, 112.1, 109.9, 54.5, 45.8, 42.8. HRMS calcd for $C_{29}H_{30}ClN_8O$ [M+H]$^+$, 541.2226, found 541.2236.

L25(#59):
$^1$H NMR (300 MHz, DMSO-d6)δ: 9.64 (s, 1H), 8.82(s, 1H), 8.71 (s, 1H), 8.31 (s, 1H) 7.98 (d, J=15.9 Hz, 1H), 7.80 (s, 1H), 7.68(d, J=7.0 Hz, 1H), 7.43-7.50(m, 4H), 7.32 (d, J=8.8 Hz, 2H), 7.16-7.26(m, 2H), 6.96 (d, J=15.9 Hz, 1H), 6.94 (d, J=7.0 Hz, 1H), 3.88 (m, 4H), 3.69 (m, 4H) ppm. $^{13}$C NMR (75 MHz, DMSO-d6)δ: 169.84, 164.38, 163.91, 152.30, 140.20, 139.67, 138.72, 137.55, 137.36, 133.71, 130.57, 129.01, 128.76, 128.61, 128.53, 127.32, 126.37, 125.25, 119.62, 113.72, 112.23, 109.94, 66.02, 43.40. HRMS calcd for $C_{28}H_{26}Cl_2N_7O_2$ [M+H]$^+$, 562.1520, found 562.1530.

L26(#56):
$^1$H NMR (300 MHz, DMSO-d6)δ: 9.62 (s, 1H), 8.83 (s, 1H), 8.72 (s, 1H), 8.52(s, 1H) 8.34 (s, 1H) 8.22 (d, J=8.0 Hz, 2H), 8.12 (d, J=15.9 Hz, 1H), 7.67(t, J=7.0 Hz, 1H), 7.50 (d, J=8.0 Hz, 2H), 7.17-7.34(m, 4H), 7.06 (d, J=15.9 Hz, 1H), 6.94 (t, J=7.0 Hz, 1H), 3.91 (m, 4H),2.41 (m, 4H), 2.25(s, 3H)ppm. $^{13}$C NMR (75 MHz, DMSO-d6)δ: 169.8, 164.2, 163.9, 152.3, 140.3, 139.7, 138.7, 137.6, 137.2, 133.7, 130.6, 129.0, 128.9, 128.6, 127.3, 126.4, 125.3, 119.6, 113.7, 112.2, 109.9, 54.5, 45.8, 42.8. HRMS calcd for $C_{29}H_{29}Cl_2N_8O$ [M+H]$^+$, 575.1836, found 575.1842.

L27(#66):
$^1$H NMR (300 MHz, DMSO-d6)δ: 9.62 (s, 1H), 8.83(s, 1H), 8.72 (s, 1H), 8.47 (s, 1H) 8.30 (s, 1H) 8.18 (d, J=8.0 Hz, 2H), 8.11 (d, J=15.9 Hz, 1H), 7.65(t, J=7.0 Hz, 1H) 7.45 (d, J=8.0 Hz, 2H), 7.14-7.32(m, 4H), 7.05 (d, J=15.9 Hz, 1H), 6.93 (t, J=7.0 Hz, 1H), 3.87 (m, 4H),3.67(m, 4H) ppm. $^{13}$C-NMR (75 MHz, DMSO-d6)δ:169.63, 164.37, 163.94, 152.32, 148.28, 140.18, 139.95, 139.70, 138.72, 137.13, 136.59, 133.59, 130.21, 129.96, 128.60, 128.49, 125.24, 123.56, 122.31, 119.59, 113.72, 112.22, 109.91, 66.03, 43.42, 30.37. HRMS calcd for $C_{28}H_{26}Cl_2N_8O_4$ [M+H]$^+$, 573.1687, found 573.1760.

L28(#67):
$^1$H NMR (300 MHz, DMSO-d6)δ: 9.60 (s, 1H), 8.81 (s, 1H), 8.70 (s, 1H), 8.50 (s, 1H) 8.33 (s, 1H) 8.20 (d, J=8.0 Hz, 2H), 8.12 (d, J=15.9 Hz, 1H), 7.67(t, J=7.0 Hz, 1H) 7.48 (d, J=8.0 Hz, 2H)7.17-7.34(m, 4H), 7.06 (d, J=15.9 Hz, 1H), 6.94 (t, J=7.0 Hz, 1H), 3.89 (m, 4H),2.39 (m, 4H), 2.23(s, 3H)ppm. $^{13}$C NMR (75 MHz, DMSO-d6)δ: 169.6, 164.2, 163.9, 152.3, 148.3, 140.2, 139.7, 138.7, 137.1, 133.6, 130.2, 130.0, 128.6, 128.5, 123.6, 122.4, 119.6, 113.7, 112.1, 109.9, 54.5, 45.8, 42.8. HRMS calcd for $C_{29}H_{29}ClN_9O_3$ [M+H]$^+$, 586.2076, found 586.2085.

L29(#70):
$^1$H NMR (300 MHz, DMSO-d6)δ: 9.60 (s, 1H), 8.86 (s, 1H), 8.64 (s, 1H), 7.94 (d, J=15.9 Hz, 1H), 7.72-7.65(m, 4H), 7.51 (d, J=8.5 Hz, 2H), 7.46-7.40(m, 5H), 7.36 (d, J=8.5 Hz, 2H), 6.89 (d, J=15.9 Hz, 1H),3.83 (m, 4H),3.69 (m, 4H), 2.97(s, 6H) ppm. $^{13}$C NMR (75 MHz, DMSO-d6)δ: 170.0, 164.4, 163.8, 152.4, 141.0, 138.7, 135.2, 134.1, 129.5, 129.2, 128.9, 128.2, 127.8, 120.6, 118.7, 117.2, 66.0, 43.4. HRMS calcd for $C_{31}H_{33}N_8O_3$ [M+H]$^+$, 565.1670, found 565.2676.

L30(#76):
$^1$H NMR (300 MHz, DMSO-d6)δ: 9.56 (s, 1H), 8.83 (s, 1H), 8.62(s, 1H), 7.94 (d, J=15.9 Hz, 1H), 7.71-7.64(m, 4H), 7.50 (d, J=8.5 Hz, 2H), 7.44-7.39(m, 5H), 7.30 (d, J=8.5 Hz, 2H), 6.88 (d, J=15.9 Hz, 1H), 3.82 (m, 4H),3.69 (m, 4H), 3.33(m, 2H), 2.89(m, 1H), 2.73(m, 1H), 1.63-1.61(m, 3H), 1.12-1.01(m, 2H), 0.92(d, J=6.1 Hz, 3H)ppm. $^{13}$C NMR (75

MHz, DMSO-d6)δ: 168.85, 164.44, 163.81, 152.42, 140.92, 135.22, 134.18, 134.11, 129.25, 128.91, 128.08, 127.87, 127.76, 120.59, 118.72, 117.34, 65.96, 43.37, 30.47, 21.57. HRMS calcd for $C_{35}H_{39}N_8O_3$ [M+H]$^+$,619.3140,found 619.3151.

L32(#73):
$^1$H NMR (300 MHz, DMSO-d6)δ: 9.64 (s, 1H), 9.11 (s, 1H), 8.84 (s, 1H), 8.37(t, J=5.4 Hz, 1H), 7.99 (d, J=15.9 Hz, 1H), 7.85 (d, J=8.5 Hz, 2H), 7.77-7.70(m, 4H), 7.58 (d, J=8.5 Hz, 2H), 7.52-7.45(m, 5H), 6.93 (d, J=15.9 Hz, 1H), 3.88 (m, 4H),3.74 (m, 4H), 3.49-3.45(m, 2H), 2.67(t, J=6.1 Hz, 2H), 2.41(s, 6H)ppm. $^{13}$C NMR (75 MHz, DMSO-d6)δ: 165.83, 164.45, 163.81, 152.38, 142.63, 138.65, 134.21, 134.08, 129.44, 128.91, 128.13, 127.75, 127.19, 120.59, 118.70, 116.90, 65.96, 57.73, 44.50, 43.37, 36.55. HRMS calcd for $C_{33}H_{38}N_9O_3$ [M+H]$^+$, 608.3092, found 608.3104.

L33(#74):
$^1$H NMR (300 MHz, DMSO-d6)δ: 9.61 (s, 1H), 9.54 (s, 1H), 9.25 (s, 1H), 8.50 (s, 1H), 7.95 (d, J=15.9 Hz, 1H), 7.82 (d, J=8.5 Hz, 2H), 7.72 (d, J=6.7 Hz, 2H), 7.66 (d, J=8.3 Hz, 2H), 7.55 (d, J=8.5 Hz, 2H), 7.43 (d, J=5.8 Hz, 5H), 6.89 (d, J=15.8 Hz, 1H), 3.82 (s, 4H), 3.70 (s, 4H), 3.00 (dd, J=14.2, 7.0 Hz, 4H), 2.85 (s, 4H), 1.17 (t, J=7.2 Hz, 6H). HRMS calcd for $C_{35}H_{42}N_9O_3$ [M+H]$^+$, 636.3405, found 636.3417.

L34(#77):
$^1$H NMR (300 MHz, DMSO-d6)δ: 9.61 (s, 1H), 9.02 (s, 1H), 8.77 (s, 1H), 8.37(t, J=5.4 Hz, 1H), 7.94 (d, J=15.9 Hz, 1H), 7.77 (d, J=8.5 Hz, 2H), 7.72-7.64(m, 4H), 7.52 (d, J=8.5 Hz, 2H), 7.43-7.41(m, 5H), 6.88 (d, J=15.9 Hz, 1H), 3.82 (m, 4H),3.69 (m, 4H), 3.29-3.24(m, 2H), 2.27(t, J=6.9 Hz, 2H), 2.15(s, 6H), 1.69-1.62(m, 2H)ppm. $^{13}$C NMR (75 MHz, DMSO-d6)δ: 165.6, 164.4, 152.4, 142.5, 135.2, 134.2, 134.1, 129.5, 128.9, 128.0, 127.8, 127.5, 120.6, 118.7, 116.9, 65.9, 56.9, 45.1, 43.3, 37.6, 27.1. HRMS calcd for $C_{34}H_{40}N_9O_8$ [M+H]$^+$, 662.3249,found 662.3255.

L35(#75):
$^1$H NMR (300 MHz, DMSO-d6)δ: 9.61 (s, 1H), 9.51 (s, 1H), 9.23 (s, 1H), 8.43 (s, 1H), 7.95 (d, J=15.9 Hz, 1H), 7.82 (d, J=8.5 Hz, 2H), 7.69 (dd, J=17.5, 7.5 Hz, 4H), 7.54 (d, J=8.5 Hz, 2H), 7.43 (d, J=4.6 Hz, 5H), 6.89 (d, J=15.7 Hz, 1H), 3.83 (s, 4H), 3.70 (s, 4H), 3.44 (d, J=5.4 Hz, 2H), 2.83 (d, J=45.5 Hz, 6H), 1.76 (s, 4H). $^{13}$C NMR (75 MHz, DMSO-d6)δ: 169.95, 165.83, 164.41, 163.77, 152.51, 142.80, 138.66, 135.21, 134.26, 134.05, 129.44, 128.91, 128.19, 127.76, 127.15, 126.95, 124.86, 120.59, 118.41, 116.69, 65.96, 54.46, 53.48, 45.44, 43.35, 37.46, 29.27, 29.00, 22.89. HRMS calcd for $C_{35}H_{40}N_9O_3$ [M+H]$^+$, 634.3249,found 634.3264.

L36(#72):
$^1$H NMR (300 MHz, DMSO-d6)δ: 9.66 (s, 1H), 9.50 (s, 1H), 9.22 (s, 1H), 8.52(s, 1H), 7.99 (d, J=15.9 Hz, 1H), 7.87 (d, J=8.5 Hz, 2H), 7.77-7.70(m, 4H), 7.60 (d, J=8.5 Hz, 2H), 7.49-7.43(m, 5H), 6.94 (d, J=15.9 Hz, 1H), 3.87 (m, 4H), 3.74 (m, 4H), 3.54-3.52 (m, 2H), 2.80(m, 6H), 1.66(m, 4H), 1.49(m,2H) ppm. $^{13}$C NMR (75 MHz, DMSO-d6)δ: 169.98, 165.91, 164.40, 163.76, 152.47, 142.80, 138.62, 135.19, 134.19, 134.10, 129.43, 128.91, 128.20, 127.75, 127.12, 126.92, 120.58, 118.49, 116.76, 65.96, 56.77, 53.26, 43.35, 35.56, 24.15, 22.77. HRMS calcd for $C_{36}H_{42}N_9O_3$ [M+H]$^+$, 648.3405,found 648.3423.

L37(#71):
$^1$H NMR (300 MHz, DMSO-d6)δ: 9.60 (s, 1H), 8.93 (s, 1H), 8.68 (s, 1H), 8.27(t, J=5.2 Hz, 1H),7.94 (d, J=15.9 Hz, 1H), 7.78 (d, J=8.5 Hz, 2H), 7.65-7.72(m, 4H), 7.52 (d, J=8.5 Hz, 2H), 7.40-7.46(m, 5H), 7.34 (d, J=8.5 Hz, 2H), 6.89 (d, J=15.9 Hz, 1H),3.83 (m, 4H),3.69 (m, 4H), 3.56-3.59 (m, 4H),3.35(m, 2H), 2.43-2.50(m, 6H) ppm. $^{13}$C-

NMR (75 MHz, DMSO-d6)δ: 169.99, 165.67, 164.41, 163.78, 152.34, 142.49, 138.67, 135.19, 134.23, 134.01, 129.45, 128.91, 128.08, 127.76, 127.40, 127.12, 120.56, 118.77, 116.98, 66.15, 65.96, 57.44, 53.27, 43.35, 36.41. HRMS calcd for $C_{35}H_{40}N_9O_4$ $[M+H]^+$,650.3198,found 650.3212.

L38(#84):

$^1$H NMR (300 MHz, DMSO-d6): δ 8.67 (s, 1H), 8.50 (s, 1H), 7.96(d, J=15.9 Hz, 1H), 7.74-7.72 (m, 2H), 7.49 (d, J=8.9 Hz, 2H), 7.42-7.40(m, 2H), 7.36(d, J=8.9 Hz, 2H), 7.14 (d, J=8.9 Hz, 2H), 6.94 (d, J=15.9 Hz, 1H), 6.88 (d, J=8.9 Hz, 2H), 3.72(s,3H), 3.67 (s, 2H), 3.60 (s, 4H) ppm.

L39(#85):

$^1$H NMR (300 MHz, DMSO-d6): δ 8.86 (s, 1H), 8.80 (s, 1H), 7.96(d, J=15.9 Hz, 1H), 7.73-7.11 (m, 2H), 7.52-7.45 (m, 4H), 7.42-7.40(m, 3H), 7.34 (d, J=8.7 Hz, 2H), 7.17 (d, J=8.7 Hz, 2H), 6.93 (d, J=15.9 Hz, 1H), 3.89 (s, 2H), 3.67 (s, 2H), 3.60 (s, 4H) ppm; L40(#86):

$^1$H NMR (300 MHz, DMSO-d6): δ 8.76 (s, 1H), 8.74 (s, 1H), 8.70 (s, 1H),7.96(d, J=15.9 Hz, 1H), 7.72-7.70 (m, 2H), 7.50-7.45 (m, 5H), 7.42-7.40(m, 2H), 7.15-7.10(m, 4H), 6.94 (d, J=15.9 Hz, 1H), 3.89 (s, 2H), 3.67 (s, 2H), 3.60 (s, 4H) ppm.

EXAMPLE 5

In Vitro Testing of Compounds for Antineoplastic Activity (MTT Experiments)

1) Experimental Materials

MTT, RPM1640 culture medium, fetal bovine serum, 96-well plate, $CO_2$ thermostatic incubator, American BIO-RAD680 microplate reader, cell lines of human non-small cell lung cancer (H522), and cell lines of human brain glioma (U87) were all obtained commercially.

2) Experimental Steps (1) Cell inoculation: A single cell suspension was prepared with culture media supplemented with 10% fetal bovine serum, plated into a 96-well plate with 5000 cells per well, each well having a volume of 100 μL, and cultured overnight.

(2) Preparation of compound solutions: a DMSO stock solution of a compound was diluted on a sterile bench with a culture medium into 5 concentrations to be tested, wherein a double dilution was employed between two adjacent concentrations.

(3) The compound solutions of various concentrations were added into the 96-well plate cultured overnight, with 100 μL added per well, triplicated wells for each concentration. Since the peripheral wells can have edge effect and are susceptible to contamination, no cells or compounds were added thereto; instead, 100 μL culture solution was added as a blank. Additionally, 100% wells were set to contain the cells and 100 μL culture media without any compound. The plates were incubated in a thermostatic incubator at 37° C. for 48 hours.

(4) Staining: 10 μL MTT solution (5 mg/mL, prepared with PBS) was added into the 96-well plate for staining. After incubation for 4 hours, centrifugation was performed at 2500 rpm for 10 minutes. Then, a multiple pipette was used to suck the culture solution out of the wells carefully without sucking out the cells while the pipette tip faced downward. 150 μL DMSO was added and shaken on a shaker for 5-10 minutes. Crystals were allowed to dissolve fully, and an OD value for each well was measured using the microplate reader at 570 nm. The inhibition rate was calculated as follows:

Inhibition rate(%)=(average OD value of 100% wells−average OD value of compound wells)/ (average OD value of 100% wells−average OD value of blank wells)×100%

The experimental results of the compounds are listed in the following table:

| Number (bioassay number) | $IC_{50}$(μM) H522 | $IC_{50}$(μM) U87 |
|---|---|---|
| L1(#50) | 3.26 ± 0.34 | 4.79 ± 0.55 |
| L2(#52) | 2.80 ± 0.21 | 4.75 ± 0.87 |
| L3(#51) | >30 | 10.55 ± 1.20 |
| L4(#53) | 1.92 ± 0.19 | 1.19 ± 0.07 |
| L5(#57) | 5.03 ± 0.89 | 3.32 ± 0.45 |
| L6(#54) | 5.25 ± 0.45 | 3.63 ± 0.11 |
| L7(#60) | 1.42 ± 0.12 | 1.33 ± 0.13 |
| L8(#55) | 1.82 ± 0.09 | 1.21 ± 0.16 |
| L9(#61) | 3.88 ± 0.65 | 1.47 ± 0.12 |
| L10(#43) | 2.18 ± 0.23 | 4.92 ± 0.16 |
| L11(#45) | 0.30 ± 0.03 | 2.50 ± 0.08 |
| L12(#49) | 2.55 ± 0.12 | 4.41 ± 0.43 |
| L13(#44) | 0.87 ± 0.08 | 2.04 ± 0.09 |
| L14(#42) | 5.03 ± 0.49 | 2.48 ± 0.11 |
| L15(#48) | 4.26 ± 0.10 | 2.92 ± 0.21 |
| L16(#40) | 0.78 ± 0.04 | 1.71 ± 0.06 |
| L17(#62) | >30 | 1.11 ± 0.10 |
| L18(#41) | 2.31 ± 0.17 | 1.21 ± 0.07 |
| L19(#63) | 1.34 ± 0.22 | 1.62 ± 0.09 |
| L20(#38) | 5.55 ± 0.40 | 5.12 ± 0.28 |
| L21(#39) | 7.30 ± 0.75 | 4.47 ± 0.39 |
| L22(#58) | 1.27 ± 0.08 | 1.32 ± 0.22 |
| L23(#64) | 1.44 ± 0.10 | 1.00 ± 0.06 |
| L24(#65) | 4.03 ± 0.65 | 4.40 ± 0.88 |
| L25(#59) | 2.53 ± 0.28 | 2.20 ± 0.21 |
| L26(#56) | 5.48 ± 0.76 | 3.95 ± 0.67 |
| L27(#66) | 2.21 ± 0.33 | 3.66 ± 0.55 |
| L28(#67) | 1.53 ± 0.22 | 1.49 ± 0.22 |
| L29(#70) | 6.51 ± 0.94 | 0.53 ± 0.02 |
| L30(#76) | 5.24 ± 1.33 | 0.87 ± 0.08 |
| L31(#69) | 1.05 ± 0.04 | 0.23 ± 0.01 |
| L32(#73) | 5.03 ± 0.40 | 2.48 ± 0.44 |
| L33(#74) | 4.31 ± 0.09 | 1.30 ± 0.05 |
| L34(#77) | 4.91 ± 0.10 | 2.31 ± 0.29 |
| L35(#75) | 4.14 ± 0.13 | 1.43 ± 0.10 |
| L36(#72) | 3.69 ± 0.44 | 1.11 ± 0.06 |
| L37(#71) | 5.19 ± 1.48 | 0.55 ± 0.05 |

"NA" means that the compound has no inhibiting effect on tumor cell proliferation when the highest concentration (31.6 μM) was tested.

">30" means that the compound has some inhibiting effect on tumor cells, but the inhibition rate is <50%, when the highest concentration (31.6 μM) was tested.

EXAMPLE 6

Broad-spectrum and Selectivity of the Compounds in Inhibiting Tumor Cells 8 compounds (#38-#45, L20, L21, L16, L18, L14, L10, L13 and L11 in sequence) were chosen to test their ability to inhibit growth of 11 types of human tumor cells. The method was the same as in Example 5. The cell lines tested were: cell line of human non-small cell lung cancer (H522), cell line of human colon adenocarcinoma (HCT15), cell line of human cervical cancer (Hela), cell line of human liver cancer (HepG2), cell line of human fibrosarcoma (HT1080), cell line of human erythroleukemia (KG1), cell line of human prostatic cancer (LNCaP), cell line of human breast cancer (MCF7), cell line of human ovarian cancer (OVAR3), cell line of human melanoma (SK-me128), and cell line of human brain glioma (U87). The experimental results are shown in FIG. 1.

EXAMPLE 7

Tumor Cell Vacuolization and Death by Methuosis

Figure 2:
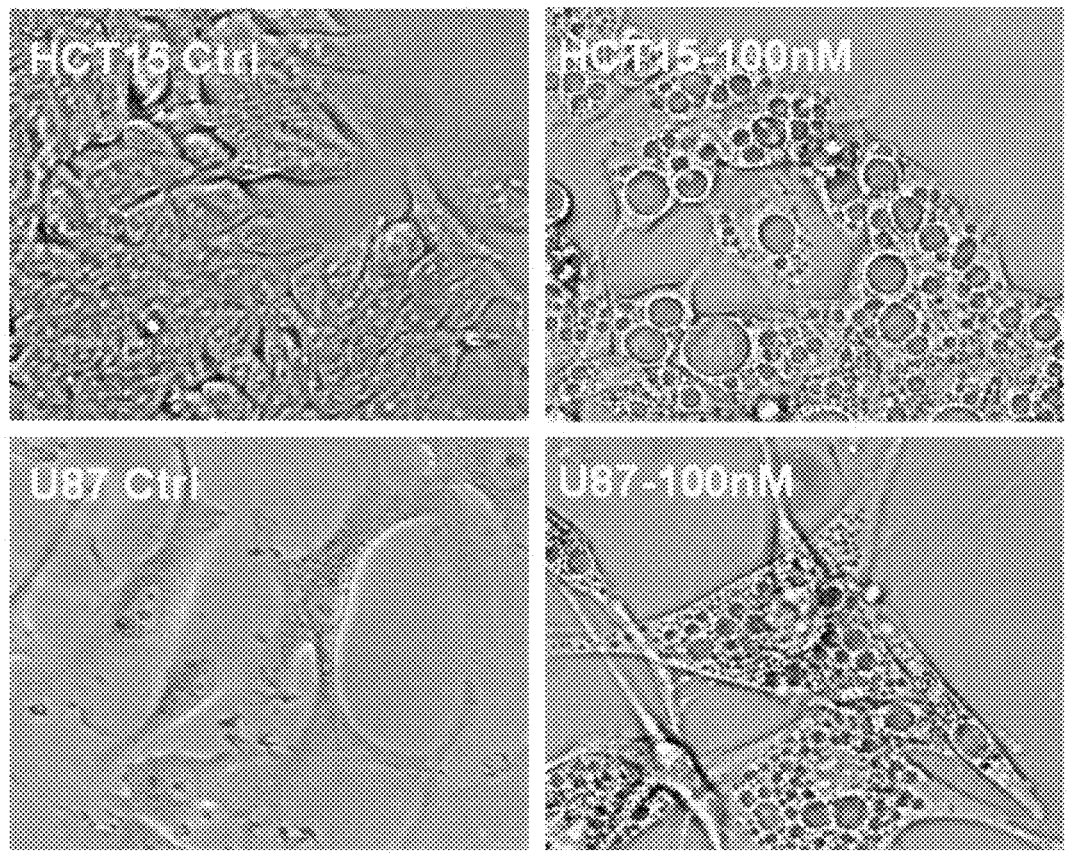
FIG. 2. Vacuolization of tumor cells. 100 microliter culture medium (RPMI1640, 2 mmol glutamine, 10% fetal bovine serum) containing $10^3$ human colon adenocarcinoma cells (HCT15) or human brain glioma cells (U87) and a solvent DMSO control or 100 nM #40 compound (L16) was plated into a 96-well cell culture plate, and cell morphological image was taken under a phase contrast microscope after cultured at 5% $CO_2$ and 37° C. for 96 hours. Both HCT5 cells (upper right) and U87 cells (lower right) treated with 100 nM #40 compound showed significant vacuolization.

After treated with certain compounds of particular structures, various types of tumor cells were observed to show a great degree of vesicle accumulation in the cytoplasm, a pheonotype of cellular vacuolization. Some cells gradually became round and eventually bursted. These changes are consistent with the features of cell death by methuosis (FIG. 2).

In order to compare the ability of different compounds to cause cell vacuolization, 100 µL culture media (RPMI1640, 2 mmol glutamine, 10% fetal bovine serum) comprising $10^3$ human glioma U87 cells and final concentrations of 0.01, 0.0316, 0.1, 0.316, 1.0, 3.160 µM respectively of the compounds to be tested were inoculated into a 96-well culture plate. After cultured at 5% $CO_2$ and 37° C. for 96 hours, cell morphology was observed under a high-magnification microscope, and the ability of the compounds to cause cell vacuolization was scored. 5 scores were given when obvious vacuolization occurred at 10 nM, 4 scores at 31.6 nM, 3 scores at 100 nM, 2 scores at 316 nM, 1 score at 1000 nM, and O score was given if no vacuation occurred at any concentration.

Figure 3:
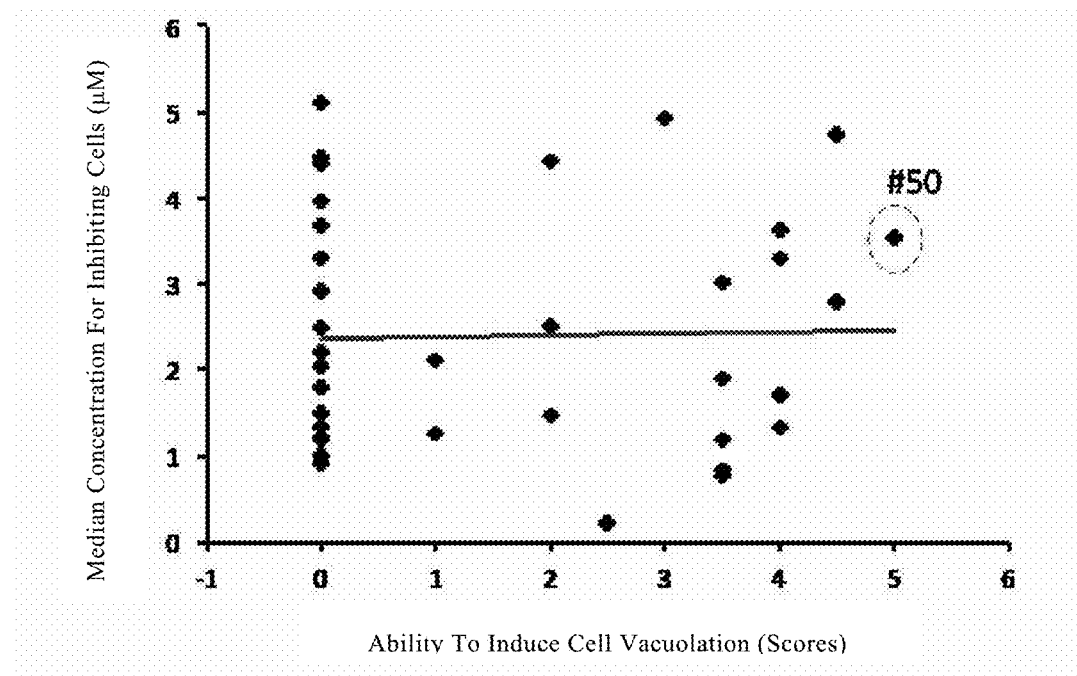
FIG. 3. The ability of the tested compounds to inhibit cell growth is not correlated with their ability to cause cell vacuolization. 37 compounds (L1-L37) were tested for their ability to inhibit growth and induce vacuolization of human glioma cells (U87). #50 compound (L1) exhibits the strongest ability to cause cell vacuolization.

FIG. 3 shows the ability of the compounds of different structures to cause cell vacuolization and their ability to inhibit cell proliferation. The specific results are shown below:

| Compound # | Vacuolation Score | $IC_{50}$ | Compound # | Vacuolation Score | $IC_{50}$ |
|---|---|---|---|---|---|
| 38 | 0 | 5.12 | 59 | 0 | 2.2 |
| 39 | 0 | 4.47 | 60 | 4 | 1.32 |
| 40 | 4 | 1.71 | 61 | 2 | 1.47 |
| 41 | 0 | 1.21 | 62 | 3.5 | 1.19 |
| 42 | 0 | 2.48 | 63 | 0 | 1.8 |
| 43 | 3 | 4.92 | 64 | 0 | 1 |
| 44 | 0 | 2.04 | 65 | 0 | 4.4 |
| 45 | 2 | 2.5 | 66 | 0 | 3.66 |
| 48 | 0 | 2.91 | 67 | 0 | 1.5 |
| 49 | 2 | 4.43 | 68 | 4 | 3.28 |
| 50 | 5 | 3.53 | 69 | 2.5 | 0.22 |
| 51 | 0 | >10 | 70 | 3.5 | 0.75 |
| 52 | 4.5 | 4.74 | 71 | 3.5 | 0.82 |
| 53 | 0 | 1.19 | 72 | 1 | 1.25 |
| 54 | 4 | 3.63 | 73 | 4.5 | 2.8 |
| 55 | 0 | 1.21 | 74 | 3.5 | 1.9 |
| 56 | 0 | 3.94 | 75 | 1 | 2.1 |
| 57 | 0 | 3.28 | 76 | 0 | 0.9 |
| 58 | 0 | 1.33 | 77 | 3.5 | 3 |

Note:
Compound #51 is not shown in FIG. 3; compound #68 is a chloride salt of compound L16 (#40).

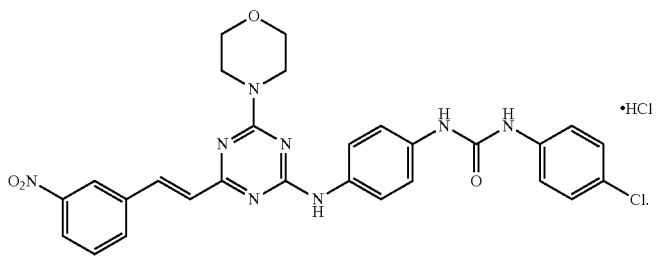 [SMILES: O=C(Nc1ccc(Cl)cc1)Nc1ccc(Nc2nc(/C=C/c3cccc([N+](=O)[O-])c3)nc(N3CCOCC3)n2)cc1 ; Cl]

In addition, compounds 79 and 14 described in Example 8 were tested according to the method described in this Example, and they were given 4.5 and 1.5 scores respectively for vacuolization.

EXAMPLE 8

Fishing of a Target Protein with a Probe

Figure 4:
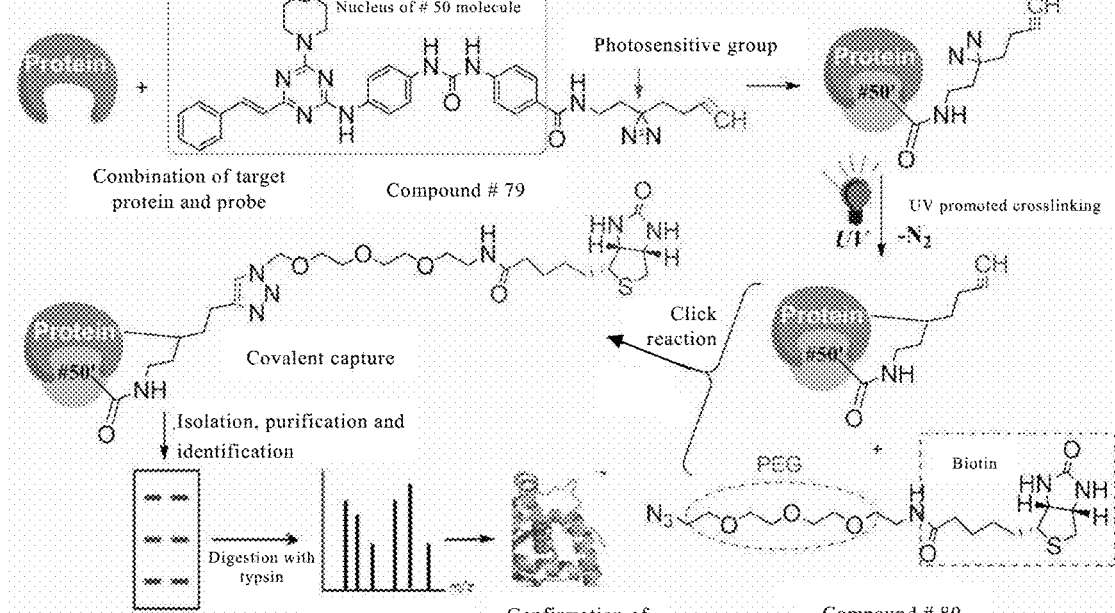
FIG. 4. A schematic view showing a flow chart for fishing a target protein with a probe. The process of fishing with the probe comprises in situ specific bonding of the probe compound to a protein of a living cell; in situ covalent crosslinking between the photosensitive group of the probe compound and its target protein under UV irradiation; specific linking of the alkynyl group of the probe compound to the azido group of the isolation compound via a click reaction; and isolating the target protein specifically bonded to the probe compound with the aid of the binding of the biotin group of the isolation compound with streptavidin-agarose bead.

FIG. 4 summarizes isolation and identification of a target protein corresponding to a compound causing cell vacuolization. The related steps are described briefly as follows.

Figure 5:
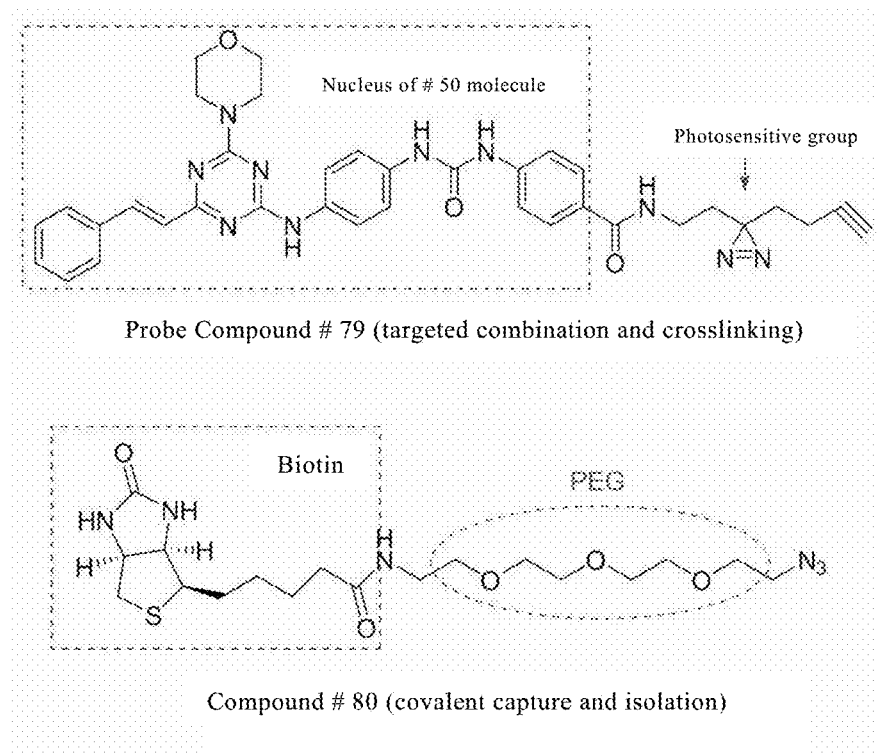
FIG. 5. A tool compound for fishing of a target protein with a probe. Among the compounds tested, #50 compound exhibits the strongest ability to cause cell vacuolization. Based on an analysis of a structure-activity relationship, linking of a photosensitive group to #50 compound on a position shown in the figure to obtain a probe #79 compound may not affect the bioactivity of #50 compound. It's also verified by experimentation that #79 compound and #50 compound can result in the same cell phenotype. To facilitate solid phase separation and reduce non-specificity, a designed #80 compound has a long chain linking a biotin to an azido group for a click reaction.

Synthesis of the Probe (FIG. 5):

Synthetic Route and Synthesis of Compound #79:

(E)-N-(2-(3-(1-butyn-4-yl)-3H-diaziridin-3-yl)ethyl)-4-(3-(4-((4-(morpholin-1-yl)-6-styrenyl-1,3,5-triazin-2-yl)amino)phenyl)urea)benzamide (79)

At room temperature, intermediate 14 (100 mg, 0.186 mmol), HOBt (32.7 mg, 0.242 mmol), DMF (2 mL), EDCI (53.5 mg, 0.279 mmol), C1 (33.0 mg, 0.242 mmol) and triethylamine (37.6 mg, 0.372 mmol) were added in sequence to a 25 mL reaction flask, and stirred for reaction for 8 hours. After completion of the reaction, the reaction liquid was poured into 10 mL iced water, extracted with methylene dichloride (20 mL), and washed in sequence with water and saturated brine. The organic layer was dried with anhydrous sodium sulfate, and the solvent was evaporated

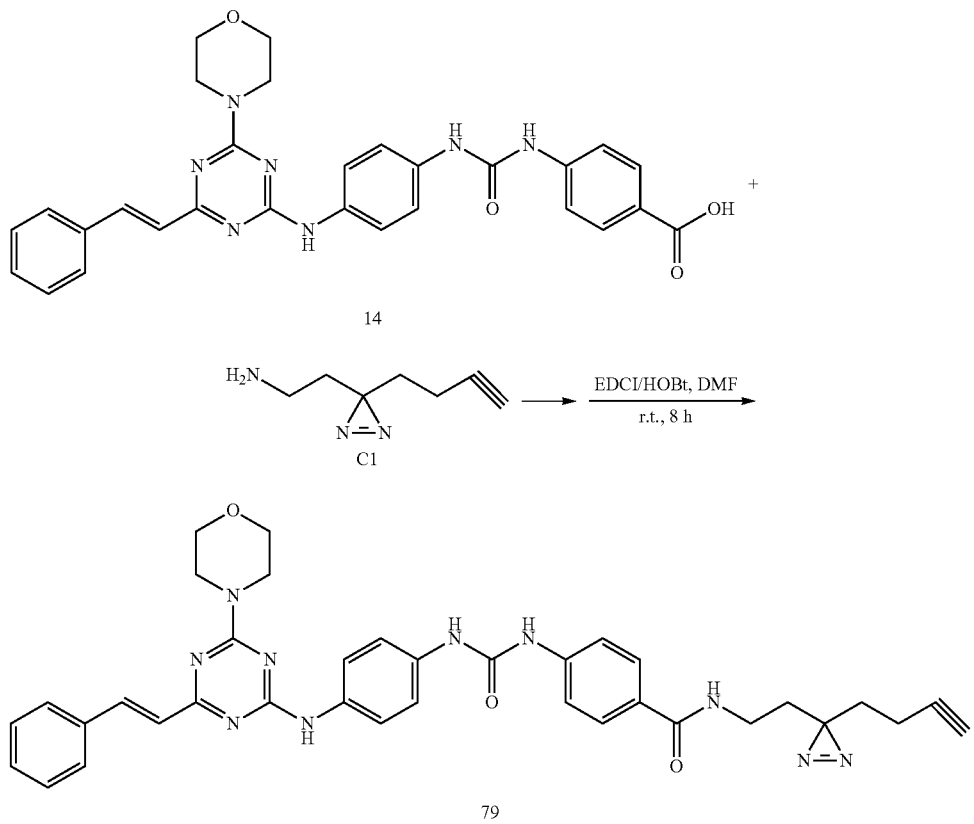

wherein side chain C1 was prepared with reference to the method described in the article (Li, Z., Hao P., Li L. et al. Design and synthesis of minimalist terminal alkyne-containing diazirine photo-crosslinkers and their incorporation into kinase inhibitors for cell- and tissue-based proteome profiling. *Angew. Chem. Int. Ed.,* 2013, 52, 8551-8556).

Compound 14 ((E)-1-(4-carboxyphenyl)-3-(4-(4-(morpholin-1-yl)-6-styrenyl-1,3,5-triazinyl-2-amino)phenyl)urea) was prepared using the method of Example 2 and corresponding materials, and the mass spectrum data thereof are as follows:

$^1$H NMR (300 MHz, DMSO-d6)δ: 12.33 (s, 1H), 9.59 (s, 1H), 9.41 (s, 1H), 9.09 (s, 1H), 7.94 (d, J=15.9 Hz, 1H), 7.88 (d, J=8.3 Hz, 2H), 7.77-7.63 (m, 4H), 7.59 (d, J=8.3 Hz, 2H), 7.51-7.36 (m, 5H), 6.89 (d, J=15.9 Hz, 1H), 3.83 (s, 4H), 3.69 (s, 4H) ppm.

completely. After silica gel column chromatography, 92.8 mg pale yellow solid was obtained at a yield of 76%. $^1$H NMR(300 MHz, DMSO-d6): δ 9.62(s, 1H), 8.94(s, 1H), 8.68(s, 1H), 8.34(t, J=5.2 Hz, 1H), 7.96(d, J=15.9 Hz, 1H), 7.80(d, J=8.6 Hz, 2H), 7.67-7.74(m, 4H), 7.55 (d, J=8.6 Hz, 2H), 7.42-7.48(m, 5H), 6.90(d, J=15.9 Hz, 1H), 3.84(m, 4H), 3.71(m, 4H), 3.13-3.20(m, 2H), 2.87(d, J=2.5 Hz, 1H), 2.04(td, J=7.4 Hz, J=2.5 Hz, 2H), 1.62-1.69(m, 4H)ppm. $^{13}$C NMR (75 MHz, DMSO-d6)δ: 170.05, 165.66, 164.41, 163.87, 152.16, 142.45, 140.30, 139.59, 138.91, 135.22, 129.44, 128.87, 128.63, 128.07, 127.77, 127.40, 127.01, 117.02, 113.69, 112.13, 109.78, 83.13, 71.72, 66.05, 43.41, 34.27, 31.99, 31.30, 27.28, 12.67. ES-MSm/Z: 655.5[M−H]$^−$, $C_{36}H_{36}N_{10}O_3$(MW=656.7).

Synthetic Route and Synthesis of #80 Compound:

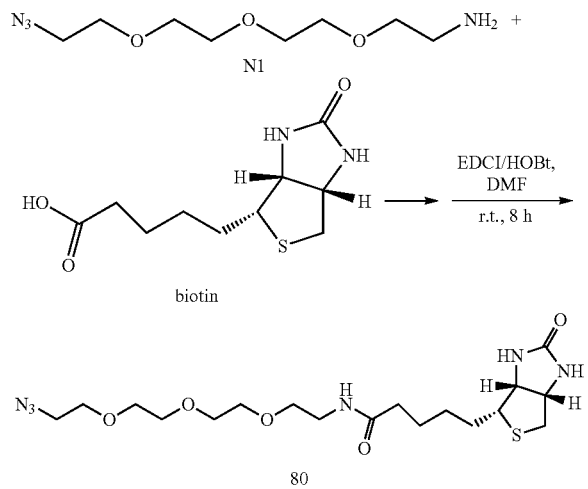

wherein reagent N1 and biotin were commercially available products.

N-(2-(2-(2-(2-azidoethoxy)ethoxy)ethoxy)ethan-1-yl)biotin amide (80)

At room temperature, biotin (94 mg, 0.385 mmol, biotin), HOBt (74.5 mg, 0.551 mmol), DMF (2 mL), EDCI (106 mg, 0.551 mmol), N1 [80 mg, 0.367 mmol, named 2-(2-(2-(2-azidoethoxy)ethoxy)ethoxy)ethan-1-amine] and triethylamine (55.7 mg, 0.551 mmol) were added in sequence to a 25 mL reaction flask, and stirred for reaction for 8 hours. After completion of the reaction, the reaction liquid was poured into 10 mL iced water, extracted with methylene dichloride (20 mL), and washed in sequence with water and saturated brine. The organic layer was dried with anhydrous sodium sulfate, and the solvent was evaporated completely. After silica gel column chromatography, 123 mg pale yellow solid was obtained at a yield of 72%. $^1$H NMR (300 MHz, DMSO-d6) δ: 4.31(m, 1 H, CH-1-biotin), 4.14(m, 1 H, CH-4-biotin), 3.55-3.52(m, 8H, O(CH$_2$CH$_2$O)-PEG), 3.40-3.38(m 4H, CH$_2$NH and CH$_2$N$_3$-PEG), 3.10(m, 1 H, CH-3-biotin), 2.83(dd, 1 H, J=4.8, 12.3 Hz, CH-2a-biotin), 2.60-2.56(m, 1 H, CH-2b-biotin), 2.07(t, 2 H, J=7.2 Hz, CH$_2$CO-biotin), 1.50-1.30(m, 6 H, (CH$_2$)$_3$-biotin).

Cell culture: An amount of human glioma cells U87 were plated in an 150 cm$^2$ Petri dish and cultured for 48 hours to reach 75-90% confluence. The culture medium was replaced with a prewarmed medium containing either 0.5 μM probe (#79 compound) or an equivalent volume of DMSO control. The cells continued in culture for 3 hours.

UV promoted crosslinking: The cells were washed twice with a prechilled phosphate buffer saline (PBS). The cell-culture dish was placed on ice, and the cells were irradiated with ultraviolet light (an ultraviolet lamp having a power of 100 W, wavelength 350 nm, or 315-385 nm) through the top of the dish for 1 hour. Alternatively, a minimal amount of prechilled PBS (10 ml/150 cm$^2$) was added to the cell-culture dish which was then placed on an ultraviolet irradiator. The bottom of the cell-culture dish received irradiation for 30 minutes (wavelength 315-385 nm, time being adjusted in light of the ultraviolet power).

Preparation of cell lysis solution: The cells were dissociated with trypsin, precipitated by centrifugation, and washed twice with PBS. The cells was resuspended in HEPES lysis buffer (25 mM Hepes, 150 mM sodium chloride, 2 mM magnesium chloride, 0.1% NP-40, protease inhibitor, pH7.5), homogenized by a short ultra-sonication (dispensable), mixed by rotation at 4° C. for 30 minutes, and then centrifuged at 4° C. for 10 minutes at a high speed. The protein concentration of the cell lysate was measured using the Bradford method.

Pre-clearance: 1 mL cell lysate (1-2 mg/mL) was added with streptavidin-agarose beads pre-equilibrated with HEPES buffer (25 mM Hepes, 150 mM sodium chloride, 2 mM magnesium chloride, pH7.5) and mixed by rotation at 4° C. for 2 hours or overnight. The supernatant was kept after centrifugation.

Click reaction: 940 μL of the supernatant as described above was added with a freshly prepared reaction mixture (20 μL 50 mM CuSO$_4$, 10 L freshly prepared 10 mM TBTA, namely tris[(1-benzyl-1H-1,2,3-triazol-4-yl)methyl]amine, 20 μL 50 mM TCEP, namely tris(2-carboxyethyl)phosphine, and 10 L 1 mM #80 compound), and gently mixed at room temperature for 2 hours. A double-volume acetone pre-chillled at −20° C. was added to stop the reaction. The resultant was centrifuged at 4° C. for 10 minutes at a high speed (13000 rpm) to precipitate protein. The protein pellet was washed twice with 500 μL precooled methanol, and dissolved in 1 mL 0.1% SDS PBS with ultasonication.

Figure 6:
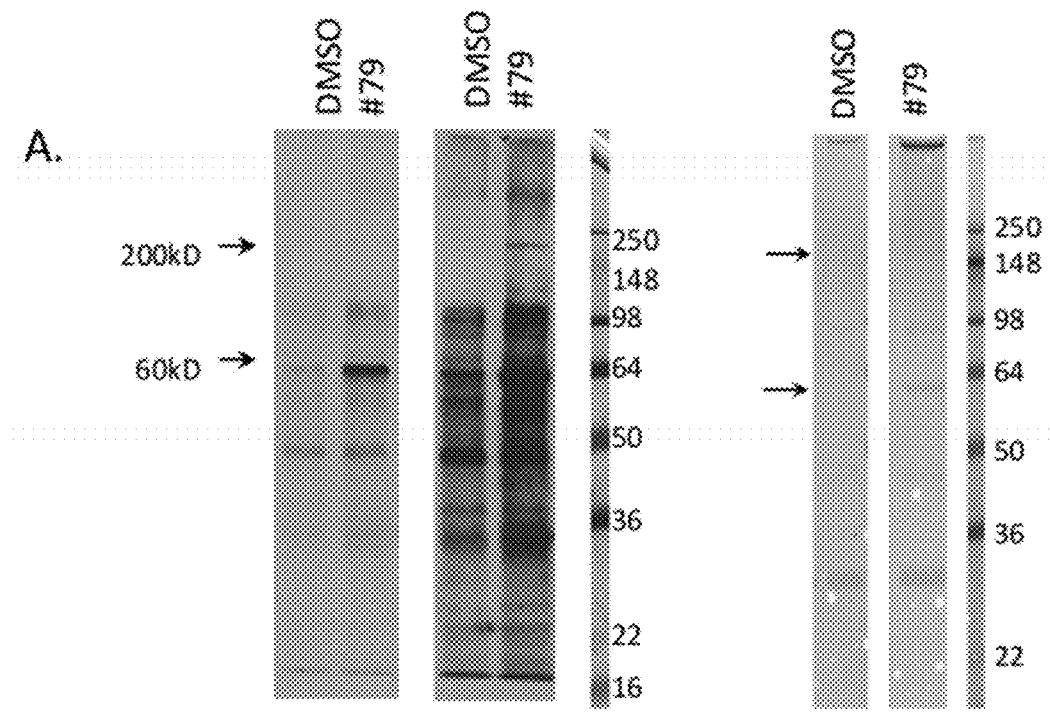
FIG. 6. Separation and identification of a target protein. #79 compound used as a probe is bonded in situ to a target protein within a cell wherein a photo-promoted covalent linking is formed, and then reacts with #80 compound to achieve solid phase separation and purification of the target protein. A. Left: Proteins capable of specific bonding with #79 compound as detected by Western immunoblotting (as indicated by the arrows); right: specific target proteins separated by PAGE gel electrophoresis as indicated by coomassie blue staining. B. As shown by MALDI-mass spectrum peptide segment mapping and sequence analysis (MALDI-MS/MS), the target proteins match the known protein sequences in the data bank. The underlined bold portions are the matched sequences. The two isolated proteins of about 60 KD and about 200 KD match the same known protein sequence. C. The information of protein matching shows that the target protein of the compound is vimentin (SEQ ID NO: 1).

Purification of target protein: The solution of the redissolved protein as described above was added with streptavidin-agarose beads (200 μL pellet volume) equilibrated with PBS, mixed by rotation at 4° C. for 2 hours or overnight, centrifuged to precipitate the agarose beads. The beads were washed once with 0.1% SDS PBS and four times with PBS, added an equivalent beads volume of 2×SDS loading buffer, and boiled for 15 minutes. After centrifugation, the supernatant was loaded in 10% SDS-PAGE for protein separation. The gel was then stained with a 20 mL coomassie blue solution for 1 hour, then destained with 2×500 ml double distilled water for 2×1 hours. Specific protein bands was cut from the destained gel (FIG. 6, A).

Protein identification: MALDI-mass spectrum peptide segment mapping and sequence analysis (MALDI-MS/MS) was used to identify the purified protein. The peptide segment sequences of the purified protein matched the sequence of vimentin in the data bank (FIG. 6, B, C).

EXAMPLE 9

Results of Molecular Docking of #50 Compound with the Target Protein

Figure 7:
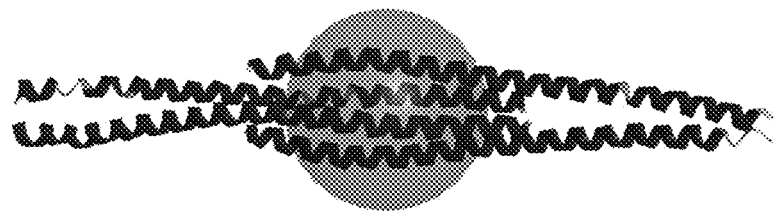
FIG. 7. Results of docking between #50 compound and the target protein. A: 3KLT (system number of the protein; the spherical portion in the center is the active region of the protein) of vimentin tetramer originated from the PDB (protein data bank); B: #50 compound for docking; C: scores of the top 10 configurations of #50 compound resulting from docking between 3KLT and #50 compound using software Discovery Studio 3.0 and the LibDock docking method therein; D: a view showing the interaction between the #50 compound configuration having the highest score (indicated by purple color) and vimentin; E: amino acids forming hydrogen bonds with #50 compound after deproteinization, wherein the two amino acids, Arg273 and Tyr276, form hydrogen bonds with the triazine ring in #50 compound.
Figure 7:
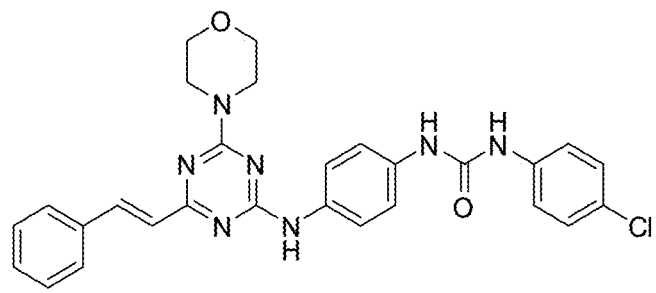
Figure 7:
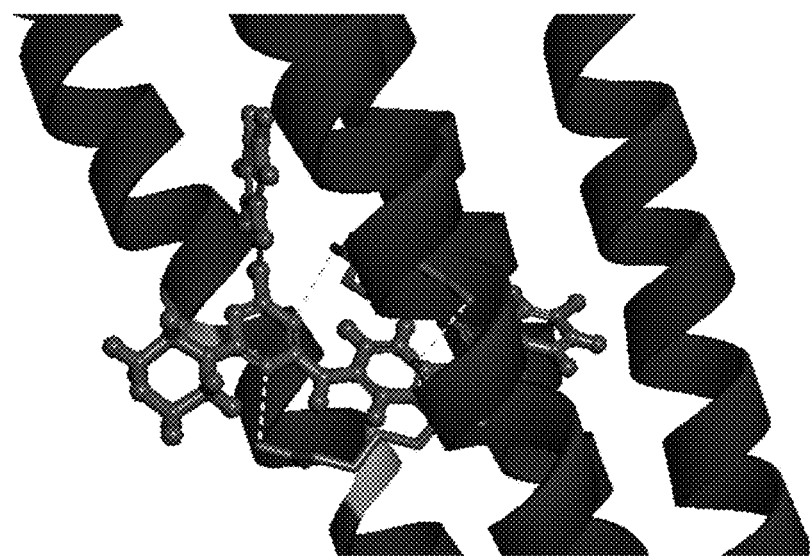
Figure 7:
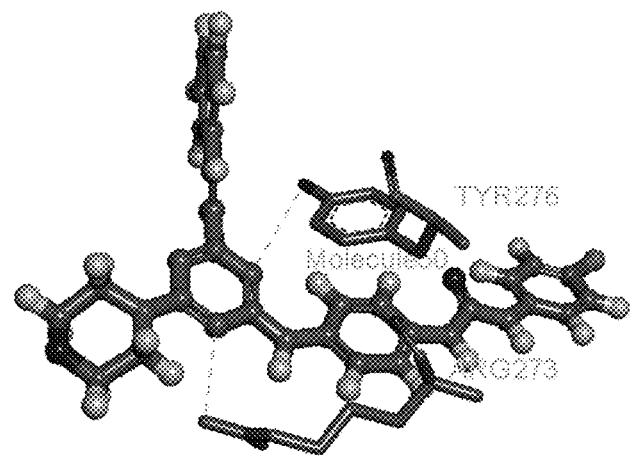

Software Discovery Studio 3.0 was chosen, and the LibDock docking method therein was used to dock 3KLT of vimentin tetramer originated from the PDB (protein data bank) (see A in FIG. 7) and #50 compound (B in FIG. 7). A pink spherical active pouch was built in view of the ligand carried by 3KLT itself, wherein the radius was set to 10 Å; the number of the lattice points was 1000; the method used to produce configurations was Best; the maximal number of the small molecule configurations generated was set to 255; and the rest parameters were defaults. Scores of the top 10 configurations for #50 compound were obtained (see C in FIG. 7). Then, a picture showing the interaction between vimentin and the configuration of #50 compound having the highest score (D in FIG. 7) was provided. Amino acids forming hydrogen bonds with the #50 compound after deproteinization were also shown (E in FIG. 7). As can be seen, only two amino acids, Arg273 and Tyr276, formed hydrogen bonds with the triazine ring in #50 compound.

What is claimed is:

1. A compound represented by general Formula I:

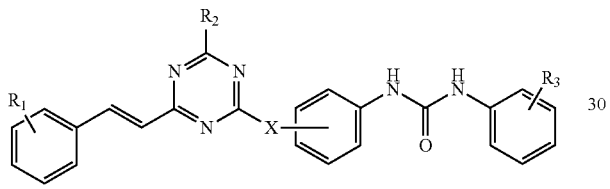

(I)

or a pharmaceutically acceptable salt, or solvate thereof, wherein:

$R_1$ is hydrogen, halogen, nitro, amino, hydroxyl, $C_1$-$C_{12}$ alkyl, $C_1$-$C_6$ alkoxyl, $C_1$-$C_6$ alkylamino, di-$C_1$-$C_6$ alkylamino, hydroxymethyl, or aminomethyl;

$R_2$ is —$NR_4R_5$, wherein $R_4$ and $R_5$ are independently selected from the group consisting of hydrogen, $C_1$-$C_6$ alkyl and $C_1$-$C_6$ haloalkyl; or $R_4$, $R_5$ and the nitrogen atom bonded to them form a saturated or unsaturated 4 to 6-member heterocyclic ring containing optionally an additional heteroatom selected from the group consisting of $NR_6$, O and S, wherein the heterocyclic ring is optionally substituted with hydroxyl, halogen, nitro, amino or $C_1$-$C_6$ alkyl, wherein $R_6$ is hydrogen, hydroxyl, $C_1$-$C_6$ alkyl, or $C_1$-$C_6$ haloalkyl;

$R_3$ is hydrogen, halogen, nitro, amino, hydroxyl, $C_1$-$C_{12}$ alkyl, $C_1$-$C_6$ alkoxyl, $C_1$-$C_6$ alkylamino, di-$C_1$-$C_6$ alkylamino, hydroxymethyl, aminomethyl or —$COR_a$;

$R_a$ is OH or $NR_7R_8$, wherein $R_7$ and $R_8$ are independently selected from the group consisting of hydrogen, $C_1$-$C_6$ alkyl optionally substituted with one or more substituents selected from halogen or $NR_9R_{10}$, and $C_1$-$C_6$ alkyl substituted with 3-($C_2$-$C_6$ alkynyl)-3H-diaziridinyl; or $R_7$, $R_8$ and the nitrogen atom bonded to them form a 4 to 6-member heterocyclic ring containing optionally an additional heteroatom selected from the group consisting of N, O and S, and optionally substituted with $C_1$-$C_6$ alkyl;

$R_9$ and $R_{10}$ are independently selected from the group consisting of hydrogen and $C_1$-$C_6$ alkyl; or $R_9$, $R_{10}$ and the nitrogen atom bonded to them form a 4 to 6-member heterocyclic ring containing optionally an additional heteroatom selected from a group consisting of N, O and S; and X is NH or O, linked to the phenyl group on a para- or meta-position.

2. The compound, pharmaceutically acceptable salt, or solvate of claim 1, wherein:

$R_1$ is hydrogen, halogen or nitro; and/or $R_2$ is —$NR_4R_5$, wherein $R_4$ and $R_5$ are independently selected from a group consisting of hydrogen, $C_1$-$C_6$ alkyl, $C_1$-$C_6$ haloalkyl; or $R_4$, $R_5$ and the nitrogen atom bonded to them form a saturated or unsaturated 4 to 6-member heterocyclic ring containing optionally an additional heteroatom selected from a group consisting of $NR_6$, O and S, wherein the heterocyclic ring is optionally substituted with hydroxyl, halogen, nitro, amino or $C_1$-$C_6$ alkyl; wherein $R_6$ is hydrogen, hydroxyl or $C_1$-$C_6$ alkyl; and/or $R_3$ is hydrogen, halogen, nitro, amino, hydroxyl, $C_1$-$C_6$ alkyl, hydroxymethyl, aminomethyl or —$COR_a$; wherein $R_a$ is OH or $NR_7R_8$, wherein $R_7$ and $R_8$ are independently selected from the group consisting of hydrogen, $C_1$-$C_6$ alkyl optionally substituted with one or more substituents selected from halogen or $NR_9R_{10}$, and $C_1$-$C_6$ alkyl substituted with 3-($C_2$-$C_6$ alkynyl)-3H-diaziridinyl; or $R_7$, $R_8$ and the nitrogen atom bonded to them form a 4 to 6-member heterocyclic ring containing optionally an additional heteroatom selected from the group consisting of N, O and S, and optionally substituted with $C_1$-$C_6$ alkyl; wherein $R_9$ and $R_{10}$ are independently selected from a group consisting of hydrogen and $C_1$-$C_6$ alkyl; or $R_9$, $R_{10}$ and the nitrogen atom bonded to them form a 4 to 6-member heterocyclic ring containing optionally an additional heteroatom selected from a group consisting of N, O and S; and/or X is NH, linked to the phenyl group at a para- or meta-position.

3. The compound, pharmaceutically acceptable salt, or solvate of claim 2, wherein:

$R_2$ is —$NR_4R_5$, wherein $R_4$ and $R_5$ are independently selected from a group consisting of hydrogen and $C_1$-$C_6$ alkyl; or $R_4$, $R_5$ and the nitrogen atom bonded to them form a saturated 4 to 6-member heterocyclic ring containing optionally an additional heteroatom selected from the group consisting of $NR_6$, O and S, wherein the heterocyclic ring is optionally substituted with hydroxyl, halogen, nitro, amino or $C_1$-$C_6$ alkyl, wherein $R_6$ is hydrogen or $C_1$-$C_6$ alkyl; and/or R₃ is halogen, C₁-C₆ alkoxyl or —COR_a; wherein R_a is OH or NR₇R₈, wherein R₇ and R₈ are independently selected from a group consisting of C₁-C₆ alkyl optionally substituted with NR₉R₁₀, and C₁-C₆ alkyl substituted with 3-(C₂-C₆ alkynyl)-3H-diaziridinyl; or R₇, R₈ and the nitrogen atom bonded to them form a saturated 4 to 6-member heterocyclic ring containing optionally an additional heteroatom selected from N or O, and optionally substituted with C₁-C₆ alkyl; wherein R₉ and R₁₀ are independently selected from a group consisting of hydrogen and C₁-C₆ alkyl; or R₉, R₁₀ and the nitrogen atom bonded to them form a saturated 4 to 6-member heterocyclic ring containing optionally an additional heteroatom selected from N or O.

4. The compound, pharmaceutically acceptable salt, or solvate of claim 1, wherein:

R₁ is hydrogen, halogen or nitro;

R₂ is —NR₄R₅, wherein R₄, R₅ and the nitrogen atom bonded to them form a saturated 4 to 6-member heterocyclic ring containing optionally an additional heteroatom selected from the group consisting of NR₆ and O, wherein the heterocyclic ring is optionally substituted with a substituent selected from hydroxyl and C₁-C₆ alkyl; wherein R₆ is hydrogen or C₁-C₆ alkyl;

R₃ is halogen or —COR_a; wherein R_a is OH or NR₇R₈, wherein R₇ and R₈ are independently selected from a group consisting of C₁-C₆ alkyl optionally substituted with NR₉R₁₀, and C₁-C₆ alkyl substituted with 3-(C₂-C₆ alkynyl)-3H-diaziridinyl; or R₇, R₈ and the nitrogen atom bonded to them form a saturated 4 to 6-member heterocyclic ring containing optionally an additional heteroatom selected from N or O, and optionally substituted with C₁-C₆ alkyl; wherein R₉ and R₁₀ are independently selected from the group consisting of hydrogen and C₁-C₆ alkyl; or R₉, R₁₀ and the nitrogen atom bonded to them form a saturated 4 to 6-member heterocyclic ring containing optionally an additional heteroatom selected from N or O; and X is NH, linked to the phenyl group at a para- or meta-position.

5. The compound, pharmaceutically acceptable salt, or solvate of claim 1, wherein the compound has a structure represented by Formula (I-1), (I-2) or (I-3):

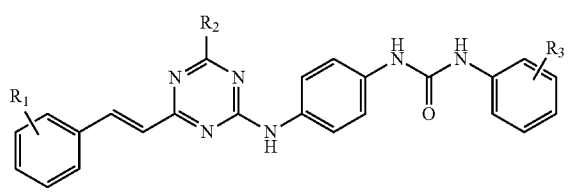

(I-1)

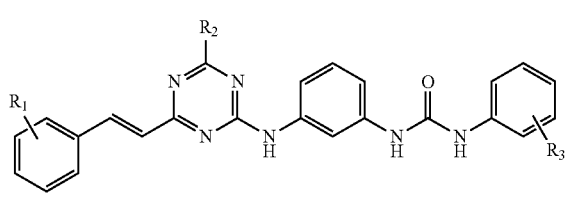

(I-2)

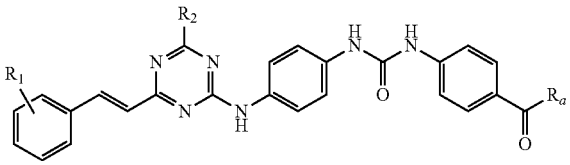

(I-3)

wherein, in Formula (I-1) or (I-2),

R₁ is hydrogen, halogen or nitro;

R₂ is selected from a group consisting of morpholinyl, pyrrolidinyl, piperazinyl, and azetidinyl, which are optionally substituted with hydroxyl or C₁-C₆ alkyl; and R₃ is halogen or COR_a; wherein R_a is OH or NR₇R₈, wherein R₇ and R₈ are independently selected from a group consisting of C₁-C₆ alkyl optionally substituted with NR₉R₁₀, and C₁-C₆ alkyl substituted with 3-(C₂-C₆ alkynyl)-3H-diaziridinyl; or R₇, R₈ and the nitrogen atom bonded to them form a saturated 4 to 6-member heterocyclic ring containing optionally an additional heteroatom selected from N or O, and optionally substituted with C₁-C₆ alkyl; wherein R₉ and R₁₀ are independently selected from a group consisting of hydrogen and C₁-C₆ alkyl; or R₉, R₁₀ and the nitrogen atom bonded to them form a saturated 4 to 6-member heterocyclic ring containing optionally an additional heteroatom selected from N or O;

in Formula (I-3),

R₁ is H;

R₂ is morpholinyl;

R_a is OH or NR₇R₈, wherein R₇ and R₈ are independently selected from a group consisting of C₁-C₆ alkyl optionally substituted with NR₉R₁₀, and C₁-C₆ alkyl substituted with 3-(C₂-C₆ alkynyl)-3H-diaziridinyl; or R₇, R₈ and the nitrogen atom bonded to them form a saturated 4 to 6-member heterocyclic ring containing optionally an additional heteroatom selected from N or O, and optionally substituted with C₁-C₆ alkyl; wherein R₉ and R₁₀ are independently selected from a group consisting of hydrogen and C₁-C₆ alkyl; or R₉, R₁₀ and the nitrogen atom bonded to them form a saturated 4 to 6-member heterocyclic ring containing optionally an additional heteroatom selected from N or O.

6. The compound, pharmaceutically acceptable salt, or solvate of claim 5, wherein, in Formula (I-1), R₁ is hydrogen, halogen or nitro;

R₂ is morpholinyl; and

R₃ is halogen or COR_a; wherein R_a is OH or NR₇R₈, wherein R₇ and R₈ are independently selected from a group consisting of C₁-C₆ alkyl optionally substituted with NR₉R₁₀, and C₁-C₆ alkyl substituted with 3-(C₂-C₆ alkynyl)-3H-diaziridinyl; or R₇, R₈ and the nitrogen atom bonded to them form a saturated 4 to 6-member heterocyclic ring containing optionally an additional heteroatom selected from N or O, and optionally substituted with C₁-C₆ alkyl; wherein R₉ and R₁₀ are independently selected from a group consisting of hydrogen and C₁-C₆ alkyl; or R₉, R₁₀ and the nitrogen atom bonded to them form a saturated 4 to 6-member heterocyclic ring containing optionally an additional heteroatom selected from N or O.

7. The compound, pharmaceutically acceptable salt, or solvate of claim 1, wherein the compound is selected from a group consisting of:

(E)-1-(4-chlorophenyl)-3-(4-(4-(morpholin-1-yl)-6-styrenyl-1,3,5-triazinyl-2-amino)phenyl)urea;
(E)-1-(4-fluorophenyl)-3-(4-(4-(morpholin-1-yl)-6-styrenyl-1,3,5-triazinyl-2-amino)phenyl)urea;
(E)-1-(4-chlorophenyl)-3-(4-(4-(4-methylpiperazin-1-yl)-6-styrenyl-1,3,5-triazinyl-2-amino)phenyl)urea;
(E)-1-(4-fluorophenyl)-3-(4-(4-(4-methylpiperazin-1-yl)-6-styrenyl-1,3,5-triazinyl-2-amino)phenyl)urea;
(E)-1-(4-chlorophenyl)-3-(4-(4-(3-hydroxyazetidin-1-yl)-6-styrenyl-1,3,5-triazinyl-2-amino)phenyl)urea;
(E)-1-(4-chlorophenyl)-3-(4-(4-(morpholin-1-yl)-6-(3-chlorostyrenyl)-1,3,5-triazinyl-2-amino)phenyl)urea;
(E)-1-(4-fluorophenyl)-3-(4-(4-(morpholin-1-yl)-6-(3-chlorostyrenyl)-1,3,5-triazinyl-2-amino)phenyl)urea;
(E)-1-(4-chlorophenyl)-3-(4-(4-(4-methylpiperazin-1-yl)-6-(3-chlorostyrenyl)-1,3,5-triazinyl-2-amino)phenyl)urea;
(E)-1-(4-fluorophenyl)-3-(4-(4-(4-methylpiperazin-1-yl)-6-(3-chlorostyrenyl)-1,3,5-triazinyl-2-amino)phenyl)urea;
(E)-1-(4-chlorophenyl)-3-(4-(4-(morpholin-1-yl)-6-(4-chlorostyrenyl)-1,3,5-triazinyl-2-amino)phenyl)urea;
(E)-1-(4-fluorophenyl)-3-(4-(4-(morpholin-1-yl)-6-(4-chlorostyrenyl)-1,3,5-triazinyl-2-amino)phenyl)urea;
(E)-1-(3-fluorophenyl)-3-(4-(4-(morpholin-1-yl)-6-(4-chlorostyrenyl)-1,3,5-triazinyl-2-amino)phenyl)urea;
(E)-1-(4-chlorophenyl)-3-(4-(4-(4-methylpiperazin-1-yl)-6-(4-chlorostyrenyl)-1,3,5-triazinyl-2-amino)phenyl)urea;
(E)-1-(4-fluorophenyl)-3-(4-(4-(4-methylpiperazin-1-yl)-6-(4-chlorostyrenyl)-1,3,5-triazinyl-2-amino)phenyl)urea;
(E)-1-(3-fluorophenyl)-3-(4-(4-(4-methylpiperazin-1-yl)-6-(4-chlorostyrenyl)-1,3,5-triazinyl-2-amino)phenyl)urea;
(E)-1-(4-chlorophenyl)-3-(4-(4-(morpholin-1-yl)-6-(3-nitrostyrenyl)-1,3,5-triazinyl-2-amino)phenyl)urea;
(E)-1-(4-fluorophenyl)-3-(4-(4-(morpholin-1-yl)-6-(3-nitrostyrenyl)-1,3,5-triazinyl-2-amino)phenyl)urea;
(E)-1-(4-chlorophenyl)-3-(4-(4-(4-methylpiperazin-1-yl)-6-(3-nitrostyrenyl)-1,3,5-triazinyl-2-amino)phenyl)urea;
(E)-1-(4-fluorophenyl)-3-(4-(4-(4-methylpiperazin-1-yl)-6-(3-nitrostyrenyl)-1,3,5-triazinyl-2-amino)phenyl)urea;
(E)-1-(4-chlorophenyl)-3-(4-(4-dimethylamino-6-(3-nitrostyrenyl)-1,3,5-triazinyl-2-amino)phenyl)urea;
(E)-1-(4-chlorophenyl)-3-(4-(4-(pyrrolidin-1-yl)-6-(3-nitrostyrenyl)-1,3,5-triazinyl-2-amino)phenyl)urea;
(E)-1-(4-chlorophenyl)-3-(4-(4-(3-hydroxyazetidin-1l-yl)-6-(3-nitrostyrenyl)-1,3,5-triazinyl-2-amino)phenyl)urea;
(E)-1-(4-chlorophenyl)-3-(3-(4-(morpholin-1-yl)-6-styrenyl-1,3,5-triazinyl-2-amino)phenyl)urea;
(E)-1-(4-chlorophenyl)-3-(3-(4-(4-methylpiperazin-1-yl)-6-styrenyl-1,3,5-triazinyl-2-amino)phenyl)urea;
(E)-1-(4-chlorophenyl)-3-(3-(4-(morpholin-1-yl)-6-(3-chlorostyrenyl)-1,3,5-triazinyl-2-amino)phenyl)urea;
(E)-1-(4-chlorophenyl)-3-(3-(4-(4-methylpiperazin-1-yl)-6-(3-chlorostyrenyl)-1,3,5-triazinyl-2-amino)phenyl)urea;
(E)-1-(4-chlorophenyl)-3-(3-(4-(morpholin-1-yl)-6-(3-nitrostyrenyl)-1,3,5-triazinyl-2-amino)phenyl)urea;
(E)-1-(4-chlorophenyl)-3-(3-(4-(4-methylpiperazin-1-yl)-6-(3-nitrostyrenyl)-1,3,5-triazinyl-2-amino)phenyl)urea;
(E)-N,N-dimethyl-4-(3-(4-(4-(morpholin-1-yl)-6-styrenyl-1,3,5-triazinyl-2-amino)phenyl)urea)benzamide;
(E)-1-(4-((4-methylpiperazin-1-yl)formyl)phenyl)-3-(4-(4-(morpholin-1-yl)-6-styrenyl-1,3,5-triazinyl-2-amino)phenyl)urea;
(E)-1-(4-((4-methylpiperazin-1-yl)formyl)phenyl)-3-(4-(4-(morpholin-1-yl)-6-styrenyl-1,3,5-triazinyl-2-amino)phenyl)urea;
(E)-N-(2-(dimethylamino)ethyl)-4-(3-(4-(4-(morpholin-1-yl)-6-styrenyl-1,3,5-triazinyl-2-amino)phenyl)urea)benzamide;
(E)-N-(2-(diethylamino)ethyl)-4-(3-(4-(4-(morpholin-1-yl)-6-styrenyl-1,3,5-triazinyl-2-amino)phenyl)urea)benzamide;
(E)-N-(3-(dimethylamino)propyl)-4-(3-(4-(4-(morpholin-1-yl)-6-styrenyl-1,3,5-triazinyl-2-amino)phenyl)urea)benzamide;
(E)-N-(2-(pyrrolidin-1-yl)ethyl)-4-(3-(4-(4-(morpholin-1-yl)-6-styrenyl-1,3,5-triazinyl-2-amino)phenyl)urea)benzamide;
(E)-N-(2-(piperidin-1-yl)ethyl)-4-(3-(4-(4-(morpholin-1-yl)-6-styrenyl-1,3,5-triazinyl-2-amino)phenyl)urea)benzamide;
(E)-N-(2-(morpholin-1-yl)ethyl)-4-(3-(4-(4-(morpholin-1-yl)-6-styrenyl-1,3,5-triazinyl-2-amino)phenyl)urea)benzamide;
(E)-1-(4-methoxyphenyl)-3-(4-((4-(morpholin-1-yl)-6-styrenyl-1,3,5-triazin-2-yl)oxo)phenyl)urea;
(E)-1-(4-chlorophenyl)-3-(4-((4-(morpholin-1-yl)-6-styrenyl-1,3,5-triazin-2-yl)oxo)phenyl)urea;
(E)-1-(4-fluorophenyl)-3-(4-((4-(morpholin-1-yl)-6-styrenyl-1,3,5-triazin-2-yl)oxo)phenyl)urea;
(E)-N-(2-(3-(1-butyn-4-yl)-3H-diazirin-3-yl)ethyl)-4-(3-(4-((4-(morpholin-1-yl)-6-styrenyl-1,3,5-triazin-2-yl)amino)phenyl)urea)benzamide; and
(E)-1-(4-carboxyphenyl)-3-(4-(4-(morpholin-1-yl)-6-styrenyl-1,3,5-triazinyl-2-amino)phenyl)urea.

8. A pharmaceutical composition, wherein the pharmaceutical composition comprises the compound, pharmaceutically acceptable salt, or solvate of claim 1 and a pharmaceutically acceptable carrier.

9. The compound, pharmaceutically acceptable salt, or solvate of claim 3, wherein $R_4$, $R_5$ and the nitrogen atom bonded to them form a saturated 4 to 6-member heterocyclic ring containing optionally an additional heteroatom selected from the group consisting of $NR_6$ and O, wherein the heterocyclic ring is optionally substituted with a substituent selected from the group consisting of hydroxyl and $C_1$-$C_6$ alkyl, wherein $R_6$ is hydrogen or $C_1$-$C_6$ alkyl.

10. The compound, pharmaceutically acceptable salt, or solvate of claim 6, wherein when $R_1$ is a group other than hydrogen, $R_1$ and $R_3$ each are independently located on a meta- or para-position of the phenyl group.

11. The compound, pharmaceutically acceptable salt, or solvate of claim 6, wherein when $R_1$ is a group other than hydrogen, $R_1$ is located on a meta-position of the phenyl group, and $R_3$ is located on a para-position of the phenyl group; the saturated heterocyclic ring is selected from the group consisting of piperazinyl, piperidinyl, pyrrolidinyl, and morpholinyl.

12. The pharmaceutical composition of claim 8, wherein the compound has a structure represented by Formula (I-1), (I-2) or (I-3):

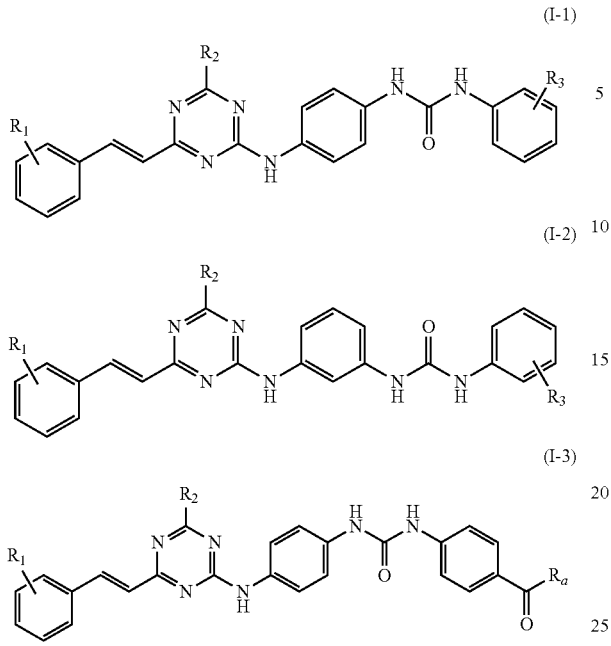

wherein, in Formula (I-1) or (I-2),
R$_1$ is hydrogen, halogen or nitro;
R$_2$ is selected from the group consisting of morpholinyl, pyrrolidinyl, piperazinyl, and azetidinyl, which are optionally substituted with hydroxyl or C$_1$-C$_6$ alkyl; and
R$_3$ is halogen or COR$_a$; wherein R$_a$ is OH or NR$_7$R$_8$, wherein R$_7$ and R$_8$ are independently selected from the group consisting of C$_1$-C$_6$ alkyl optionally substituted with NR$_9$R$_{10}$, and C$_1$-C$_6$ alkyl substituted with 3-(C$_2$-C$_6$ alkynyl)-3H-diaziridinyl; or R$_7$, R$_8$ and the nitrogen atom bonded to them form a saturated 4 to 6-member heterocyclic ring containing optionally an additional heteroatom selected from N or O, and optionally substituted with C$_1$-C$_6$ alkyl; wherein R$_9$ and R$_{10}$ are independently selected from the group consisting of hydrogen and C$_1$-C$_6$ alkyl; or R$_9$, R$_{10}$ and the nitrogen atom bonded to them form a saturated 4 to 6-member heterocyclic ring containing optionally an additional heteroatom selected from N or O;
in Formula (I-3),
R$_1$ H;
R$_2$ is morpholinyl;
R$_a$ is OH or NR$_7$R$_8$, wherein R$_7$ and R$_8$ are independently selected from the group consisting of C$_1$-C$_6$ alkyl optionally substituted with NR$_9$R$_{10}$, and C$_1$-C$_6$ alkyl substituted with 3-(C$_2$-C$_6$ alkynyl)-3H-diaziridinyl; or R$_7$, R$_8$ and the nitrogen atom bonded to them form a saturated 4 to 6-member heterocyclic ring containing optionally an additional heteroatom selected from N or O, and optionally substituted with C$_1$-C$_6$ alkyl; wherein R$_9$ and R$_{10}$ are independently selected from the group consisting of hydrogen and C$_1$-C$_6$ alkyl; or R$_9$, R$_{10}$ and the nitrogen atom bonded to them form a saturated 4 to 6-member heterocyclic ring containing optionally an additional heteroatom selected from N or O.

13. The pharmaceutical composition of claim 12, wherein in Formula (I-1),
R$_1$ is hydrogen, halogen or nitro;
R$_2$ is morpholinyl; and
R$_3$ is halogen or COR$_a$; wherein R$_a$ is OH or NR$_7$R$_8$, wherein R$_7$ and R$_8$ are independently selected from the group consisting of C$_1$-C$_6$ alkyl optionally substituted with NR$_9$R$_{10}$, and C$_1$-C$_6$ alkyl substituted with 3-(C$_2$-C$_6$ alkynyl)-3H-diaziridinyl; or R$_7$, R$_8$ and the nitrogen atom bonded to them form a saturated 4 to 6-member heterocyclic ring containing optionally an additional heteroatom selected from N or O, and optionally substituted with C$_1$-C$_6$ alkyl; wherein R$_9$ and R$_{10}$ are independently selected from the group consisting of hydrogen and C$_1$-C$_6$ alkyl; or R$_9$, R$_{10}$ and the nitrogen atom bonded to them form a saturated 4 to 6-member heterocyclic ring containing optionally an additional heteroatom selected from N or O.

14. The pharmaceutical composition of claim 13, wherein
when R$_1$ is a group other than hydrogen, R$_1$ and R$_3$ each are independently located on a meta- or para-position of the phenyl group; or
when R$_1$ is a group other than hydrogen, R$_1$ is located on a meta-position of the phenyl group, and R$_3$ is located on a para-position of the phenyl group; the saturated heterocyclic ring is selected from the group consisting of piperazinyl, piperidinyl, pyrrolidinyl, and morpholinyl.

15. The pharmaceutical composition of claim 8, wherein the compound is selected from the group consisting of:
(E)-1-(4-chlorophenyl)-3-(4-(4-(morpholin-1-yl)-6-styrenyl-1,3,5-triazinyl-2-amino)phenyl)urea;
(E)-1-(4-fluorophenyl)-3-(4-(4-(morpholin-1-yl)-6-styrenyl-1,3,5-triazinyl-2-amino)phenyl)urea;
(E)-1-(4-chlorophenyl)-3-(4-(4-(4-methylpiperazin-1-yl)-6-styrenyl-1,3,5-triazinyl-2-amino)phenyl)urea;
(E)-1-(4-fluorophenyl)-3-(4-(4-(4-methylpiperazin-1-yl)-6-styrenyl-1,3,5-triazinyl-2-amino)phenyl)urea;
(E)-1-(4-chlorophenyl)-3-(4-(4-(3-hydroxyazetidin-1-yl)-6-styrenyl-1,3,5-triazinyl-2-amino)phenyl)urea;
(E)-1-(4-chlorophenyl)-3-(4-(4-(morpholin-1-yl)-6-(3-chlorostyrenyl)-1,3,5-triazinyl-2-amino)phenyl)urea;
(E)-1-(4-fluorophenyl)-3-(4-(4-(morpholin-1-yl)-6-(3-chlorostyrenyl)-1,3,5-triazinyl-2-amino)phenyl)urea;
(E)-1-(4-chlorophenyl)-3-(4-(4-(4-methylpiperazin-1-yl)-6-(3-chlorostyrenyl)-1,3,5-triazinyl-2-amino)phenyl) urea;
(E)-1-(4-fluorophenyl)-3-(4-(4-(4-methylpiperazin-1-yl)-6-(3-chlorostyrenyl)-1,3,5-triazinyl-2-amino)phenyl) urea;
(E)-1-(4-chlorophenyl)-3-(4-(4-(morpholin-1-yl)-6-(4-chlorostyrenyl)-1,3,5-triazinyl-2-amino)phenyl)urea;
(E)-1-(4-fluorophenyl)-3-(4-(4-(morpholin-1-yl)-6-(4-chlorostyrenyl)-1,3,5-triazinyl-2-amino)phenyl)urea;
(E)-1-(3-fluorophenyl)-3-(4-(4-(morpholin-1-yl)-6-(4-chlorostyrenyl)-1,3,5-triazinyl-2-amino)phenyl)urea;
(E)-1-(4-chlorophenyl)-3-(4-(4-(4-methylpiperazin-1-yl)-6-(4-chlorostyrenyl)-1,3,5-triazinyl-2-amino)phenyl) urea;
(E)-1-(4-fluorophenyl)-3-(4-(4-(4-methylpiperazin-1-yl)-6-(4-chlorostyrenyl)-1,3,5-triazinyl-2-amino)phenyl) urea;
(E)-1-(3-fluorophenyl)-3-(4-(4-(4-methylpiperazin-1-yl)-6-(4-chlorostyrenyl)-1,3,5-triazinyl-2-amino)phenyl) urea;
(E)-1-(4-chlorophenyl)-3-(4-(4-(morpholin-1-yl)-6-(3-nitrostyrenyl)-1,3,5-triazinyl-2-amino)phenyl)urea;
(E)-1-(4-fluorophenyl)-3-(4-(4-(morpholin-1-yl)-6-(3-nitrostyrenyl)-1,3,5-triazinyl-2-amino)phenyl)urea;

(E)-1-(4-chlorophenyl)-3-(4-(4-(4-methylpiperazin-1-yl)-6-(3-nitrostyrenyl)-1,3,5-triazinyl-2-amino)phenyl)urea;
(E)-1-(4-fluorophenyl)-3-(4-(4-(4-methylpiperazin-1-yl)-6-(3-nitrostyrenyl)-1,3,5-triazinyl-2-amino)phenyl)urea;
(E)-1-(4-chlorophenyl)-3-(4-(4-dimethylamino-6-(3-nitrostyrenyl)-1,3,5-triazinyl-2-amino)phenyl)urea;
(E)-1-(4-chlorophenyl)-3-(4-(4-(pyrrolidin-1-yl)-6-(3-nitrostyrenyl)-1,3,5-triazinyl-2-amino)phenyl)urea;
(E)-1-(4-chlorophenyl)-3-(4-(4-(3-hydroxyazetidin-1-yl)-6-(3-nitrostyrenyl)-1,3,5-triazinyl-2-amino)phenyl)urea;
(E)-1-(4-chlorophenyl)-3-(3-(4-(morpholin-1-yl)-6-styrenyl-1,3,5-triazinyl-2-amino)phenyl)urea;
(E)-1-(4-chlorophenyl)-3-(3-(4-(4-methylpiperazin-1-yl)-6-styrenyl-1,3,5-triazinyl-2-amino)phenyl)urea;
(E)-1-(4-chlorophenyl)-3-(3-(4-(morpholin-1-yl)-6-(3-chlorostyrenyl)-1,3,5-triazinyl-2-amino)phenyl)urea;
(E)-1-(4-chlorophenyl)-3-(3-(4-(4-methylpiperazin-1-yl)-6-(3-chlorostyrenyl)-1,3,5-triazinyl-2-amino)phenyl)urea;
(E)-1-(4-chlorophenyl)-3-(3-(4-(morpholin-1-yl)-6-(3-nitrostyrenyl)-1,3,5-triazinyl-2-amino)phenyl)urea;
(E)-1-(4-chlorophenyl)-3-(3-(4-(4-methylpiperazin-1-yl)-6-(3-nitrostyrenyl)-1,3,5-triazinyl-2-amino)phenyl)urea;
(E)-N,N-dimethyl-4-(3-(4-(4-(morpholin-1-yl)-6-styrenyl-1,3,5-triazinyl-2-amino)phenyl)urea)benzamide;
(E)-1-(4-((4-methylpiperazin-1-yl)formyl)phenyl)-3-(4-(4-(morpholin-1-yl)-6-styrenyl-1,3,5-triazinyl-2-amino)phenyl)urea;
(E)-1-(4-((4-methylpiperazin-1-yl)formyl)phenyl)-3-(4-(4-(morpholin-1-yl)-6-styrenyl-1,3,5-triazinyl-2-amino)phenyl)urea;
(E)-N-(2-(dimethylamino)ethyl)-4-(3-(4-(4-(morpholin-1-yl)-6-styrenyl-1,3,5-triazinyl-2-amino)phenyl)urea)benzamide;
(E)-N-(2-(diethylamino)ethyl)-4-(3-(4-(4-(morpholin-1-yl)-6-styrenyl-1,3,5-triazinyl-2-amino)phenyl)urea)benzamide;
(E)-N-(3-(dimethylamino)propyl)-4-(3-(4-(4-(morpholin-1-yl)-6-styrenyl-1,3,5-triazinyl-2-amino)phenyl)urea)benzamide;
(E)-N-(2-(pyrrolidin-1-yl)ethyl)-4-(3-(4-(4-(morpholin-1-yl)-6-styrenyl-1,3,5-triazinyl-2-amino)phenyl)urea)benzamide;
(E)-N-(2-(piperidin-1-yl)ethyl)-4-(3-(4-(4-(morpholin-1-yl)-6-styrenyl-1,3,5-triazinyl-2-amino)phenyl)urea)benzamide;
(E)-N-(2-(morpholin-1-yl)ethyl)-4-(3-(4-(4-(morpholin-1-yl)-6-styrenyl-1,3,5-triazinyl-2-amino)phenyl)urea)benzamide;
(E)-1-(4-methoxyphenyl)-3-(4-((4-(morpholin-1-yl)-6-styrenyl-1,3,5-triazin-2-yl)oxo)phenyl)urea;
(E)-1-(4-chlorophenyl)-3-(4-((4-(morpholin-1-yl)-6-styrenyl-1,3,5-triazin-2-yl)oxo)phenyl)urea;
(E)-1-(4-fluorophenyl)-3-(4-((4-(morpholin-1-yl)-6-styrenyl-1,3,5-triazin-2-yl)oxo)phenyl)urea;
(E)-N-(2-(3-(1-butyn-4-yl)-3H-diazirin-3-yl)ethyl)-4-(3-(4-((4-(morpholin-1-yl)-6-styrenyl-1,3,5-triazin-2-yl)amino)phenyl)urea)benzamide; and
(E)-1-(4-carboxyphenyl)-3-(4-(4-(morpholin-1-yl)-6-styrenyl-1,3,5-triazinyl-2-amino)phenyl)urea.

16. A method for treating tissue fibrosis comprising administering the subject in need thereof the compound, pharmaceutically acceptable salt, or solvate of claim 1.

* * * * *

SEQUENCE LISTING

<160> NUMBER OF SEQ ID NOS: 1

<210> SEQ ID NO 1
<211> LENGTH: 466
<212> TYPE: PRT
<213> ORGANISM: Homo sapiens

<400> SEQUENCE: 1

```
Met Ser Thr Arg Ser Val Ser Ser Ser Tyr Arg Arg Met Phe Gly
1               5                   10                  15

Gly Pro Gly Thr Ala Ser Arg Pro Ser Ser Ser Arg Ser Tyr Val Thr
                20                  25                  30

Thr Ser Thr Arg Thr Tyr Ser Leu Gly Ser Ala Leu Arg Pro Ser Thr
                35                  40                  45

Ser Arg Ser Leu Tyr Ala Ser Ser Pro Gly Gly Val Tyr Ala Thr Arg
50                  55                  60

Ser Ser Ala Val Arg Leu Arg Ser Ser Val Pro Gly Val Arg Leu Leu
65                  70                  75                  80

Gln Asp Ser Val Asp Phe Ser Leu Ala Asp Ala Ile Asn Thr Glu Phe
                85                  90                  95

Lys Asn Thr Arg Thr Asn Glu Lys Val Glu Leu Gln Glu Leu Asn Asp
                100                 105                 110

Arg Phe Ala Asn Tyr Ile Asp Lys Val Arg Phe Leu Glu Gln Gln Asn
                115                 120                 125

Lys Ile Leu Leu Ala Glu Leu Glu Gln Leu Lys Gly Gln Gly Lys Ser
                130                 135                 140

Arg Leu Gly Asp Leu Tyr Glu Glu Met Arg Glu Leu Arg Arg Gln
145                 150                 155                 160

Val Asp Gln Leu Thr Asn Asp Lys Ala Arg Val Glu Val Glu Arg Asp
                165                 170                 175

Asn Leu Ala Glu Asp Ile Met Arg Leu Arg Glu Lys Leu Gln Glu Glu
                180                 185                 190

Met Leu Gln Arg Glu Glu Ala Glu Asn Thr Leu Gln Ser Phe Arg Gln
                195                 200                 205

Asp Val Asp Asn Ala Ser Leu Ala Arg Leu Asp Leu Glu Arg Lys Val
                210                 215                 220

Glu Ser Leu Gln Glu Glu Ile Ala Phe Leu Lys Lys Leu His Glu Glu
225                 230                 235                 240

Glu Ile Gln Glu Leu Gln Ala Gln Ile Gln Glu Gln His Val Gln Ile
                245                 250                 255

Asp Val Asp Val Ser Lys Pro Asp Leu Thr Ala Ala Leu Arg Asp Val
                260                 265                 270

Arg Gln Gln Tyr Glu Ser Val Ala Ala Lys Asn Leu Gln Glu Ala Glu
                275                 280                 285

Glu Trp Tyr Lys Ser Lys Phe Ala Asp Leu Ser Glu Ala Ala Asn Arg
                290                 295                 300

Asn Asn Asp Ala Leu Arg Gln Ala Lys Gln Glu Ser Thr Glu Tyr Arg
305                 310                 315                 320

Arg Gln Val Gln Ser Leu Thr Cys Glu Val Asp Ala Leu Lys Gly Thr
                325                 330                 335

Asn Glu Ser Leu Glu Arg Gln Met Arg Glu Met Glu Glu Asn Phe Ala
                340                 345                 350

Val Glu Ala Ala Asn Tyr Gln Asp Thr Ile Gly Arg Leu Gln Asp Glu
                355                 360                 365
```

```
Ile Gln Asn Met Lys Glu Glu Met Ala Arg His Leu Arg Glu Tyr Gln
    370             375             380
Asp Leu Leu Asn Val Lys Met Ala Leu Asp Ile Glu Ile Ala Thr Tyr
385             390             395             400
Arg Lys Leu Leu Glu Gly Glu Glu Ser Arg Ile Ser Leu Pro Leu Pro
            405             410             415
Asn Phe Ser Ser Leu Asn Leu Arg Glu Thr Asn Leu Asp Ser Leu Pro
            420             425             430
Leu Val Asp Thr His Ser Lys Arg Thr Leu Leu Ile Lys Thr Val Glu
        435             440             445
Thr Arg Asp Gly Gln Val Ile Asn Glu Thr Ser Gln His His Asp Asp
450             455             460
Leu Glu
465
```